United States Patent
Bennani et al.

(10) Patent No.: US 6,515,013 B2
(45) Date of Patent: Feb. 4, 2003

(54) 1,3-DISUBSTITUTED AND 1,3,3-TRISUBSTITUTED PYRROLIDINES AS HISTAMINE-3 RECEPTOR LIGANDS AND THEIR THERAPEUTIC APPLICATIONS

(75) Inventors: Youssef L. Bennani, Lake Bluff, IL (US); Ramin Faghih, Lake Forest, IL (US); Wesley J. Dwight, San Diego, CA (US); Anil Vasudevan, Gurnee, IL (US); Scott E. Conner, Elizabethtown, IN (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/902,925

(22) Filed: Jul. 11, 2001

(65) Prior Publication Data

US 2002/0035103 A1 Mar. 21, 2002

Related U.S. Application Data

(60) Provisional application No. 60/218,084, filed on Jul. 13, 2000.

(51) Int. Cl.$^7$ .................. C07D 207/04; A61K 31/4025
(52) U.S. Cl. ...................................... 514/426; 548/557
(58) Field of Search ............................ 548/557; 514/426

(56) References Cited

FOREIGN PATENT DOCUMENTS

| EP | 0 738 725 | 12/1997 |
|---|---|---|
| EP | 0978512 A1 | 2/2000 |
| EP | 0 982 300 | 3/2000 |
| WO | 97/49706 | 10/1996 |
| WO | 00/06254 | 2/2000 |

OTHER PUBLICATIONS

Arrang et al, "Highly potent and selective ligands for histamine $H_3$–receptors", Nature, vol. 327, (1987).
Arrang et al, "Auto–inhibition of brain histamine release mediated by a novel class ($H_3$) of histamine receptor", Nature, vol. 302, (1983), p. 832–837.
Arrang et al, "Histamine $H_3$ receptor binding sites in rat brain membranes:modulations by guanine nucleotides and divalent cations", European Journal of Pharmacology, vol. 188, (1990), pp. 219–227.
Berge et al, "Pharmaceutical Salts", Journal of Pharmaceutical Sciences, vol. 66, No. 1, (1977), pp. 1–19.
Cheng et al, "Relationship Between The Inhibition Constant ($K_1$) and the Concentration of Inhibitor Which Causes 50 Per Cent Inhibition ($I_{50}$) of an Enzymatic Reaction", Biochemical Pharmacology, vol. 22,(1993), pp. 3099–3108.
De Almeida et al, "Memory Facilitation by Histamine", Arch. Int. Pharmacodyn., vol. 283, (1986), pp. 193–198.

Delaunois et al, "Modulation of acetylcholine, capsaicin and substance P effects by histamine $H_3$ receptors in isolated perfused rabbit lungs", European Journal of Pharmacology, vol. 277, (1995), pp. 243–250.
Dimitriadou et al., "Functional relationship between mast cells and C–sensitive nerve fibres evidenced by histamine $H_3$–receptor modulation in rat lung and spleen", Clinical Science, vol. 87, (1994), pp. 151–163.
Dumery et al, "Development of amygdaloid cholinergic mediation of passive avoidance learning in the rat", Experimental Brain Research, vol. 67, (1987), pp. 61–69.
Fitzsimons et al., "Histamine receptors signalling in epidermal tumor cell lines with H–ras gene alterations", Inflammation Research, vol. 47 Supplement 1, (1998), pp. S50–S51.
Haas et al, "Subcortical modulation of synaptic plasticity in the hippocampus", Behavioral Brain Research, vol. 66, (1995), pp. 41–44.
Hatta et al., "Activation of Histamine $H_3$ Receptors Inhibits Carrier–Medicated Norepinephrine Release in a Human Model of Protracted Myocardial Ischemia", Journal of Pharmacology and Experimental Therapeutics, vol. 283, No. 2, (1997), pp. 494–500.
Murukami et al, "AQ–0145, a Newly Developed $H_3$ Antagonist Decreased Seizure Susceptibility of Electrically Induced Convulsions in Mice", Methods and Findings in Experimental and Clinical Pharmacology, vol. 17, (1995), pp. 70–73.
Imamura et al, "Activation of Histamine $H_3$–Receptors Inhibits Carrier–Mediated Norepinephrine Release During Protracted Myocardial Ischemia", Circulation Research, vol. 78, (1996), pp. 475–481.
Imamura et al, "Histamine $H_3$–Receptors–Mediated Inhibition of Calcitonin Gene–Related Peptide Release From Cardiac C Fibers", Circualtion Research, vol. 78, (1996), pp. 863–869.

(List continued on next page.)

*Primary Examiner*—Joseph K. McKane
*Assistant Examiner*—Golam M M Shameem
(74) *Attorney, Agent, or Firm*—Portia Chen; Michael J. Ward

(57) ABSTRACT

Compounds of formula I

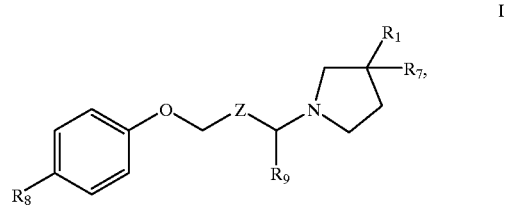

are useful in treating diseases or conditions prevented by or ameliorated with histamine-3 receptor ligands. Also disclosed are histamine-3 receptor ligand compositions and methods of antagonizing or agonizing histamine-3 receptors.

15 Claims, No Drawings

OTHER PUBLICATIONS

Kamei et al, "Influence of certain $H_1$–blockers on the step–through active avoidance response in rats", Psychopharmacology, vol. 102, (1990), pp. 312–318.

Leurs et al., "The Histamine $H_3$–Receptor: A target for developing new drugs", Progress in Drug Research, vol. 39, (1992), p. 127.

Leurs et al., "Histamine Homologues Discriminating between Two Functional $H_3$–Receptor Assays. Evidence for $H_3$ Receptor", Journal of Pharmacology and Experimental Therapeutics, vol. 276, No. 3, (1996), pp. 1009–1015.

Leurs et al., "The Medicinal Chemistry and Therapeutic Potentials of Ligands of the Histamine $H_3$–Receptor", Progress in Drug Research, vol. 45, (1995), pp. 165–170.

Leurs et al., "Therapeutic Potential of Histamine $H_3$–Receptor Agonists and Antagonists", Trends in Pharmacological Sciences, vol. 19, (1998), pp. 177–183.

Levi et al., "Histamine $H_3$–Receptors: A New Frontier in Myocardial Ischemia", Journal of Pharmacology and Experimental Therapeutics, vol. 292, (2000), pp. 825–830.

Lin et al., "Involvement of histaminergic neurons in arousal mechanisms demonstrated with $H_3$–receptor ligands in the cat", Brain Research, vol. 523, (1990), pp. 325–330.

Matsubara et al., UK–14,304, R(-)–a–methyl–histamine and SMS 201–995 block plasma protein leakage within dura mater by prejunctional mechanisms, Journal of Pharmacology, vol. 224, (1992) pp. 145–150.

Mazurkiewicz–Kwilecki et al., "Changes in the regional brain histamine and histidine levels in postmortem brains of Alzheimer patients", Canadian Journal of Research, vol. 67, (1989), pp. 75–78.

Monti et al., "Effects of selective activation or blockade of the histamine $H_3$ receptor on sleep and wakefulness", Journal of Pharmacology, vol. 205, (1991), pp. 283–287.

Monti et al., "Sleep and Waking during Acute Histamine $H_3$ Agonist BP 2.94 or $H_3$ Antagonist Carboperamide (MR 16155) Administration in Rats", Neuropsychopharmacology, vol. 15., (1996), pp. 31–35.

Onodera et al., "Neurophamacology of the Histaminergic Neuron System in the Brain and its Relationship with Behavioral Disorders", Progress in Neurobiology, vol. 46 (1994), pp. 685–702.

Panula et al., "Histamine Neurons in Human Hypothalamus: Anatomy in Normal and Alzheimer Diseased Brains", Neuroscience, vol. 44, (1998), pp. 465–481.

Philips et al., "Recent Advances in Histamine Histamine $H_3$ Receptor Agents", Annual Reports in Medicinal Chemistry, vol. 33, (1998), pp. 31–40.

Poste et al., "Lipid Vesicles as Carriers for Introducing Biologically Active Materials into Cells", Methods in Cell Biology, vol. 14, (1976), pp. 33 et seq.

Rouleau et al., "Bioavailability, Antinociceptive and Anti-inflammatory Properties of BP 2–94, a Histamine $H_3$–Receptor Agonist Prodrug", The Journal of Pharmacology and Experimental Therapeutics, vol. 281, No. 3, (1997), pp. 1085–1094.

Sakai et al., "Effects of Thiopermaide, a Histamine $H_3$–Receptor Antagonist, on Locomotor Activity and Brain Histamine Content in Mast Cell–Deficient W/W Mice", Life Sciences, vol. 48, (1991), pp. 2397–2404.

Shaywitz et al., "Dopaminergic but not noradrenergic mediation of hyperactivity and performance deficits in the developing rat pup", Psychpharmacology, vol. 82, (1984), pp. 73–77.

Tedford et al., "Pharmacological Characterization of GT—a Non–Thiourea–Containing Histamine $H_3$ Receptor Antagonist: In Vitro and In Vivo Studies", The Journal of Pharmacology and Experimental Therapeutics, vol. 75, (1995), pp. 598–604.

Tedford et al., "Abstracts", Society for Neuroscience, vol. 22, Part 1, (1996), p. 22 et seq.

Wada et al., "Is the histaminergic neuron system a regulatory center for whole–brain activity?", Trends in Neurosciences Regular ED, vol. 14, (1991), pp. 415–421.

Yokoyama et al., "Histamine and Seizures Implications for the Treatment of Epilepsy", CNS Drugs, vol. 5, (1996), p. 321–330.

Yokoyama et al., "Effect of Thioperamide, a histamine $H_3$ Receptor antagonist, on electrically induced convulsions in mice", European Journal of Pharmacology, vol. 234, (1993), pp. 129–133.

1,3-DISUBSTITUTED AND 1,3,3-TRISUBSTITUTED PYRROLIDINES AS HISTAMINE-3 RECEPTOR LIGANDS AND THEIR THERAPEUTIC APPLICATIONS

This application claims priority to the provisional application Ser. No. 60/218,084 filed on Jul. 13, 2000.

TECHNICAL FIELD

This invention relates to compounds of formula I, which may be useful for treating diseases or conditions caused by or exacerbated by histamine-3 receptor activity, pharmaceutical compositions containing compounds of formula I and methods of treatment using compounds of formula I.

BACKGROUND OF THE INVENTION

Histamine is a well-known mediator in hypersensitive reactions (e.g. allergies, hay fever, and asthma) which are commonly treated with antagonists of histamine or "antihistamines." It has also been established that histamine receptors exist in at least two distinct types, referred to as $H_1$ and $H_2$ receptors.

A third histamine receptor ($H_3$ receptor) is believed to play a role in neurotransmission in the central nervous system, where the $H_3$ receptor is thought to be disposed presynaptically on histaminergic nerve endings (Nature, 302, 832–837 (1983)). The existence of the $H_3$ receptor has been confirmed by the development of selective $H_3$ receptor agonists and antagonists (Nature, 327, 117–123 (1987)) and has subsequently been shown to regulate the release of other neurotransmitters in both the central nervous system and peripheral organs, particularly the lungs, cardiovascular system and gastrointestinal tract.

A number of diseases or conditions may be treated with histamine-3 receptor ligands wherein the $H_3$ ligand may be an antagonist, agonist or partially agonist, see: (Imamura et al., Circ.Res., (1996) 78, 475–481); (Imamura et. al., Circ.Res., (1996) 78, 863–869); (Lin et al., Brain Res. (1990) 523, 325–330); (Monti et al., Neuropsychopharmacology (1996) 15, 31–35); (Sakai, et al., Life Sci. (1991) 48, 2397–2404); (Mazurkiewicz-Kwilecki and Nsonwah, Can. J. Physiol. Pharmacol. (1989) 67, 75–78); (Panula, P. et al., Neuroscience (1998) 44, 465–481); (Wada et al., Trends in Neuroscience (1991) 14, 415); (Monti et al., Eur. J. Pharmacol. (1991) 205, 283); (Mazurkiewicz-Kwilecki and Nsonwah, Can. J. Physiol. Pharmacol. (1989) 67, 75–78); (Haas et al., Behav. Brain Res. (1995) 66, 41–44); (De Almeida and Izquierdo, Arch. Int. Pharmacodyn. (1986) 283, 193–198); (Kamei et al., Psychopharmacology (1990) 102, 312–318); (Kamei and Sakata, Jpn. J. Pharmacol. (1991) 57, 437–482); (Schwartz et al., Psychopharmacology; The fourth Generation of Progress. Bloom and Kupfer (eds). Raven Press, New York, (1995) 397); (Shaywitz et al., Psychopharmacology (1984) 82, 73–77); (Dumery and Blozovski, Exp. Brain Res. (1987) 67, 61–69); (Tedford et al., J. Pharmacol. Exp. Ther. (1995) 275, 598–604); (Tedford et al., Soc. Neurosci. Abstr. (1996) 22, 22); (Yokoyama et al., Eur. J. Pharmacol. (1993) 234, 129); (Yokoyama and Iinuma, CNS Drugs (1996) 5, 321); (Onodera et al., Prog. Neurobiol. (1994) 42, 685); (Leurs and Timmerman, Prog. Drug Res. (1992) 39, 127); (The Histamine $H_3$ Receptor, Leurs and Timmerman (eds), Elsevier Science, Amsterdam, The Netherlands (1998); (Leurs et al., Trends in Pharm. Sci. (1998) 19, 177–183); (Phillips et al., Annual Reports in Medicinal Chemistry (1998) 33, 31–40); (Matsubara et al., Eur. J. Pharmacol. (1992) 224, 145); (Rouleau et al., J. Pharmacol. Exp. Ther. (1997) 281, 1085); (Adam Szelag, "Role of histamine $H_3$-receptors in the proliferation of neoplastic cells in vitro", Med. Sci. Monit., 4(5): 747–755, (1998)); (Fitzsimons, C., H. Duran, F. Labombarda, B. Molinari and E. Rivera, "Histamine receptors signalling in epidermal tumor cell lines with H-ras gene alterations", Inflammation Res., 47 (Suppl 1): S50–S51, (1998)); (R. Leurs, R. C. Vollinga and H. Timmerman, "The medicinal chemistry and therapeutic potentials of ligand of the histamine $H_3$ receptor", Progress in Drug Research 45: 170–165, (1995)); (R. Levi and N. C. E. Smith, "Histamine $H_3$-receptors: A new frontier in myocardial ischemia", J. Pharm. Exp. Ther., 292: 825–830, (2000)); (Hatta, E., K Yasuda and R. Levi, "Activation of histamine $H_3$ receptors inhibits carrier-mediated norepinephrine release in a human model of protracted myocradial ischemia", J. Pharm. Exp. Ther., 283: 494–500, (1997); (H. Yokoyama and K. Iinuma, "Histamine and Seizures: Implications for the treatment of epilepsy", CNS Drugs, 5(5); 321–330, (1995)); (K. Hurukami, H. Yokoyama, K. Onodera, K. Iinuma and T. Watanabe, AQ-0145, "A newly developed histamine $H_3$ antagonist, decreased seizure susceptibility of eletrically induced convulsions in mice", Meth. Find. Exp. Clin. Pharmacol., 17(C): 70–73, (1995); (Delaunois A., Gustin P., Garbarg M., and Ansay M., "Modulation of acetylcholine, capsaicin and substance P effects by histamine $H_3$ receptors in isolated perfused rabbit lungs", European Journal of Pharmacology 277(2–3):243–250, (1995)); and (Dimitriadou, et al., "Functional relationship between mast cells and C-sensitive nerve fibres evidenced by histamine $H_3$-receptor modulation in rat lung and spleen", Clinical Science. 87(2):151–163, (1994). Such diseases or conditions include cardiovascular disorders such as acute myocardial infarction; memory processes, dementia and cognition disorders such as Alzheimer's disease and attention-deficit hyperactivity disorder; neurological disorders such as Parkinson's disease, schizophrenia, depression, epilepsy, and seizures or convulsions; cancer such as cutaneous carcinoma, medullary thyroid carcinoma and melanoma; respiratory disorders such as asthma; sleep disorders such as narcolepsy; vestibular dysfunction such as Meniere's disease; gastrointestinal disorders, inflammation, migraine, motion sickness, obesity, pain, and septic shock.

WO 00/06254 describes non-imidazole alkylamines as histamine-3 receptor ligands. EP 0 978 512 A1 describes non-imidazole aryloxy alkylamines as histamine-3 receptor ligands.

SUMMARY OF THE INVENTION

In its principle embodiment, the present invention discloses compounds of formula I:

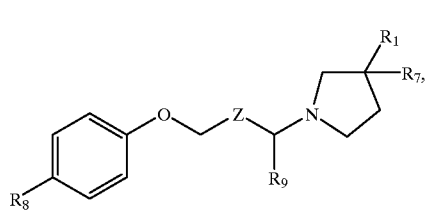

or a pharmaceutically acceptable salt thereof, wherein
  Z is selected from the group consisting of a covalent bond and $CH_2$;
  $R_1$ is selected from the group consisting of $OR_2$, $NR_3R_4$ and

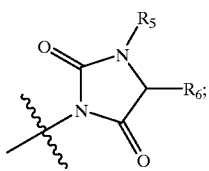

$R_2$ is selected from the group consisting of hydrogen, alkoxycarbonyl, alkyl, alkylcarbonyl, aminocarbonyl, sulfono and phosphono;

$R_3$ and $R_4$ are independently selected from the group consisting of hydrogen, alkenyl, alkenylcarbonyl, alkenyloxycarbonyl, alkenylsulfonyl, alkoxycarbonyl, alkyl, alkylcarbonyl, alkylsulfonyl, alkynyl, alkynylcarbonyl, alkynyloxycarbonyl, alkynylsulfonyl, aminocarbonyl, aminosulfonyl, arylalkyl, arylalkenylcarbonyl, arylalkenylsulfonyl, arylalkylcarbonyl, arylalkylsulfonyl, arylarylcarbonyl, arylarylsulfonyl, arylcarbonyl, arylheterocylecarbonyl, arylheterocylesulfonyl, aryloxyarylcarbonyl, aryloxyarylsulfonyl, arylsulfonyl, cycloalkyl, cycloalkylalkyl, cycloalkylalkylcarbonyl, cycloalkylalkylsulfonyl, cycloalkylcarbonyl, cycloalkylsulfonyl, formyl, heterocycle, heterocyclealkyl, heterocyclealkylcarbonyl, heterocyclealkylsulfonyl, heterocyclearylcarbonyl, heterocyclearylsulfonyl, heterocyclecarbonyl, heterocycleheterocyclecarbonyl, heterocycleheterocyclesulfonyl, heterocycleoxyalkylcarbonyl, heterocycleoxyarylcarbonyl, heterocycleoxyarylsulfonyl, heterocyclesulfonyl, and heterocyclethioalkylcarbonyl;

$R_5$ and $R_6$ are independently selected from the group consisting of hydrogen and alkyl;

$R_7$ is selected from the group consisting of hydrogen and alkyl; or $R_1$ and $R_7$ together form (=O);

$R_8$ is selected from the group consisting of alkylcarbonyl, aryl, arylcarbonyl, arylcarbonylaryl, arylcarbonylheterocycle, cycloalkylcarbonyl, cycloalkylcarbonylaryl, cycloalkylcarbonylheterocycle, heterocycle, heterocyclecarbonyl, heterocyclecarbonylaryl, heterocyclecarbonylheterocycle; and $R_9$ is selected from the group consisting of hydrogen and lower alkyl.

DETAILED DESCRIPTION OF THE INVENTION

All patents, patent applications, and literature references cited in the specification are herein incorporated by reference in their entirety. In the case of inconsistencies, the present disclosure, including definitions, will prevail.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

In its principle embodiment, the present invention discloses compounds of formula I:

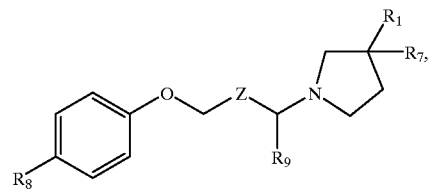

or a pharmaceutically acceptable salt, ester, amide or prodrug thereof, wherein

Z is selected from a covalent bond and $CH_2$;

$R_1$ is selected from $OR_2$, $NR_3R_4$ and

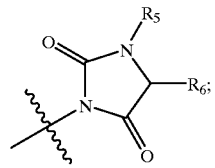

$R_2$ is selected from the group consisting of hydrogen, alkoxycarbonyl, alkyl, alkylcarbonyl, aminocarbonyl, sulfono and phosphono; $R_3$ and $R_4$ are independently selected from hydrogen, alkenyl, alkenylcarbonyl, alkenyloxycarbonyl, alkenylsulfonyl, alkoxycarbonyl, alkyl, alkylcarbonyl, alkylsulfonyl, alkynyl, alkynylcarbonyl, alkynyloxycarbonyl, alkynylsulfonyl, aminocarbonyl, aminosulfonyl, arylalkyl, arylalkenylcarbonyl, arylalkenylsulfonyl, arylalkylcarbonyl, arylalkylsulfonyl, arylarylcarbonyl, arylarylsulfonyl, arylcarbonyl, arylheterocylecarbonyl, arylheterocylesulfonyl, aryloxyarylcarbonyl, aryloxyarylsulfonyl, arylsulfonyl, cycloalkyl, cycloalkylalkyl, cycloalkylalkylcarbonyl, cycloalkylalkylsulfonyl, cycloalkylcarbonyl, cycloalkylsulfonyl, formyl, heterocycle, heterocyclealkyl, heterocyclealkylcarbonyl, heterocyclealkylsulfonyl, heterocyclearylcarbonyl, heterocyclearylsulfonyl, heterocyclecarbonyl, heterocycleheterocyclecarbonyl, heterocycleheterocyclesulfonyl, heterocycleoxyalkylcarbonyl, heterocycleoxyarylcarbonyl, heterocycleoxyarylsulfonyl, heterocyclesulfonyl, and heterocyclethioalkylcarbonyl;

$R_5$ and $R_6$ are independently selected from hydrogen and alkyl;

$R_7$ is selected from hydrogen and alkyl; or $R_1$ and $R_7$ together form (=O);

$R_8$ is selected from the group consisting of alkylcarbonyl, aryl, arylcarbonyl, arylcarbonylaryl, arylcarbonylheterocycle, cycloalkylcarbonyl, cycloalkylcarbonylaryl, cycloalkylcarbonylheterocycle, heterocycle, heterocyclecarbonyl, heterocyclecarbonylaryl, heterocyclecarbonylheterocycle;

$R_9$ is selected from the group consisting of hydrogen and lower alkyl;

wherein at each occurrence of said aryl, arylalkenylcarbonyl, arylalkenylsulfonyl, arylalkylcarbonyl, arylalkylsulfonyl, arylarylcarbonyl, arylarylsulfonyl, arylcarbonyl, arylcarbonylaryl, arylcarbonylheterocycle, arylheterocylecarbonyl, arylheterocylesulfonyl, aryloxyarylcarbonyl, aryloxyarylsulfonyl, arylsulfonyl, cycloalkylcarbonylaryl, heterocyclearylcarbonyl, heterocyclearylsulfonyl, heterocyclecarbonylaryl, heterocycleoxyarylcarbonyl, and heterocycleoxyarylsulfonyl, the aryl portion can be optionally substituted with 1, 2, or 3 substituents selected from the group consisting of alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, carboxy, carboxyalkyl, cyano, cyanoalkyl, formyl, halogen, haloalkoxy, haloalkyl, hydroxy, hydroxyalkyl, mercapto, and nitro; and wherein at each occurrence of said arylcarbonylheterocycle, arylheterocylecarbonyl, arylheterocylesulfonyl, cycloalkylcarbonylheterocycle, heterocycle, heterocyclealkyl, heterocyclealkylcarbonyl, heterocyclealkylsulfonyl, heterocyclearylcarbonyl, heterocyclearylsulfonyl, heterocyclecarbonyl, heterocyclecarbonylaryl, heterocyclecarbonylheterocycle, heterocycleheterocyclecarbonyl, heterocycleheterocyclesulfonyl, heterocycleoxyalkylcarbonyl, heterocycleoxyarylcarbonyl, heterocycleoxyarylsulfonyl, heterocyclesulfonyl, and heterocyclethioalkylcarbonyl, the heterocycle portion can be optionally substituted with 1, 2, or 3 substituents selected from the group consisting of alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

In a preferred embodiment, compounds of the present invention have formula I wherein $R_1$ is $NR_3R_4$; $R_3$ and $R_4$ are independently selected from hydrogen, alkenyl, alkenylcarbonyl, alkenyloxycarbonyl, alkenylsulfonyl, alkoxycarbonyl, alkyl, alkylcarbonyl, alkylsulfonyl, alkynyl, alkynylcarbonyl, alkynyloxycarbonyl, alkynylsulfonyl, aminocarbonyl, aminosulfonyl, arylalkyl, arylalkenylcarbonyl, arylalkenylsulfonyl, arylalkylcarbonyl, arylalkylsulfonyl, arylarylcarbonyl, arylarylsulfonyl, arylcarbonyl, arylheterocylecarbonyl, arylheterocylesulfonyl, aryloxyarylcarbonyl, aryloxyarylsulfonyl, arylsulfonyl, cycloalkyl, cycloalkylalkyl, cycloalkylalkylcarbonyl, cycloalkylalkylsulfonyl, cycloalkylcarbonyl, cycloalkylsulfonyl, heterocycle, heterocyclealkyl, heterocyclealkylcarbonyl, heterocyclealkylsulfonyl, heterocyclearylcarbonyl, heterocyclearylsulfonyl, heterocyclecarbonyl, heterocycleheterocyclecarbonyl, heterocycleheterocyclesulfonyl, heterocycleoxyalkylcarbonyl, heterocycleoxyarylcarbonyl, heterocycleoxyarylsulfonyl, heterocyclesulfonyl, and heterocyclethioalkylcarbonyl; $R_7$ is hydrogen; $R_8$ is selected from alkylcarbonyl, cycloalkylcarbonyl, aryl, heterocycle, heterocyclecarbonylaryl and heterocyclecarbonylheterocycle; and Z and $R_9$ are as defined in formula I.

In another preferred embodiment, compounds of the present invention have formula I wherein $R_1$ is $NR_3R_4$; $R_3$ and $R_4$ are independently selected from hydrogen, alkenyloxycarbonyl, alkoxycarbonyl, alkyl, alkylcarbonyl, alkylsulfonyl, aminocarbonyl, aminosulfonyl, arylalkenylsulfonyl, arylcarbonyl, arylsulfonyl, cycloalkylcarbonyl, heterocyclecarbonyl, heterocycleheterocyclecarbonyl, heterocycleheterocyclesulfonyl, heterocycleoxyarylsulfonyl, heterocyclesulfonyl, and heterocyclethioalkylcarbonyl; $R_7$ is hydrogen; $R_8$ is selected from alkylcarbonyl, cycloalkylcarbonyl, aryl, heterocycle, heterocyclecarbonylaryl and heterocyclecarbonylheterocycle; and Z and $R_9$ are as defined in formula I.

In another preferred embodiment, compounds of the present invention have formula I wherein Z is $CH_2$; $R_1$ is $NR_3R_4$; $R_3$ and $R_4$ are independently selected from hydrogen, alkoxycarbonyl and alkyl; $R_7$ is hydrogen; $R_8$ is selected from the group consisting of acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; and $R_9$ is hydrogen.

In another preferred embodiment, compounds of the present invention have formula I wherein Z is a covalent bond; $R_1$ is $NR_3R_4$; $R_3$ and $R_4$ are independently selected from hydrogen, alkoxycarbonyl and alkyl; $R_7$ is hydrogen; $R_8$ is selected from the group consisting of acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; and $R_9$ is hydrogen.

In another preferred embodiment, compounds of the present invention have formula II

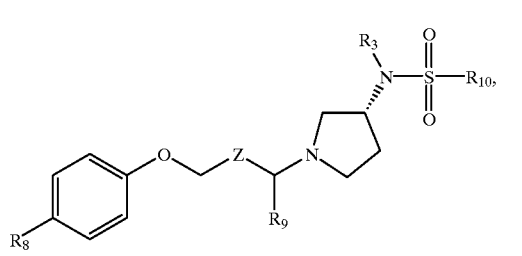

or a pharmaceutically acceptable salt, ester, amide or prodrug thereof wherein $R_{10}$ is selected from alkenyl, alkyl, alkynyl, amino, aryl, arylalkenyl, arylalkyl, arylaryl, arylheterocycle, aryloxyaryl, cycloalkyl, cycloalkylalkyl, heterocycle, heterocyclealkyl, heterocyclearyl, heterocycleheterocycle and heterocycleoxyaryl; and Z, $R_3$, $R_8$ and $R_9$ are as defined in formula I.

In another preferred embodiment, compounds of the present invention have formula II wherein $R_3$ is selected from hydrogen and alkyl; $R_8$ is selected from alkylcarbonyl, cycloalkylcarbonyl, aryl, heterocycle, heterocyclecarbonylaryl and heterocyclecarbonylheterocycle; $R_{10}$ is selected from alkyl, amino, aryl, arylalkenyl, heterocycle, heterocycleheterocycle and heterocycleoxyaryl; and Z and R₉ are as defined in formula I.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is selected from alkyl and amino.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is aryl wherein said aryl is phenyl optionally substituted with 1 or 2 substitutuents selected from alkoxy, alkyl, alkylsufonyl, amino, cyano, haloalkoxy, haloalkyl, halogen.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is arylalkenyl wherein the aryl portion of said arylalkenyl is phenyl.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is heterocycle wherein said heterocycle is selected from the group consisting of benzothienyl, imidazolyl, isoquinolinyl, pyridinyl, pyrrolyl, quinolinyl, thiazolyl, and thienyl, wherein said benzothienyl, imidazolyl, isoquinolinyl, pyridinyl, pyrrolyl, quinolinyl, thiazolyl, and thienyl are each optionally substituted with 1 or 2 substituents selected from alkoxy, alkyl, amino, haloalkyl, and halogen.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is heterocycleheterocycle wherein said heterocycleheterocycle is (3-chloro-5-(trifluoromethyl)-2-pyridinyl)-1H-pyrrol-2-yl.

In another preferred embodiment, compounds of the present invention have formula II wherein Z is CH₂; R₃ is selected from hydrogen and alkyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; R₉ is hydrogen; and R₁₀ is heterocycleoxyaryl wherein said heterocycleoxyaryl is (3-chloro-5-(trifluoromethyl)-2-pyridinyl)oxy)phenyl).

In another preferred embodiment, compounds of the present invention have formula

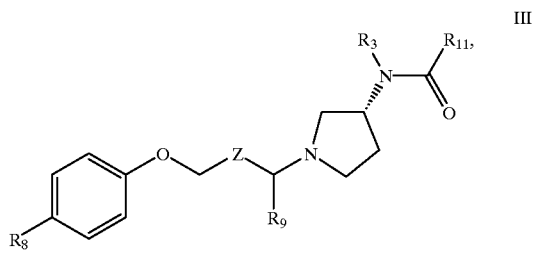

III or a pharmaceutically acceptable salt, ester, amide or prodrug thereof wherein R₁₁ is selected from hydrogen, alkenyl, alkenyloxy, alkoxy, alkyl, alkynyl, alkynyloxy, amino, aryl, arylalkenyl, arylalkyl, arylaryl, arylheterocycle, aryloxyaryl, cycloalkyl, cycloalkylalkyl, heterocycle, heterocyclealkyl, heterocyclearyl, heterocycleheterocycle, heterocycleoxyalkyl, heterocycleoxyaryl and heterocyclethioalkyl; and Z, R₃, R₈ and R₉ are as defined in formula I.

In another preferred embodiment, compounds of the present invention have formula III wherein R₃ is selected from hydrogen, alkyl, alkylcarbonyl, aminocarbonyl, arylcarbonyl, and heterocyclecarbonyl; R₈ is selected from alkylcarbonyl, cycloalkylcarbonyl, aryl, heterocycle, heterocyclecarbonylaryl and heterocyclecarbonylheterocycle; and R₁₁ is selected from alkenyloxy, alkoxy, alkyl, amino, aryl, cycloalkyl, heterocycle, heterocycleheterocycle and heterocyclethioalkyl; and Z and R₉ are as defined in formula I.

In another preferred embodiment, compounds of the present invention have formula III wherein Z is CH₂; R₃ is selected from hydrogen, alkyl, alkylcarbonyl, and aminocarbonyl; R₈ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1- azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_{11}$ is selected from alkenyloxy, alkoxy, alkyl, amino, and cycloalkyl.

In another preferred embodiment, compounds of the present invention have formula III wherein Z is $CH_2$; $R_3$ is selected from hydrogen, alkyl, and arylcarbonyl wherein the aryl portion of said arylcarbonyl is phenyl optionally substituted with 1 substituent selected from cyano and halogen; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_{11}$ is aryl wherein said aryl is phenyl optionally substituted with 1 substituent selected from cyano and halogen.

In another preferred embodiment, compounds of the present invention have formula III wherein Z is $CH_2$; $R_3$ is selected from hydrogen, alkyl, and heterocyclecarbonyl wherein the heterocycle portion of said heterocyclecarbonyl is selected from 4-morpholinyl and 1-pyrrolidinyl; $R_8$ is selected from acetyl, propionyl, cyclopropylcarbonyl, 4-cyanophenyl, 2-yridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_{11}$ is heterocycle wherein said heterocycle is selected from furyl, 4-morpholinyl, pyridinyl, and pyrrolidinyl.

In another preferred embodiment, compounds of the present invention have formula III wherein Z is $CH_2$; $R_3$ is selected from hydrogen and alkyl; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_{11}$ is heterocycleheterocycle wherein said heterocycleheterocycle is 2-(3-pyridinyl)-1,3-thiazol-4-yl.

In another preferred embodiment, compounds of the present invention have formula III wherein Z is $CH_2$; $R_3$ is selected from hydrogen and alkyl; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_{11}$ is heterocyclethioalkyl wherein said heterocyclethioalkyl is [(4-methyl-2-pyrimidinyl)sulfanyl]methyl.

In another preferred embodiment, compounds of the present invention have formula IV

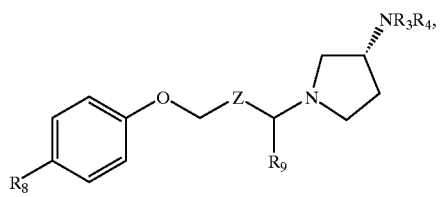

or a pharmaceutically acceptable salt, ester, amide or prodrug thereof wherein $R_3$ and $R_4$ are independently selected from hydrogen, alkenyl, alkyl, alkynyl, arylalkyl, cycloalkyl, cycloalkylalkyl, heterocycle and heterocyclealkyl; and Z, $R_8$ and $R_9$ are as defined in formula I.

In another preferred embodiment, compounds of the present invention have formula IV wherein $R_3$ and $R_4$ are independently selected from hydrogen and alkyl; $R_8$ is selected from alkylcarbonyl, cycloalkylcarbonyl, aryl, heterocycle, heterocyclecarbonylaryl and heterocyclecarbonylheterocycle; and Z and $R_9$ are as defined in formula I.

In another preferred embodiment, compounds of the present invention have formula IV wherein Z is $CH_2$; $R_3$ and $R_4$ are independently selected from hydrogen and alkyl; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; and $R_9$ is hydrogen.

In another preferred embodiment, compounds of the present invention have formula V

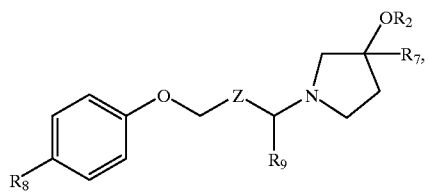

or a pharmaceutically acceptable salt, ester, amide or prodrug thereof wherein Z, $R_2$, $R_7$, $R_8$ and $R_9$ are as defined in formula I.

In another preferred embodiment, compounds of the present invention have formula V wherein $R_8$ is selected from alkylcarbonyl, cycloalkylcarbonyl, aryl, heterocycle, heterocyclecarbonylaryl and heterocyclecarbonylheterocycle; and Z, $R_2$, $R_7$ and $R_9$ are as defined in formula I.

In another preferred embodiment, compounds of the present invention have formula V wherein Z is $CH_2$; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_2$ and $R_7$ are as defined in formula I.

In another preferred embodiment, compounds of the present invention have formula VI

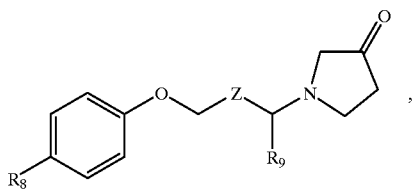

or a pharmaceutically acceptable salt, ester, amide or prodrug thereof wherein Z, $R_8$ and $R_9$ are as defined in formula I.

In another preferred embodiment, compounds of the present invention have formula VI wherein $R_8$ is selected from alkylcarbonyl, cycloalkylcarbonyl, aryl, heterocycle, heterocyclecarbonylaryl and heterocyclecarbonylheterocycle; Z and $R_9$ are as defined in formula I.

In another preferred embodiment, compounds of the present invention have formula VI wherein Z is $CH_2$; $R_9$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; and $R_9$ is hydrogen.

In another preferred embodiment, compounds of the present invention have formula VII

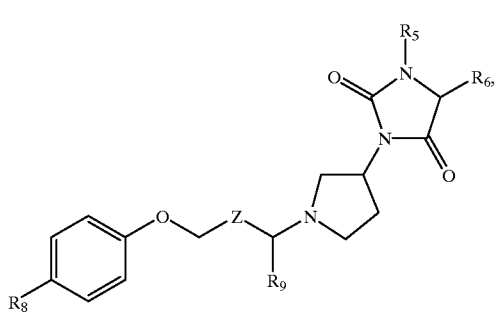

or a pharmaceutically acceptable salt, ester, amide or prodrug thereof wherein Z, $R_5$, $R_6$, $R_8$ and $R_9$ are as defined in formula I.

In another preferred embodiment, compounds of the present invention have formula VII wherein $R_8$ is selected from alkylcarbonyl, cycloalkylcarbonyl, aryl, heterocycle, heterocyclecarbonylaryl and heterocyclecarbonylheterocycle; Z, $R_5$, $R_6$ and $R_9$ are as defined in formula I.

In another preferred embodiment, compounds of the present invention have formula VII wherein Z is $CH_2$; $R_8$ is selected from acetyl, propionyl, cyclopropylcarbonyl, 4-cyanophenyl, 2-pyridinyl, 4-(1-pyrrolidinylcarbonyl)phenyl, 4-(1-pyrrolidinylcarbonyl)-1-piperazinyl, 4-(1-piperidinylcarbonyl)phenyl, 4-(1-piperidinylcarbonyl)-1-piperazinyl, 4-(4-morpholinylcarbonyl)phenyl, 4-(4-morpholinylcarbonyl)-1-piperazinyl, 4-(1-azetidinylcarbonyl)phenyl, 4-(1-azetidinylcarbonyl)-1-piperazinyl, 4-(1-piperazinylcarbonyl)phenyl, 4-(1-piperazinylcarbonyl)-1-piperazinyl; $R_9$ is hydrogen; and $R_5$ and $R_6$ are as defined in formula I.

Another embodiment of the present invention relates to pharmaceutical compositions comprising a therapeutically effective amount of a compound of formula I-VII or a pharmaceutically acceptable salt, ester, amide, or prodrug thereof in combination with a pharmaceutically acceptable carrier.

Another embodiment of the invention relates to a method of modulating the effects of the histamine-3 receptor by agonism of the histamine-3 receptor in a mammal comprising administering a therapeutically effective amount of a compound of formula I-VII or a pharmaceutically acceptable salt, ester, amide, or prodrug thereof in combination with a pharmaceutically acceptable carrier.

Another embodiment of the invention relates to a method of modulating the effects of the histamine-3 receptor by antagonism of the histamine-3 receptor in a mammal comprising administering a therapeutically effective amount of a compound of formula I-VII or a pharmaceutically acceptable salt, ester, amide, or prodrug thereof in combination with a pharmaceutically acceptable carrier.

Another embodiment of the invention relates to a method of treating acute myocardial infarction, Alzheimer's disease, asthma, attention-deficit hyperactivity disorder, cutaneous carcinoma, depression, epilepsy, inflammation, medullary thyroid carcinoma, melanoma, Meniere's disease, migraine, motion sickness, narcolepsy, obesity, pain, Parkinson's disease, schizophrenia, seizures or septic shock comprising administering a therapeutically effective amount of a compound of formula I-VII or a pharmaceutically acceptable salt, ester, amide, or prodrug thereof in combination with a pharmaceutically acceptable carrier.

Definition of Terms

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylcarbonyl," as used herein, refers to an alkenyl group, as defined herein, appended to the parent molecular moiety through a carbonyl group, as defined herein. Representative examples of alkenylcarbonyl include, but are not limited to, 3-butenoyl, 3-pentenoyl, and 4-pentenoyl.

The term "alkenyloxy," as used herein, refers to an alkenyl group, as defined herein, appended to the parent molecular moiety through an oxy group, as defined herein. Representative examples of alkenyloxy include, but are not limited to, allyloxy, 2-butenyloxy, and 3-butenyloxy.

The term "alkenyloxycarbonyl," as used herein, refers to an alkenyloxy group, as defined herein, appended to the parent molecular moiety through a carbonyl group, as defined herein. Representative examples of alkenyloxycarbonyl include, but are not limited to, allyloxycarbonyl, 2-butenyloxycarbonyl, and 3-butenyloxycarbonyl.

The term "alkenylsulfonyl," as used herein, refers to an alkenyl group, as defined herein, appended to the parent molecular moiety through a sulfonyl group, as defined herein. Representative examples of alkenylsulfonyl include, but are not limited to, allylsulfonyl, 2-butenylsulfonyl, and 3-butenylsulfonyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and tert-butylcarbonyloxy.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, ethylsulfonyl, isopropylsulfonyl, and methylsulfonyl.

The term "alkylthio," as used herein, refers to an alkyl group, as defined herein, appended to the parent molecular moiety through a thio moiety, as defined herein. Representative examples of alkylthio include, but are not limited to, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkynylcarbonyl," as used herein, refers to an alkynyl group, as defined herein, appended to the parent molecular moiety through a carbonyl group, as defined herein. Representative examples of alkynylcarbonyl include, but are not limited to, 3-butynoyl, 3-pentynoyl, and 4-pentynoyl.

The term "alkynyloxy," as used herein, refers to an alkynyl group, as defined herein, appended to the parent molecular moiety through an oxy group, as defined herein. Representative examples of alkynyloxy include, but are not limited to, 2-butynyloxy, and 3-butynyloxy.

The term "alkynyloxycarbonyl," as used herein, refers to an alkynyloxy group, as defined herein, appended to the parent molecular moiety through a carbonyl group, as defined herein. Representative examples of alkynyloxycarbonyl include, but are not limited to, 2-butynyloxycarbonyl, and 3-butynyloxycarbonyl.

The term "alkynylsulfonyl," as used herein, refers to an alkynyl group, as defined herein, appended to the parent molecular moiety through a sulfonyl group, as defined herein. Representative examples of alkynylsulfonyl include, but are not limited to, 2-butynylsulfonyl, and 3-butynylsulfonyl.

The term "amino," as used herein, refers to a —$NR_AR_B$ group wherein $R_A$ and $R_B$ are independently selected from hydrogen, alkyl, alkylcarbonyl, and benzyl. Representative examples of amino include but are not limited to acetylamino, amino, benzylamino, dimethylamino, and methylamino.

The term "aminoalkyl," as used herein, refers to an amino group, as defined herein, appended to the parent molecular moiety through an alkyl group, as defined herein. Representative examples of aminoalkyl include, but are not limited, (amino)methyl, (dimethylamino)methyl, 2-(benzylamino)ethyl, and (ethylamino)methyl.

The term "aminocarbonyl," as used herein, refers to an amino group, as defined herein, appended to the parent molecular moiety through a carbonyl group, as defined herein. Representative examples of aminocarbonyl include, but are not limited, aminocarbonyl, dimethylaminocarbonyl, benzylaminocarbonyl, and ethylaminocarbonyl.

The term "aminosulfonyl," as used herein, refers to an amino group, as defined herein, appended to the parent molecular moiety through a sulfonyl group, as defined herein. Representative examples of aminosulfonyl include, but are not limited, aminosulfonyl, dimethylaminosulfonyl, benzylaminosulfonyl, and ethylaminosulfonyl.

The term "aryl," as used herein, refers to a monocyclic-ring system, or a bicyclic- or a tricyclic- fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 1, 2, or 3 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "arylalkenyl," as used herein, refers to an aryl group, as defined herein, appended to the parent molecular moiety through an alkenyl group, as defined herein. Representative examples of arylalkenyl include, but are not limited to, 3-phenyl-1-propenyl, and 2-(2-naphthyl)ethenyl.

The term "arylalkenylcarbonyl," as used herein, refers to an arylalkenyl group, as defined herein, appended to the parent molecular moiety through a carbonyl group, as defined herein. Representative examples of arylalkenylcarbonyl include, but are not limited to, 4-phenyl-3-butenoyl, and 3-phenyl-2-propenoyl.

The term "arylalkenylsulfonyl," as used herein, refers to an arylalkenyl group, as defined herein, appended to the parent molecular moiety through a sulfonyl group, as defined herein. Representative examples of arylalkenylsulfonyl include, but are not limited to, 2-phenylethenylsulfonyl, and 4-phenyl-3-butenylsulfonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylcarbonyl," as used herein, refers to an arylalkyl group, as defined herein, appended to the parent molecular moiety through a carbonyl group, as defined herein. Representative examples of arylalkylcarbonyl include, but are not limited to, phenylacetyl, 4-phenylbutanoyl, and 3-phenylpropanoyl.

The term "arylalkylsulfonyl," as used herein, refers to an arylalkyl group, as defined herein, appended to the parent molecular moiety through a sulfonyl group, as defined herein. Representative examples of arylalkylsulfonyl include, but are not limited to, (2-phenylethyl)sulfonyl, and (3-phenylpropyl)sulfonyl.

The term "arylaryl," as used herein, refers to an aryl group, as defined herein, appended to the parent molecular moiety through another aryl group, as defined herein. Representative examples of arylaryl include, but are not limited to, (1,1'-biphenyl), and (2'-chloro(1,1'-biphenyl)-3-yl).

The term "arylarylcarbonyl," as used herein, refers to an arylaryl group, as defined herein, appended to the parent molecular moiety through a carbonyl group, as defined herein. Representative examples of arylarylcarbonyl include, but are not limited to, (1,1'-biphenyl)carbonyl, and (2'-chloro(1,1'-biphenyl)-3-yl)carbonyl.

The term "arylarylsulfonyl," as used herein, refers to an arylaryl group, as defined herein, appended to the parent molecular moiety through a sulfonyl group, as defined herein. Representative examples of arylarylsulfonyl include, but are not limited to, (1,1'-biphenyl)sulfonyl, and (2'-chloro(1,1'-biphenyl)-3-yl)sulfonyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, 4-cyanobenzoyl, and naphthoyl.

The term "arylcarbonylaryl," as used herein, refers to an arylcarbonyl group, as defined herein, appended to the parent molecular moiety through an aryl group, as defined herein. Representative examples of arylcarbonylaryl include, but are not limited to, 4-(benzoyl)phenyl and 4-(benzoyl)naphthyl.

The term "arylcarbonylheterocycle," as used herein, refers to an arylcarbonyl group, as defined herein, appended to the parent molecular moiety through a heterocycle group, as defined herein. Representative examples of arylcarbonylheterocycle include, but are not limited to, 4-benzoyl-1-piperazinyl and 1-benzoyl-4-piperidinyl.

The term "arylheterocycle," as used herein, refers to an aryl group, as defined herein, appended to the parent molecular moiety through a heterocycle group, as defined herein. Representative examples of arylheterocycle include, but are not limited to, 5-phenylpyridin-2-yl and 5-(3-chlorophenyl)pyridin-2-yl.

The term "arylheterocyclecarbonyl," as used herein, refers to an arylheterocycle group, as defined herein, appended to the parent molecular moiety through a carbonyl group, as defined herein. Representative examples of arylheterocyclecarbonyl include, but are not limited to, 5-phenylpyridin-2-ylcarbonyl and 5-(3-chlorophenyl)pyridin-2-ylcarbonyl.

The term "arylheterocyclesulfonyl," as used herein, refers to an arylheterocycle group, as defined herein, appended to the parent molecular moiety through a sulfonyl group, as defined herein. Representative examples of arylheterocyclesulfonyl include, but are not limited to, 5-phenylpyridin-2-ylsulfonyl and 5-(3-chlorophenyl)pyridin-2-ylsulfonyl.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyaryl," as used herein, refers to an aryloxy group, as defined herein, appended to the parent molecular moiety through an aryl group, as defined herein. Representative examples of aryloxyaryl include, but are not limited to, 3-(3-methylphenoxy)phenyl, and 3-(3-bromophenoxy)phenyl.

The term "aryloxyarylcarbonyl," as used herein, refers to an aryloxyaryl group, as defined herein, appended to the parent molecular moiety through a carbonyl group, as defined herein. Representative examples of aryloxyarylcarbonyl include, but are not limited to, 3-(3-methylphenoxy)benzoyl, and 3-(3-bromophenoxy)benzoyl.

The term "aryloxyarylsulfonyl," as used herein, refers to an aryloxyaryl group, as defined herein, appended to the parent molecular moiety through a sulfonyl group, as defined herein. Representative examples of aryloxyarylsulfonyl include, but are not limited to, 3-(3-methylphenoxy)phenylsulfonyl, and 3-(3-bromophenoxy)phenylsulfonyl.

The term "arylsulfonyl," as used herein, refers to an aryl group, as defined herein, appended to the parent molecular moiety through a sulfonyl group, as defined herein. Representative examples of arylsulfonyl include, but are not limited to, phenylsulfonyl, (4-acetylaminophenyl)sulfonyl, (4-chlorophenyl)sulfonyl, (4-cyanophenyl)sulfonyl, (4-methoxyphenyl)sulfonyl, (4-methylphenyl)sulfonyl, and (4-(tert-butyl)phenyl)sulfonyl.

The term "arylthio," as used herein, refers to an aryl group, as defined herein, appended to the parent molecular moiety through a thio moiety, as defined herein. Representative examples of arylthio include, but are not limited to, phenylsulfanyl, naphth-2-ylsulfanyl, and 5-phenylhexylsulfanyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkylalkylcarbonyl," as used herein, refers to cycloalkylalkyl group, as defined herein, appended to the parent molecular moiety through a carbonyl group, as defined herein. Representative examples of cycloalkylalkylcarbonyl include, but are not limited to, cyclopropylmethylcarbonyl, 2-cyclobutylethylcarbonyl, cyclopentylmethylcarbonyl, cyclohexylmethylcarbonyl, and 4-cycloheptylbutylcarbonyl.

The term "cycloalkylalkylsulfonyl," as used herein, refers to cycloalkylalkyl group, as defined herein, appended to the parent molecular moiety through a sulfonyl group, as defined herein. Representative examples of cycloalkylalkylsulfonyl include, but are not limited to, cyclopropylmethylsulfonyl, 2-cyclobutylethylsulfonyl, cyclopentylmethylsulfonyl, cyclohexylmethylsulfonyl, and 4-cycloheptylbutylsulfonyl.

The term "cycloalkylcarbonyl," as used herein, refers to a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, and cyclohexylcarbonyl.

The term "cycloalkylcarbonylaryl," as used herein, refers to a cycloalkylcarbonyl group, as defined herein, appended to the parent molecular moiety through an aryl group, as defined herein. Representative examples of cycloalkylcarbonylaryl include, but are not limited to, 4-(cyclopropylcarbonyl)phenyl, 4-(cyclopentylcarbonyl) phenyl, and 4-(cyclohexylcarbonyl)phenyl.

The term "cycloalkylcarbonylheterocycle," as used herein, refers to a cycloalkylcarbonyl group, as defined herein, appended to the parent molecular moiety through a heterocycle group, as defined herein. Representative examples of cycloalkylcarbonylheterocycle include, but are not limited to, 4-(cyclopropylcarbonyl)-1-piperazinyl, 4-(cyclopentylcarbonyl)-1-piperazinyl, and 4-(cyclohexylcarbonyl)-1-piperazinyl.

The term "cycloalkylsulfonyl," as used herein, refers to cycloalkyl group, as defined herein, appended to the parent molecular moiety through a sulfonyl group, as defined herein. Representative examples of cycloalkylsulfonyl include, but are not limited to, cyclopropylsulfonyl, cyclopentylsulfonyl, and cyclohexylsulfonyl.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl.

The heterocycles of this invention can be substituted with 1, 2,or 3 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclealkylcarbonyl," as used herein, refers to a heterocyclealkyl, as defined herein, appended to the parent molecular moiety through a carbonyl group, as defined herein. Representative examples of heterocyclealkylcarbonyl include, but are not limited to, (pyridin-3-ylmethyl)carbonyl and (2-(pyrimidin-2-yl)propyl)carbonyl.

The term "heterocyclealkylsulfonyl," as used herein, refers to a heterocyclealkyl, as defined herein, appended to the parent molecular moiety through a sulfonyl group, as defined herein. Representative examples of heterocyclealkylsulfonyl include, but are not limited to, (pyridin-3-ylmethyl)sulfonyl and (2-(pyrimidin-2-yl)propyl)sulfonyl.

The term "heterocyclearyl," as used herein, refers to a heterocycle, as defined herein, appended to the parent molecular moiety through an aryl group, as defined herein. Representative examples of heterocyclearyl include, but are not limited to, 4-(pyridin-3-yl)phenyl and 4-(pyrimidin-2-yl)phenyl.

The term "heterocyclearylcarbonyl," as used herein, refers to a heterocyclearyl group, as defined herein, appended to the parent molecular moiety through a carbonyl group, as defined herein. Representative examples of heterocyclearylcarbonyl include, but are not limited to, 4-(pyridin-3-yl)benzoyl and 4-(pyrimidin-2-yl)benzoyl.

The term "heterocyclearylsulfonyl," as used herein, refers to a heterocyclearyl group, as defined herein, appended to the parent molecular moiety through a sulfonyl group, as defined herein. Representative examples of heterocyclearylsulfonyl include, but are not limited to, (4-(pyridin-3-yl)phenyl)sulfonyl and (4-(pyrimidin-2-yl)phenyl)sulfonyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, 2-furoyl, morpholin-1-ylcarbonyl, pyridin-3-ylcarbonyl, pyrrolidin-1-ylcarbonyl, and quinolin-3-ylcarbonyl.

The term "heterocyclecarbonylaryl," as used herein, refers to a heterocyclecarbonyl, as defined herein, appended to the parent molecular moiety through an aryl group, as defined herein. Representative examples of heterocyclecarbonylaryl include, but are not limited to, 4-(2-furoyl)phenyl, 4-(1-pyrrolidinylcarbonyl)phenyl, 4-(1-piperidinylcarbonyl)phenyl, 4-(4-morpholinylcarbonyl)phenyl, 4-(1-azetidinylcarbonyl)phenyl, 4-(1-piperazinylcarbonyl)phenyl and 4-(3-pyridinylcarbonyl)phenyl.

The term "heterocyclecarbonylheterocycle," as used herein, refers to a heterocyclecarbonyl, as defined herein, appended to the parent molecular moiety through a heterocycle group, as defined herein. Representative examples of heterocyclecarbonylheterocycle include, but are not limited to, 4-(2-furoyl)-1-piperazinyl, 4-(1-pyrrolidinylcarbonyl)-1-piperazinyl, 4-(1-piperidinylcarbonyl)-1-piperazinyl, 4-(4-morpholinylcarbonyl)-1-piperazinyl, 4-(1-azetidinylcarbonyl)-1-piperazinyl, 4-(1-piperazinylcarbonyl)-1-piperazinyl and 4-(3-pyridinylcarbonyl)-1-piperazinyl.

The term "heterocycleheterocycle," as used herein, refers to a heterocycle group, as defined herein, appended to the parent molecular moiety through another heterocycle group, as defined herein. Representative examples of heterocycleheterocycle include, but are not limited to, 2-(pyridin-3-yl)thiazo-4-yl and 2-(pyrimidin-2-yl)thiazo-4-yl.

The term "heterocycleheterocyclecarbonyl," as used herein, refers to a heterocycleheterocycle group, as defined herein, appended to the parent molecular moiety through a carbonyl group, as defined herein. Representative examples of heterocycleheterocyclecarbonyl include, but are not limited to, (2-(pyridin-3-yl)thiazo-4-yl)carbonyl and (2-(pyrimidin-2-yl)thiazo-4-yl)carbonyl.

The term "heterocycleheterocyclesulfonyl," as used herein, refers to a heterocycleheterocycle group, as defined herein, appended to the parent molecular moiety through a sulfonyl group, as defined herein. Representative examples of eterocycleheterocyclesulfonyl include, but are not limited to, (2-(pyridin-3-yl)thiazo-4-yl)sulfonyl and (2-(pyrimidin-2-yl)thiazo-4-yl)sulfonyl.

The term "heterocycleoxy," as used herein, refers to a heterocycle group, as defined herein, appended to the parent molecular moiety through an oxy moiety, as defined herein. Representative examples of heterocycleoxy include, but are not limited to, pyrid-3-yloxy and quinolin-3-yloxy.

The term "heterocycleoxyalkyl," as used herein, refers to a heterocycleoxy group, as defined herein, appended to the parent molecular moiety through an alkyl group, as defined herein. Representative examples of heterocycleoxyalkyl include, but are not limited to, pyrid-3-yloxymethyl and 2-quinolin-3-yloxyethyl.

The term "heterocycleoxyalkylcarbonyl," as used herein, refers to a heterocycleoxyalkyl group, as defined herein, appended to the parent molecular moiety through a carbonyl group, as defined herein. Representative examples of heterocycleoxyalkylcarbonyl include, but are not limited to, (pyridin-3-yloxymethyl)carbonyl and (2-(quinolin-3-yloxy)ethyl)carbonyl.

The term "heterocycleoxyaryl," as used herein, refers to a heterocycleoxy group, as defined herein, appended to the parent molecular moiety through an aryl group, as defined herein. Representative examples of heterocycleoxyaryl include, but are not limited to, 4-(pyridin-3-yloxy)phenyl and 4-(quinolin-3-yloxy)phenyl.

The term "heterocycleoxyarylcarbonyl," as used herein, refers to a heterocycleoxyaryl group, as defined herein, appended to the parent molecular moiety through a carbonyl group, as defined herein. Representative examples of heterocycleoxyarylcarbonyl include, but are not limited to, 4-(pyridin-3-yloxy)benzoyl and 4-(quinolin-3-yloxy)benzoyl.

The term "heterocycleoxyarylsulfonyl," as used herein, refers to a heterocycleoxyaryl group, as defined herein, appended to the parent molecular moiety through a sulfonyl group, as defined herein. Representative examples of heterocycleoxyarylsulfonyl include, but are not limited to, (4-(pyridin-3-yloxy)phenyl)sulfonyl and (4-(quinolin-3-yloxy)phenyl)sulfonyl.

The term "heterocyclesulfonyl," as used herein, refers to a heterocycle group, as defined herein, appended to the parent molecular moiety through a sulfonyl group, as defined herein. Representative examples of heterocyclesulfonyl include, but are not limited to, (pyridin-3-yl)sulfonyl and (quinolin-8-yl)sulfonyl.

The term "heterocyclethio," as used herein, refers to a heterocycle group, as defined herein, appended to the parent molecular moiety through a thio moiety, as defined herein. Representative examples of heterocyclethio include, but are not limited to, pyrid-3-ylsulfanyl and quinolin-3-ylsulfanyl.

The term "heterocyclethioalkyl," as used herein, refers to a heterocyclethio group, as defined herein, appended to the parent molecular moiety through an alkyl group, as defined herein. Representative examples of heterocyclethioalkyl include, but are not limited to, pyrid-3-ylsulfanylmethyl, (4-methylpyrimidin-2-yl)sulfanylmethyl, and 2-(quinolin-3-ylsulfanyl)ethyl.

The term "heterocyclethioalkylcarbonyl," as used herein, refers to a heterocyclethioalkyl group, as defined herein, appended to the parent molecular moiety through a carbonyl group, as defined herein. Representative examples of heterocyclethioalkylcarbonyl include, but are not limited to, (pyrid-3-ylsulfanyl)acetyl, ((4-methylpyrimidin-2-yl)sulfanyl)acetyl, and (quinolin-3-ylsulfanyl)acetyl.

The term "hydroxy," as used herein, refers to an —OH group.

The term "hydroxyalkyl," as used herein, refers to one or two hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl and 2-ethyl-4-hydroxyheptyl.

The term "lower alkyl," as used herein, is a subset of alkyl as defined herein and refers to a straight or branched chain hydrocarbon group containing from 1 to 4 carbon atoms.

Examples of lower alkyl are methyl, ethyl, n-propyl, isopropyl, n-butyl, iso-butyl, sec-butyl, and tert-butyl.

The term "mercapto," as used herein, refers to a —SH group.

The term "nitro," as used herein, refers to a —NO$_2$ group.

The term "oxo," as used herein, refers to a =O moiety.

The term "oxy," as used herein, refers to a —O— moiety.

The term "phosphono," as used herein, refers to a —P(O)(OR$_D$)$_2$ group wherein R$_D$ is selected from hydrogen and alkyl, as defined herein. Representative examples of phosphono include, but are not limited to, dimethoxyphosphoryl and diethoxyphosphoryl.

The term "sulfinyl," as used herein, refers to a —S(O)— group.

The term "sulfono," as used herein, refers to a —S(O)$_2$(OR$_E$) group wherein R$_E$ is selected from alkyl, aryl, and arylalkyl, as defined herein. Representative examples of sulfono include, but are not limited to, methoxysulfonyl, ethoxysulfonyl, (benzyloxy)sulfonyl and phenoxysulfonyl.

The term "sulfonyl," as used herein, refers to a —SO$_2$— group.

The term "thio," as used herein, refers to a —S— moiety.

Preferred compounds of formula I include, but are not limited to:

N-{(3R)-1-[3-(4-acetylphenoxy)propyl]pyrrolidinyl}cyclopropanecarboxamide;
N-{(3R)-1-[3-(4-acetylphenoxy)propyl]pyrrolidinyl}-2-[(4-methyl-2-pyrimidinyl)sulfanyl]acetamide;
N-{(3R)-1-[3-(4-acetylphenoxy)propyl]pyrrolidinyl}nicotinamide;
N-{(3R)-1-[3-(4-acetylphenoxy)propyl]pyrrolidinyl}-2-(3-pyridinyl)-1,3carboxamide;
N-{(3R)-1-[3-(4-acetylphenoxy)propyl]pyrrolidinyl}-4-cyanobenzenesulfonamide;
N-{(3R)-1-[3-(4-acetylphenoxy)propyl]pyrrolidinyl}-2-propanesulfonamide;
1-(4-{3-[(3R)-3-aminopyrrolidinyl]propoxy}phenyl)-1-propanone;
(5R)-3-{(3R)-1-[3-(4-acetylphenoxy)propyl]pyrrolidinyl}-5-methyl-2,4-imidazolidinedione;
(5S)-3-{(3R)-1-[3-(4-acetylphenoxy)propyl]pyrrolidinyl}-5-methyl-2,4-imidazolidinedione;
(5R)-3-{(3R)-1-[3-(4-acetylphenoxy)propyl]pyrrolidinyl}-5-isopropyl-2,4-imidazolidinedione;
4-cyano-N-((3R)-1-{3-[4-(cyclopropylcarbonyl)phenoxy]propyl}pyrrolidinyl)benzenesulfonamide;
N-((3R)-1-{3-[4-(cyclopropylcarbonyl)phenoxy]propyl}pyrrolidinyl)-2-propanesulfonamide;
N-((3R)-1-{3-[4-(cyclopropylcarbonyl)phenoxy]propyl}pyrrolidinyl)-2-(3-pyridinyl)-1,3-thiazole-4-carboxamide;
N-{(3R)-1-[3-(4-acetylphenoxy)propyl]pyrrolidinyl}-4-cyanobenzamide;
N-((3R)-1-{3-[(4'-cyano [1,1'-biphenyl]-4-yl)oxy]propyl}pyrrolidinyl)benzenesulfonamide;
4-bromo-N-((3R)-1-{3-[(4'-cyano [1,1'-biphenyl]-4-yl)oxy]propyl}pyrrolidinyl)benzenesulfonamide;
N-((3R)-1-{3-[(4'-cyano[1,1'-biphenyl]-4-yl)oxy]propyl}pyrrolidinyl)-4-fluorobenzenesulfonamide;
4-chloro-N-((3R)-1-{3-[(4'-cyano[1,1'-biphenyl]-4-yl)oxy]propyl}pyrrolidinyl)benzenesulfonamide;
N-(4-{[((3R)-1-{3-[(4'-cyano[1,1'-biphenyl]-4-yl)oxy]propyl}pyrrolidinyl)amino]sulfonyl}phenyl)acetamide;
N-((3R)-1-{3-[(4'-cyano[1,1'-biphenyl]-4-yl)oxy]propyl}pyrrolidinyl)-4-methoxybenzenesulfonamide;
4-tert-butyl-N-((3R)-1-{3-[(4'-cyano[1,1'-biphenyl]-4-yl)oxy]propyl}pyrrolidinyl)benzenesulfonamide;
N-((3R)-1-{3-[(4'-cyano[1,1'-biphenyl]-4-yl)oxy]propyl}pyrrolidinyl)-4-methylbenzenesulfonamide;
N-((3R)-1-{3-[(4'-cyano[1,1'-biphenyl]-4-yl)oxy]propyl}pyrrolidinyl)-4-(trifluoromethyl)benzenesulfonamide;
N-((3R)-1-{3-[(4'-cyano[1,1'-biphenyl]-4-yl)oxy]propyl}pyrrolidinyl)-2,5-dimethoxybenzenesulfonamide;
N-((3R)-1-{3-[(4'-cyano[1,1'-biphenyl]-4-yl)oxy]propyl}pyrrolidinyl)-2-methylbenzenesulfonamide;
3-chloro-N-((3R)-1-{3-[(4'-cyano[1,1'-biphenyl]-4-yl)oxy]propyl}pyrrolidinyl)-4-fluorobenzenesulfonamide;
N-((3R)-1-{3-[(4'-cyano[1,1'-biphenyl]-4-yl)oxy]propyl}pyrrolidinyl)-4-ethylbenzenesulfonamide;
N-((3R)-1-{3-[(4'-cyano[1,1'-biphenyl]-4-yl)oxy]propyl}pyrrolidinyl)-4-isopropylbenzenesulfonamide;
N-((3R)-1-{3-[(4'-cyano[1,1'-biphenyl]-4-yl)oxy]propyl}pyrrolidinyl)-2-fluorobenzenesulfonamide;
2-chloro-N-((3R)-1-{3-[(4'-cyano[1,1'-biphenyl]-4-yl)oxy]propyl}pyrrolidinyl)benzenesulfonamide;
3-chloro-N-((3R)-1-{3-[(4'-cyano[1,1'-biphenyl]-4-yl)oxy]propyl}pyrrolidinyl)benzenesulfonamide;
3,5-dichloro-N-((3R)-1-{3-[(4'-cyano[1,1'-biphenyl]-4-yl)oxy]propyl}pyrrolidinyl)benzenesulfonamide;
4-cyano-N-((3R)-1-{3-[(4'-cyano[1,1'-biphenyl]-4-yl)oxy]propyl}pyrrolidinyl)benzenesulfonamide;
3-cyano-N-((3R)-1-{3-[(4'-cyano[1,1'-biphenyl]-4-yl)oxy]propyl}pyrrolidinyl)benzenesulfonamide;
N-((3R)-1-{3-[(4'-cyano[1,1'-biphenyl]-4-yl)oxy]propyl}pyrrolidinyl)-1-methyl-1H-imidazole-4-sulfonamide;
N-((3R)-1-{3-[(4'-cyano[1,1'-biphenyl]-4-yl)oxy]propyl}pyrrolidinyl)-2-thiophenesulfonamide;
5-chloro-N-((3R)-1-{3-[(4'-cyano[1,1'-biphenyl]-4-yl)oxy]propyl}pyrrolidinyl)-3methyl-1-benzothiophene-2-sulfonamide;
N-((3R)-1-{3-[(4'-cyano[1,1'-biphenyl]-4-yl)oxy]propyl}pyrrolidinyl)-3,5-bis(trifluoromethyl)benzenesulfonamide;
N-(5-{[((3R)-1-{3-[(4'-cyano[1,1'-biphenyl]-4-yl)oxy]propyl}pyrrolidinyl)amino]sulfonyl}-4-methyl-1,3-thiazol-2-yl)acetamide;
N-((3R)-1-{3-[(4'-cyano[1,1'-biphenyl]-4-yl)oxy]propyl}pyrrolidinyl)-8-quinolinesulfonamide;
4-butoxy-N-((3R)-1-{3-[(4'-cyano[1,1'-biphenyl]-4-yl)oxy]propyl}pyrrolidinyl)benzenesulfonamide;
N-((3R)-1-{3-[(4'-cyano[1,1'-biphenyl]-4-yl)oxy]propyl}pyrrolidinyl)-3,4-dimethoxybenzenesulfonamide;
3-chloro-N-((3R)-1-{3-[(4'-cyano[1,1'-biphenyl]-4-yl)oxy]propyl}pyrrolidinyl)-4-methylbenzenesulfonamide;
N-((3R)-1-{3-[(4'-cyano[1,1'-biphenyl]-4-yl)oxy]propyl}pyrrolidinyl-2-phenylethenesulfonamide;
N-((3R)-1-{3-[(4'-cyano[1,1'-biphenyl]-4-yl)oxy]propyl}pyrrolidinyl)-2-(trifluoromethoxy)benzenesulfonamide;
2-cyano-N-((3R)-1-{3-[(4'-cyano[1,1'-biphenyl]-4-yl)oxy]propyl}pyrrolidinyl)benzenesulfonamide;
N-((3R)-1-{3-[(4'-cyano[1,1'-biphenyl]-4-yl)oxy]propyl}pyrrolidinyl)-3-methylbenzenesulfonamide;
N-((3R)-1-{3-[(4'-cyano[1,1'-biphenyl]-4-yl)oxy]propyl}pyrrolidinyl)-4-(trifluoromethyl)benzenesulfonamide;
N-((3R)-1-{3-[(4'-cyano[1,1'-biphenyl]-4-yl)oxy]propyl}pyrrolidinyl)-3-fluorobenzenesulfonamide;
N-((3R)-1-{3-[(4'-cyano[1,1'-biphenyl]-4-yl)oxy]propyl}pyrrolidinyl)-4-(trifluoromethoxy)benzenesulfonamide;
N-((3R)-1-{3-[(4'-cyano[1,1'-biphenyl]-4-yl)oxy]propyl}pyrrolidinyl)-2,4-difluorobenzenesulfonamide;

N-((3R)-1-{3-[(4'-cyano[1,1'-biphenyl]-4-yl)oxy]
propyl}pyrrolidinyl)-7-isoquinolinesulfonamide;
N-(2-chloro-4-{[((3R)-1-{3-[(4'-cyano[1,1'-biphenyl]-4-yl)
oxy]propyl}pyrrolidinyl)amino]sulfonyl}phenyl)
acetamide;
3,4-dichloro-N-((3R)-1-{3-[(4'-cyano[1,1'-biphenyl]-4-yl)
oxy]propyl}pyrrolidinyl)benzenesulfonamide;
N-((3R)-1-{3-[4-(cyclopropylcarbonyl)phenoxy]
propyl}pyrrolidinyl)benzenesulfonamide;
4-bromo-N-((3R)-1-{3-[4-(cyclopropylcarbonyl)phenoxy]
propyl}pyrrolidinyl)benzenesulfonamide;
N-((3R)-1-{3-[4-(cyclopropylcarbonyl)phenoxy]
propyl}pyrrolidinyl)-4-fluorobenzenesulfonamide;
4-chloro-N-((3R)-1-{3-[4-(cyclopropylcarbonyl)phenoxy]
propyl}pyrrolidinyl)benzenesulfonamide;
N-((3R)-1-{3-[4-(cyclopropylcarbonyl)phenoxy]
propyl}pyrrolidinyl)-4-methoxybenzenesulfonamide;
4-tert-butyl-N-((3R)-1-{3-[4-(cyclopropylcarbonyl)
phenoxy]propyl}pyrrolidinyl)benzenesulfonamide;
N-((3R)-1-{3-[4-(cyclopropylcarbonyl)phenoxy]
propyl}pyrrolidinyl)-4-methylbenzenesulfonamide;
N-((3R)-1-{3-[4-(cyclopropylcarbonyl)phenoxy]
propyl}pyrrolidinyl)-3-(trifluoromethyl)
benzenesulfonamide;
N-((3R)-1-{3-[4-(cyclopropylcarbonyl)phenoxy]
propyl}pyrrolidinyl)-2,5-dimethoxybenzenesulfonamide;
N-((3R)-1-{3-[4-(cyclopropylcarbonyl)phenoxy]
propyl}pyrrolidinyl)-2-methylbenzenesulfonamide;
3-chloro-N-((3R)-1-{3-[4-(cyclopropylcarbonyl)phenoxy]
propyl}pyrrolidiynyl)-4-fluorobenzenesulfonamide;
N-((3R)-1-{3-[4-(cyclopropylcarbonyl)phenoxy]
propyl}pyrrolidinyl)-4-ethylbenzenesulfonamide;
N-((3R)-1-{3-[4-(cyclopropylcarbonyl)phenoxy]
propyl}pyrrolidinyl)-4-isopropylbenzenesulfonamide;
N-((3R)-1-{3-[4-(cyclopropylcarbonyl)phenoxy]
propyl}pyrrolidinyl)-2-fluorobenzenesulfonamide;
2-chloro-N-((3R)-1-{3-[4-(cyclopropylcarbonyl)phenoxy]
propyl}pyrrolidinyl)benzenesulfonamide;
3-chloro-N-((3R)-1-{3-[4-(cyclopropylcarbonyl)phenoxy]
propyl}pyrrolidinyl)benzenesulfonamide;
3-cyano-N-((3R)-1-{3-[4-(cyclopropylcarbonyl)phenoxy]
propyl}pyrrolidinyl)benzenesulfonamide;
N-{(3R)-1-[3-(4-acetylphenoxy)propyl]pyrrolidinyl}-3-
fluorobenzenesulfonamide;
N-{(3R)-1-[3-(4-acetylphenoxy)propyl]pyrrolidinyl}-4-
(trifluoromethoxy)benzenesulfonamide;
N-{(3R)-1-[3-(4-acetylphenoxy)propyl]pyrrolidinyl}-2,4-
difluorobenzenesulfonamide;
N-{(3R)-1-[3-(4-acetylphenoxy)propyl]pyrrolidinyl}-5-
isoquinolinesulfonamide;
N-{4-[({(3R)-1-[3-(4-acetylphenoxy)propyl]
pyrrolidinyl}amino)sulfonyl]-2-chlorophenyl}acetamide;
N-{(3R)-1-[3-(4-acetylphenoxy)propyl]pyrrolidinyl}-3,4-
dichlorobenzenesulfonamide;
N-{(3R)-1-[3-(4-acetylphenoxy)propyl]pyrrolidinyl}-1-[3-
chloro-5-(trifluorometyl)-2-pyridinyl]-1H-pyrrole-2-
sulfonamide;
N-{(3R)-1-[3-(4-acetylphenoxy)propyl]pyrrolidinyl}-4-{
[3-chloro-5-(trifluoromethyl)-2-pyridinyl]
oxy}benzenesulfonamide;
N-((3R)-1-{3-[4-(cyclopropylcarbonyl)phenoxy]
propyl}pyrrolidinyl)-1-methyl-1H-imidazole-4-
sulfonamide;
N-((3R)-1-{3-[4-(cyclopropylcarbonyl)phenoxy]
propyl}pyrrolidinyl)-2-thiophenesulfonamide;
5-chloro-N-((3R)-1-{3-[4-(cyclopropylcarbonyl)phenoxy]
propyl}pyrrolidinyl)-3-methyl-1-benzothiophene-2-
sulfonamide;
N-((3R)-1-{3-[4-(cyclopropylcarbonyl)phenoxy]
propyl}pyrrolidinyl)-3,5-bis(trifluoromethyl)
benzenesulfonamide;
N-((3R)-1-{3-[4-(cyclopropylcarbonyl)phenoxy]
propyl}pyrrolidinyl)-8-quinolinesulfonamide;
4-butoxy-N-((3R)-1-{3-[4-(cyclopropylcarbonyl)phenoxy]
propyl}pyrrolidinyl)benzenesulfonamide;
N-((3R)-1-{3-[4-(cyclopropylcarbonyl)phenoxy]
propyl}pyrrolidinyl)-3,4-dimethoxybenzenesulfonamide;
3-chloro-N-((3R)-1-{3-[4-(cyclopropylcarbonyl)phenoxy]
propyl}pyrrolidinyl)-4-methylbenzenesulfonamide;
N-((3R)-1-{3-[4-(cyclopropylcarbonyl)phenoxy]
propyl}pyrrolidinyl)-2-phenylethenesulfonamide;
N-((3R)-1-{3-[4-(cyclopropylcarbonyl)phenoxy]
propyl}pyrrolidinyl)-2-(trifluoromethoxy)
benzenesulfonamide;
2-cyano-N-((3R)-1-{3-[4-(cyclopropylcarbonyl)phenoxy]
propyl}pyrrolidinyl)benzenesulfonamide;
N-((3R) 1-{3-[4-(cyclopropylcarbonyl)phenoxy]
propyl}pyrrolidinyl)-3-methylbenzenesulfonamide;
N-((3R)-1-{3-[4-(cyclopropylcarbonyl)phenoxy]
propyl}pyrrolidinyl)-4-(trifluoromethyl)
benzenesulfonamide;
N-((3R)-1-{3-[4-(cyclopropylcarbonyl)phenoxy]
propyl}pyrrolidinyl)-3-fluorobenzenesulfonamide;
N-((3R)-1-{3-[4-(cyclopropylcarbonyl)phenoxy]
propyl}pyrrolidinyl)-4-(trifluoromethoxy)
benzenesulfonamide;
N-((3R)-1-{3-[4-(cyclopropylcarbonyl)phenoxy]
propyl}pyrrolidinyl)-8-isoquinolinesulfonamide;
N-(2-chloro-4-{[((3R)-1-{3-[4-(cyclopropylcarbonyl)
phenoxy]propyl}pyrrolidinyl)amino]sulfonyl}phenyl)
acetamide;
3,4-dichloro-N-((3R)-1-{3-[4-(cyclopropylcarbonyl)
phenoxy]propyl}pyrrolidinyl)benzenesulfonamide;
tert-butyl 1-{3-[(4'-cyano[1,1'-biphenyl]-4-yl)oxy]propyl}-
3-pyrrolidinylcarbamate;
4'-{3-[(3R)-3-aminopyrrolidinyl]propoxy}[1,1'-biphenyl]-
4-carbonitrile;
tert-butyl (3S)-1-{2-[(4'-cyano[1,1'-biphenyl]-4-yl)oxy]
ethyl}pyrrolidinylcarbamate;
4-methoxy-N-((3R)-1-{3-[4-(2-pyridinyl)phenoxy]
propyl}pyrrolidinyl)benzenesulfonamide;
4-isopropyl-N-((3R)-1-{3-[4-(2-pyridinyl)phenoxy]
propyl}pyrrolidinyl)benzenesulfonamide;
4-cyano-N-((3R)-1-{3-[4-(2-pyridinyl)phenoxy]
propyl}pyrrolidinyl)benzenesulfonamide;
3-cyano-N-((3R)-1-{3-[4-(2-pyridinyl)phenoxy]
propyl}pyrrolidinyl)benzenesulfonamide;
1-methyl-N-((3R)-1-{3-[4-(2-pyridinyl)phenoxy]
propyl}pyrrolidinyl)-1H-imidazole-4-sulfonamide;
3,4-dimethoxy-N-((3R)-1-{3-[4-(2-pyridinyl)phenoxy]
propyl}pyrrolidinyl)benzenesulfonamide;
N-(2-chloro-4-{[((3R)-1-{3-[4-(2-pyridinyl)phenoxy]
propyl}pyrrolidinyl)amino]sulfonyl}phenyl)acetamide;
4'-{3-[(3R)-3-(dimethylamino)pyrrolidinyl]propoxy}[1,1'-
biphenyl]-4-carbonitrile;
tert-butyl (3R)-1-{3-[(4'-cyano[1,1'-biphenyl]-4-yl)oxy]
propyl}pyrrolidinyl(methyl)carbamate;
4'-{3-[(3R)-3-(methylamino)pyrrolidinyl]propoxy}[1,1'-
biphenyl]-4-carbonitrile;
N-((3R)-1-{3-[(4'-cyano[1,1'-biphenyl]-4-yl)oxy]
propyl}pyrrolidinyl)-N-methylacetamide;
N-((3R)-1-{3-[(4'-cyano[1,1'-biphenyl]-4-yl)oxy]
propyl}pyrrolidinyl)-N,3,3-trimethylbutanamide;
methyl (3R)-1-{3-[(4'-cyano[1,1'-biphenyl]-4-yl)oxy]
propyl}pyrrolidinyl(methyl)carbamate;

tert-pentyl (3R)-1-{3-[(4'-cyano[1,1'-biphenyl]-4-yl)oxy]propyl}pyrrolidinyl(methyl)carbamate;
N-((3R)-1-{3-[(4'-cyano[1,1'-biphenyl]-4-yl)oxy]propyl}pyrrolidinyl)-N,N',N'-trimethylurea;
N-((3R)-1-{3-[(4'-cyano[1,1'-biphenyl]-4-yl)oxy]propyl}pyrrolidinyl)-N-methyl-4-pyrrolidinecarboxamide;
N'-tert-butyl-N-((3R)-1-{3-[(4'-cyano[1,1'-biphenyl]-4-yl)oxy]propyl}pyrrolidinyl)-N-methylurea;
N-((3R)-1-{3-[(4'-cyano[1,1'-biphenyl]-4-yl)oxy]propyl}pyrrolidinyl)-N-methyl-4-morpholinecarboxamide;
N-((3R)-1-{3-[(4'-cyano[1,1'-biphenyl]-4-yl)oxy]propyl}pyrrolidinyl)-4-fluoro-N-methylbenzamide;
4-cyano-N-((3R)-1-{3-[(4'-cyano[1,1'-biphenyl]-4-yl)oxy]propyl}pyrrolidinyl)-N-methylbenzamide;
N-((3R)-1-{3-[(4'-cyano[1,1'-biphenyl]-4-yl)oxy]propyl}pyrrolidinyl)-N-methylnicotinamide;
N-((3R)-1-{3-[(4'-cyano[1,1'-biphenyl]-4-yl)oxy]propyl}pyrrolidinyl)-N-metyl-2-furamide;
N-((3R)-1-{3-[(4'-cyano[1,1'-biphenyl]-4-yl)oxy]propyl}pyrrolidinyl)-N-methyl-3-(3-pyridinyl)-1,3-thiazole-4-carboxamide;
N-[(3R)-1-[3-[(4'-cyano[1,1'-biphenyl]-4-yl)oxy]propyl]pyrrolidinyl]-N,N',N'-trimethyl-sulfamide;
N-((3R)-1-{3-[(4'-cyano[1,1'-biphenyl]-4-yl)oxy]propyl}pyrrolidinyl)-3-flouro-N-methylbenzenesulfonamide;
4-cyano-N-((3R)-1-{3-[(4'-cyano[1,1'-biphenyl]-4-yl)oxy]propyl}pyrrolidinyl)-N-methylbenzenesulfonamide;
N-((3R)-1-{3-[(4'-cyano[1,1'-biphenyl]-4-yl)oxy]propyl}pyrrolidinyl)-4-isopropyl-N-methylbenzenesulfonamide;
N-((3R)-1-{3-[(4'-cyano[1,1'-biphenyl]-4-yl)oxy]propyl}pyrrolidinyl)-N-methyl-4-(methylsulfonyl)benzenesulfonamide;
N-((3R)-1-{3-[(4'-cyano[1,1'-biphenyl]-4-yl)oxy]propyl}pyrrolidinyl)-4-flouro-N-(4-fluorobenzoyl)benzamide;
N-((3R)-1-{3-[(4'-cyano[1,1'-biphenyl]-4-yl)oxy]propyl}pyrrolidinyl)acetamide;
N-((3R)-1-{3-[(4'-cyano[1,1'-biphenyl]-4-yl)oxy]propyl}pyrrolidinyl)-3,3-dimethylbutanamide;
allyl (3R)-1-{3-[(4'-cyano[1,1'-biphenyl]-4-yl)oxy]propyl}pyrrolidinyl
methyl (3R)-1-{3-[(4'-cyano[1,1'-biphenyl]-4-yl)oxy]propyl}pyrrolidinylcarbamate;
tert-pentyl (3R)-1-{3-[(4'-cyano[1,1'-biphenyl]-4-yl)oxy]propyl}pyrrolidinylcarbamate;
N'-((3R)-1-{3-[(4'-cyano[1,1'-biphenyl]-4-yl)oxy]propyl}pyrrolidinyl)-N,N-15 dimethylurea;
N-((3R)-1-{3-[(4'-cyano[1,1'-biphenyl]-4-yl)oxy]propyl}pyrrolidinyl)-1-pyrrolidinecarboxamide;
N-(tert-butyl)-N'-((3R)-1-{3-[(4'-cyano[1,1'-biphenyl]-4-yl)oxy]propyl}pyrrolidinyl)urea;
N-((3R)-1-{3-[(4'-cyano[1,1'-biphenyl]-4-yl)oxy]propyl}pyrrolidinyl)-4-morpholinecarboxamide;
N-((3R)-1-{3-[(4'-cyano[1,1'-biphenyl]-4-yl)oxy]propyl}pyrrolidinyl)-4-fluorobenzamide;
4-cyano-N-((3R)-1-{3-[(4'-cyano[1,1'-biphenyl]-4-yl)oxy]propyl}pyrrolidinyl)benzamide;
N-((3R)-1-{3-[(4'-cyano[1,1'-biphenyl]-4-yl)oxy]propyl}pyrrolidinyl)nicotinamide;
N-((3R)-1-{3-[(4'-cyano[1,1'-biphenyl]-4-yl)oxy]propyl}pyrrolidinyl)-2-furamide;
N-((3R)-1-{3-[(4'-cyano[1,1'-biphenyl]-4-yl)oxy]propyl}pyrrolidinyl)-2-(3-pyridinyl)-1,3-thiazole-4-carboxamide;
N-((3R)-1-{3-[(4'-cyano[1,1'-biphenyl]-4-yl)oxy]propyl}pyrrolidinyl)-2-propanesulfonamide;
N'-((3R)-1-{3-[(4'-cyano[1,1'-biphenyl]-4-yl)oxy]propyl}pyrrolidinyl)-N,N-dimethylsulfamide;
N-((3R)-1-{3-[(4'-cyano[1,1'-biphenyl]-4-yl)oxy]propyl}pyrrolidinyl)-4-(methylsulfonyl)benzenesulfonamide;
N-((3R)-1-{3-[(4'-cyano[1,1'-biphenyl]-4-yl)oxy]propyl}pyrrolidinyl)-N-(3,3-dimethylbutanoyl)-3,3-dimethylbutanamide;
N'-((3R)-1-{3-[(4'-cyano[1,1'-biphenyl]-4-yl)oxy]propyl}pyrrolidinyl)-N'-(dimethylaminocarbonyl)-N,N-dimethylurea;
N-((3R)-1-{3-[(4'-cyano[1,1'-biphenyl]-4-yl)oxy]propyl}pyrrolidinyl)-N-(1-pyrrolidinylcarbonyl)-1-pyrrolidinecarboxamide;
N-((3R)-1-{3-[(4'-cyano[1,1'-biphenyl]-4-yl)oxy]propyl}pyrrolidinyl)-N-(4-morpholinylcarbonyl)-4-morpholinecarboxamide;
cyclopropyl {4-[3-(3-hydroxy-1-pyrrolidinyl)propoxy]phenyl}methanone;
cyclopropyl(4-{3-[(3R)-3-hydroxypyrrolidinyl]propoxy}phenyl)methanone;
4'-{3-[(3R)-3-hydroxypyrrolidinyl]propoxy}[1,1'-biphenyl]-4-carbonitrile;
4'-[3-(3-oxo-1-pyrrolidinyl)propoxy][1,1'-biphenyl]-4-carbonitrile;
4'-{3-[(3S)-3-hydroxypyrrolidinyl]propoxy}[1,1'-biphenyl]-4-carbonitrile;
4'-[3-(3-hydroxy-3-methyl-1-pyrrolidinyl)propoxy][1,1'-biphenyl]-4-carbonitrile;
4'-[3-(3-hydroxy-3-isopropyl-1-pyrrolidinyl)propoxy][1,1'-biphenyl]-4-carbonitrile;
4'-{3-[(3R)-3-hydroxy-3-methylpyrrolidinyl]propoxy}[1,1'-biphenyl]-4-carbonitrile;
N,N-dimethyl-N-[(3R)-1-(3-{[4'-(1-pyrrolidinylcarbonyl)[1,1'-biphenyl]-4-yl]oxy}propyl)pyrrolidinyl]amine;
N,N-dimethyl-N-[(3S)-1-(3-{[4'-(1-pyrrolidinylcarbonyl)[1,1'-biphenyl]-4-yl]oxy}propyl)pyrrolidinyl]amine;
(3R)-1-(3-{[4'-(1-pyrrolidinylcarbonyl)[1,1'-biphenyl]-4-yl]oxy}propyl)-3-pyrrolidinol;
N,N-dimethyl-N-[(3R)-1-(3-{4-[4-(1-pyrrolidinylcarbonyl)-1-piperazinyl]phenoxy}propyl)pyrrolidinyl]amine;
N,N-dimethyl-N-[(3S)-1-(3-{4-[4-(1-pyrrolidinylcarbonyl)-1-piperazinyl]phenoxy}propyl)pyrrolidinyl]amine and pharmaceutically acceptable salts, esters, amides, or prodrugs thereof.

Abbreviations

Abbreviations which have been used in the descriptions of the schemes and the examples that follow are: AcOH for acetic acid; $BF_3OEt_2$ for boron trifluoride diethyl ether complex; Boc for tert-butoxycarbonyl; $(Boc)_2O$ for di-tert-butyl dicarbonate; n-BuLi for n-butyllithium; CDI for 1,1'-carbonyldiimidazole; DCC for 1,3-dicyclohexylcarbodiimide; DMAP for 4-dimethylaminopyridine; DMF for N,N-dimethylformamide; DMSO for dimethyl sulfoxide; EDCI or EDC for 1-ethyl-3-[3-(dimethylamino)propyl]-carbodiimide hydrochloride; EtOAc for ethyl acetate; EtOH for ethanol; HOBT for 1-hydroxybenzotriazole hydrate; LAH for lithium aluminum hydride; LDA for lithium diisopropylamide; MeOH for methanol; pyr for pyridine; TFA for trifluoroacetic acid; and THF for tetrahydrofuran.

Preparation of Compounds of the Invention

The compounds and processes of the present invention will be better understood in connection with the following synthetic schemes and methods which illustrate a means by which the compounds of the invention can be prepared.

The compounds of this invention can be prepared by a variety of synthetic routes. Representative procedures are shown in Schemes 1–7.

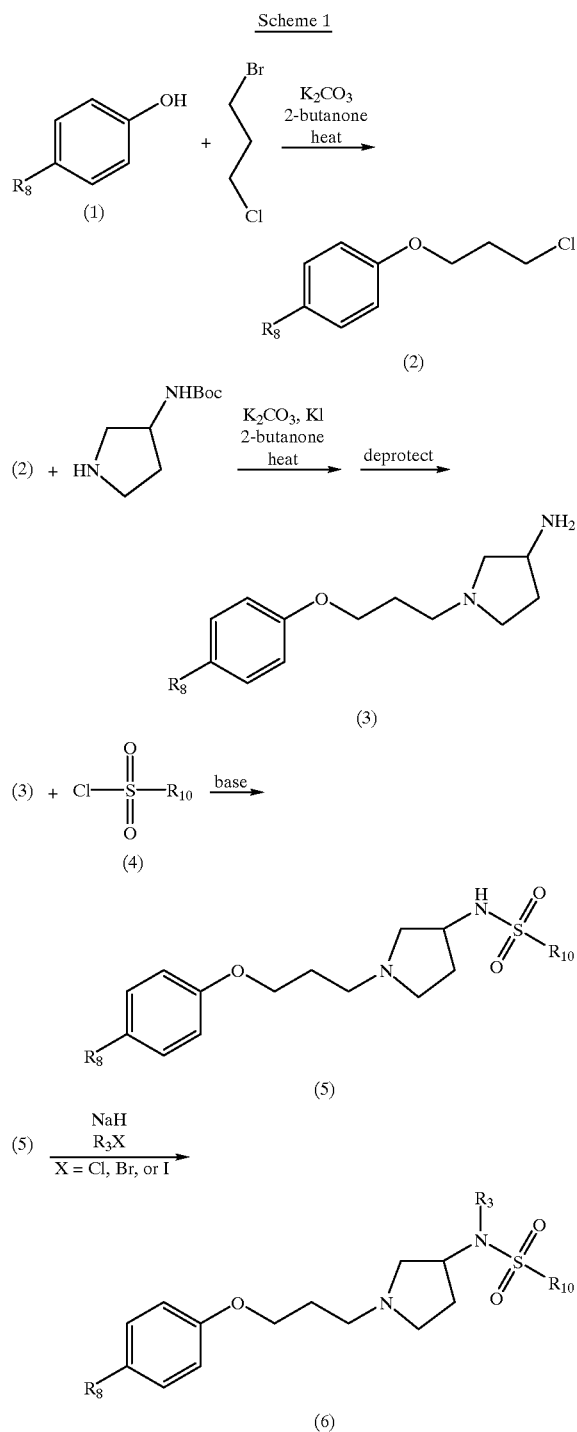

Sulfonamides of general formula (6), wherein $R_3$ and $R_8$ are as defined in formula I, and $R_{10}$ is selected from alkenyl, alkyl, alkynyl, amino, aryl, arylalkenyl, arylalkyl, arylaryl, arylheterocyle, aryloxyaryl, cycloalkyl, cycloalkylalkyl, heterocyclealkyl, heterocyclearyl, heterocycleheterocycle, heterocycleoxyaryl and heterocycle, may be prepared as described in Scheme 1. Phenols of general formula (1) may be treated with 1-bromo-3-chloropropane (or 1-bromo-2-chloroethane to provide the ethyl analogues) and a base such as potassium carbonate in a solvent such as 2-butanone with heat to provide chlorides of general formula (2). Chlorides of general formula (2) may be treated with tert-butyl pyrrolidinylcarbamate (or tert-butyl (3R)-pyrrolidinylcarbamate or tert-butyl (3S)-pyrrolidinylcarbamate), potassium iodide, a base such as potassium carbonate in a solvent such as 2-butanone with heat to provide N-boc aminopyrrolidines which may be deprotected with acid such as 4N HCl in 1,4-dioxane or trifluoroacetic acid in $CH_2Cl_2$ to provide aminopyrrolidines of general formula (3). Aminopyrrolidines of general formula (3) may be treated with sulfonyl chlorides of general formula (4), a base such as triethylamine, diisopropylamine or a polymer supported base such as tris(2-aminoethyl)amine-polystyrene resin and catalytic DMAP in a solvent such as methylene chloride or DMF to provide sulfonamides of general formula (5). Sulfonamides of general formula (5) may be treated with a base such as sodium hydride and an electrophile such as, for example, iodomethane, allyl bromide or propargyl bromide to provide sulfonamides of general formula (6).

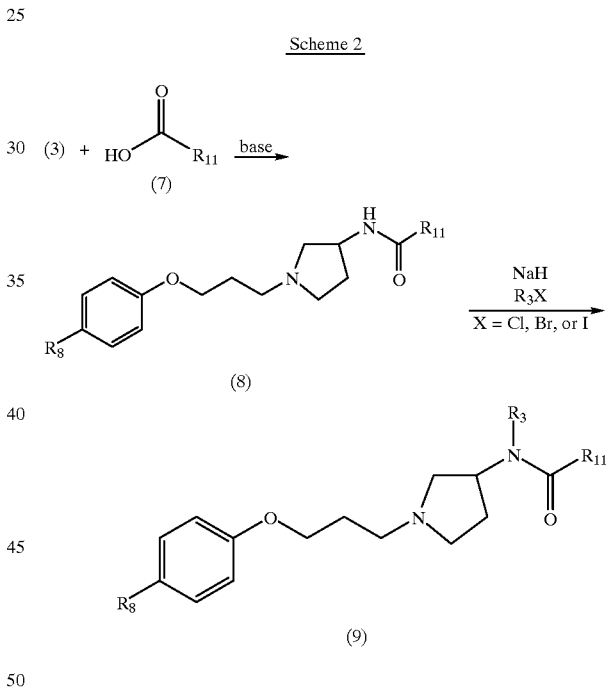

Amides of general formula (9), wherein $R_3$ and $R_8$ are as defined in formula I and $R_{11}$ is selected from hydrogen, alkenyl, alkenyloxy, alkoxy, alkyl, alkynyl, alkynyloxy, amino, arylalkenyl, arylalkyl, arylaryl, aryl, arylheterocyle, aryloxyaryl, cycloalkylalkyl, cycloalkyl, heterocyclealkyl, heterocyclearyl, heterocycle, heterocycleheterocycle, heterocycleoxyalkyl, heterocycleoxyaryl, and heterocyclethioalkyl, may be prepared as described in Scheme 2. Aminopyrrolidines of general formula (3), from Scheme 1, may be treated with acids of general formula (7), a coupling reagent such as DCC, EDCI, or a polymer supported coupling reagent (N-cyclohexylcarbodiimide, N'-methyl polystyrene resin), catalytic DMAP, a base such as triethylamine, diisopropylamine or a polymer supported base (tris(2-aminoethyl)amine-polystyrene resin) and optionally HOBT to provide amides of general formula (8). Alternatively, aminopyrrolidines of general formula (3) may be treated with acid chlorides and a base to provide amides of general formula (8). Amides of general formula (8) may be treated with a base such as sodium hydride and an electrophile such as, for example, iodomethane, allyl bromide, propargyl bromide or an acid chloride to provide amides of general formula (9).

Scheme 3

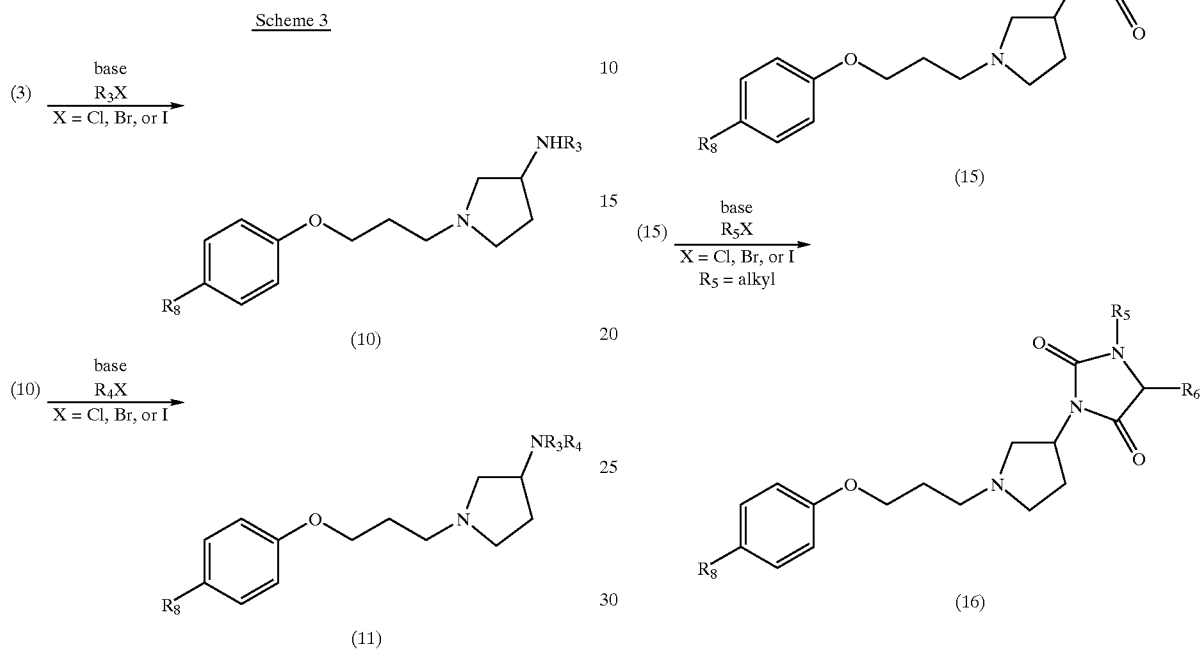

Amines of general formula (10) and (11), wherein $R_8$ is as defined in formula I and $R_3$ and $R_4$ are independently selected from alkenyl, alkyl, alkynyl, arylalkyl, cycloalkyl, cycloalkylalkyl, heterocycle and heterocyclealkyl, may be prepared as described in Scheme 3. Aminopyrrolidines of general formula (3), from Scheme 1, may be treated with electrophiles such as, for example, iodomethane, allyl bromide, propargyl bromide, benzylbromide, bromocyclohexane or 3,6-dichloropyridazine and a base such as triethylamine or diisopropylamine in a solvent such as DMF or THF to provide monosubstituted amines of general formula (10). Monosubstituted amines of general formula (10) may be retreated with an electrophile and a base to provide disubstituted amines of general formula (11).

Scheme 4

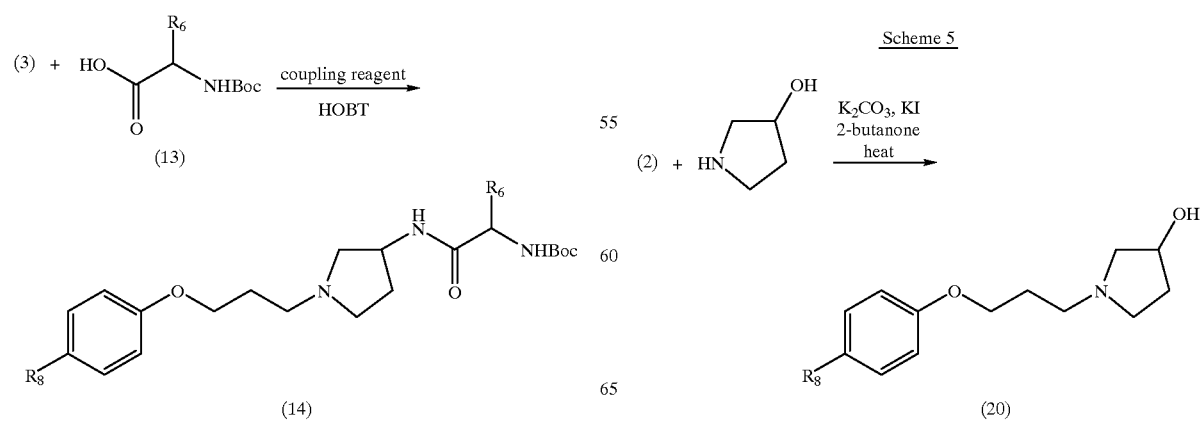

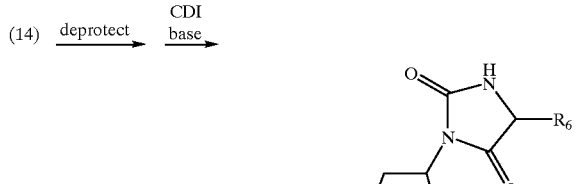

2,5-Dioxo-1-imidazolidines of general formula (15) and (16), wherein $R_5$, $R_6$, and $R_8$ are as defined in formula I, may be prepared as described in Scheme 4. Aminopyrrolidines of general formula (3), from Scheme 1, may be treated with N-protected (L) α-amino acids or N-protected (D) α-amino acids of general formula (13), a coupling reagent such as DCC or EDCI and 1-hydroxybenzotriazole hydrate (HOBT) in a solvent such as DMF or methylene chloride to provide amides of general formula (14). Amides of general formula (14) may be deprotected with acid such as 4N HCl in 1,4-dioxane or trifluoroacetic acid in methylene chloride and then treated with 1,1-carbonyldiimidazole (CDI) and a base such as triethylamine or diisopropylamine in a solvent such as acetonitrile to provide 2,5-dioxo-1-imidazolidines of general formula (15). 2,5-Dioxo-1-imidazolidines of general formula (15) may be treated with a base such as sodium hydride and an alkyl halide to provide 2,5-dioxo-1-imidazolidines of general formula (16).

Scheme 5

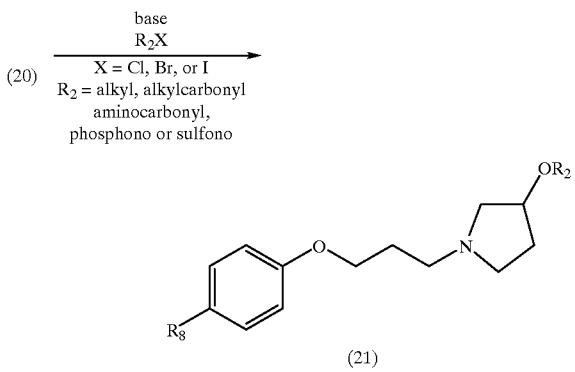

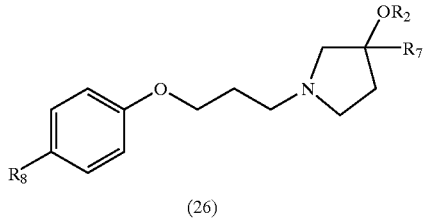

Alkoxy pyrrolidines of general formula (21), wherein $R_2$ and $R_8$ are as defined in formula I, may be prepared as described in Scheme 5. Chlorides of general formula (2), from Scheme 1, may be treated with 3-hydroxypyrrolidine (or (3R)-hydroxypyrrolidine or (3S)-hydroxypyrrolidine), a base such as potassium carbonate, and potassium iodide in a solvent such as 2-butanone with heat to provide hydroxy pyrrolidines of general formula (20).

Hydroxy pyrrolidines of general formula (20) may be treated with a base such as sodium hydride and alkyl halides, acid chlorides, carbamyl chlorides, sulfonyl chlorides or chlorophosphates in a solvent such as THF or DMF to provide alkoxy pyrrolidines of general formula (21).

Scheme 6

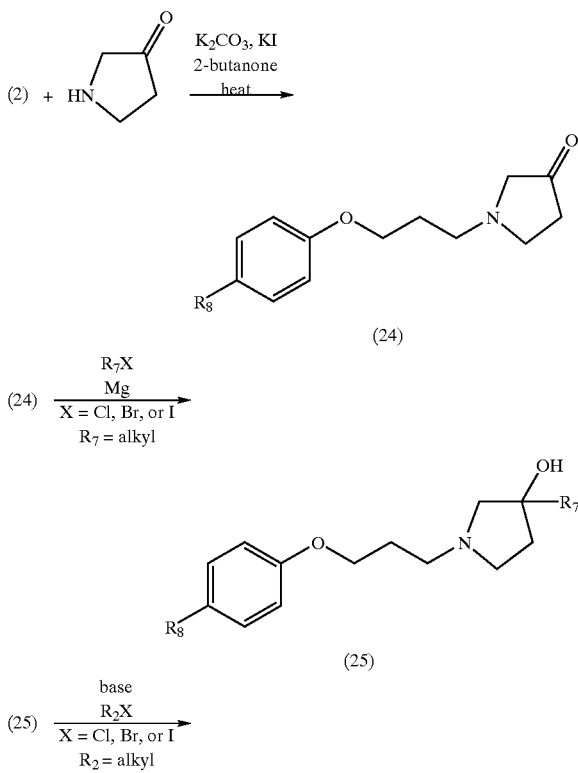

Alkoxy pyrrolidines of general formula (26), wherein $R_2$, $R_7$ and $R_8$ are as defined in formula I, may be prepared as described in Scheme 6. Chlorides of general formula (2), from Scheme 1, may be treated with 3-pyrrolidinone, a base such as potassium carbonate, and potassium iodide in a solvent such as 2-butanone with heat to provide ketones of general formula (24). Ketones of general formula (24) may be treated with alkyl halides, magnesium metal and 1,2-dibromoethane (or ketones of general formula (24) may be treated with an alkyllithium reagent) in a solvent such as THF or diethyl ether to provide tertiary alcohols of general formula (25). Tertiary alcohols of general formula (25) may be treated with a base such as sodium hydride and an alkyl halide in a solvent such as THF or DMF to provide alkoxy pyrrolidines of general formula (26).

Scheme 7

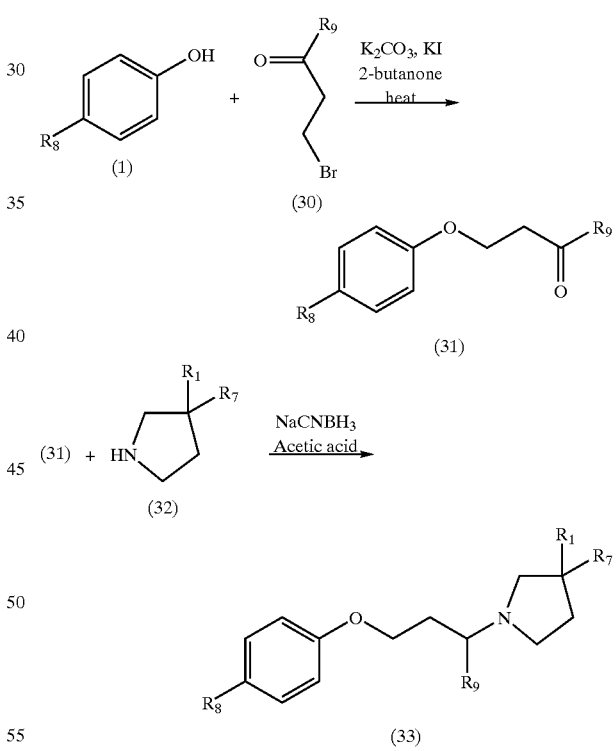

3-Substituted pyrrolidines of general formula (33), wherein $R_1$, $R_7$, $R_8$, and $R_9$ are as defined in formula I, may be prepared as described in Scheme 7. Phenols of general formula (1), from Scheme 1, may be treated with haloketones of general formula (30), a base such as potassium carbonate, and potassium iodide in a solvent such as 2-butanone with heat to provide ketones of general formula (31). Ketones of general formula (31) may be treated with sodium cyanoborohydride under acidic conditions (or other standard reductive-amination conditions) to provide 3-substituted pyrrolidines of general formula (33).

Schemes 1–7 exemplify preparation of compounds of the present invention wherein Z, as defined in formula I, is $CH_2$. Compounds of the present invention wherein Z, as defined in formula I, is a covalent bond may be prepared by using the methods described in schemes 1–7 and substituting 1-bromo-2-chloroethane for 1-bromo-3-chloropropane.

The compounds and processes of the present invention will be better understood by reference to the following examples, which are intended as an illustration of and not a limitation upon the scope of the invention. Further, all citations herein are incorporated by reference.

EXAMPLE 1

N-{(3R)-1-[3-(4-acetylphenoxy)propyl]
pyrrolidinyl}cyclopropanecarboxamide 1-(4-{3-[(3R)-3-Aminopyrrolidinyl]propoxy}phenyl) ethanone (0.05 g, 0.19 mmol) in dichloromethane (2 mL) was treated with cyclopropane carboxylic acid (0.025 g, 0.29 mmol) followed by N-cyclohexylcarbodiimide, N'-methyl polystyrene resin (0.15 g, 0.29 mmol, 2 mmol/g loading) and catalytic N,N-dimethylaminopyridine. After shaking at ambient temperature for 14 hours, the mixture was treated with tris-(2-aminoethyl)-amine-polystyrene (0.063 g, 0.19 mmol, 3 mmol/g loading) resin and the reaction mixture shaken for an additional 2 hours. The mixture was filtered and the filtrate was concentrated. The residue was purified using reverse phase HPLC to afford 0.04 g (63%) of the title compound.
MS (ESI+) m/z 331 (M+H)$^+$; $^1$H NMR (300 MHz, DMSO-d$_6$) δ 8.2 (d, 1H), 7.9 (d, 2H), 7.00 (d, 2H), 4.2 (m, 1H), 4.15 (t, 2H), 2.7–2.8 (m, 2H), 2.5 (m, 2H), 2.2 (m, 2H), 1.9 (s, 3H), 1.8 (m, 2H), 1.6 (m, 2H), 0.6 (m, 4H).

EXAMPLE 2

N-1 (3R)-1-[3-(4-acetylphenoxy)propyl]
pyrrolidinyl]-2-[(4-methyl-2-pyrimidinyl)sulfanyl]
acetamide 1-(4-{3-[(3R)-3-Aminopyrrolidinyl]propoxy}phenyl) ethanone and [(4-methyl-2-pyrimidinyl)sulfanyl]acetic acid were processed as described in Example 1 to provide the title compound.
MS (ESI+) m/z 429 (M+H)$^+$; $^1$H NMR (300 MHz, DMSO-d$_6$) δ 8.4 (d, 2H), 8.2 (d, 1H), 7.8 (d, 2H), 7.0 (d, 2H), 6.92 (d, 2H), 4.15 (m, 3H), 3.7 (s, 2H), 2.65–2.7 (m, 2H), 2.3 (s,3H), 2.25 (m, 2H), 2.0 (m, 2H), 1.90 (s, 3H), 1.85 (m, 2H), 1.6 (m, 2H).

EXAMPLE 3

N-{(3R)-1-[3-(4-acetylphenoxy)
propyl]pyrrolidinyl{nicotinamide 1-(4-{3-[(3R)-3-Aminopyrrolidinyl]propoxy}phenyl) ethanone and nicotinic acid were processed as described in Example 1 to provide the title compound.
MS (ESI+) m/z 368 (M+H)$^+$; $^1$H NMR (300 MHz, DMSO-d6) δ 9.0 (s, 1H), 8.6 (d, 1H), 8.55 (d, 1H), 8.1 (d, 1H), 7.8 (d, 2H), 7.4 (d, 1H), 7.0 (d, 2H), 4.25 (m, 1H), 4.0 (t, 2H) 2.8 (t, 2H), 2.6 (m, 2H), 2.2 (m, 2H), 1.95 (m, 2H), 1.8 (s, 3H), 1.75 (m, 2H).

EXAMPLE 4

N-{(3R)-1-[3-(4-acetylphenoxy)propyl]
pyrrolidinyl}-2-(3-pyridinyl)-1,3-thiazole-4-
carboxamide 1-(4-{3-[(3R)-3-Aminopyrrolidinyl]propoxy}phenyl) ethanone and 2-(3-pyridinyl)-1,3-thiazole-4-carboxylic acid were processed as described in Example 1 to provide the title compound.
MS (ESI+) m/z 451 (M+H)$^+$; $^1$H NMR (300 MHz, DMSO-d$_6$) δ 9.25 (s, 1H), 8.7 (d, 1H), 8.4 (m, 2H), 7.90 (d, 2H), 7.6 (m, 2H), 7.0 (d, 2H), 4.25 (m, 1H), 4.2 (t, 2H), 2.8 (m, 2H), 2.6 (m, 2H), 2.2 (m, 2H), 2.0 (m, 2H), 1.95 (s, 3H), 1.8 (m, 2H).

EXAMPLE 5

N-{(3R)-1-[3-(4-acetylphenoxy)propyl]
pyrrolidinyl}-4-cyanobenzenesulfonamide 1-(4-{3-[(3R)-3-Aminopyrrolidinyl]propoxy}phenyl) ethanone and 4-cyanobenzenesulfonyl chloride were processed as described in Example 20 to provide the title compound.

EXAMPLE 6

N-{(3R)-1-[3-(4-acetylphenoxy)
propyl]pyrrolidinyl}-2-propanesulfonamide 1-(4-{3-[(3R)-3-aminopyrrolidinyl]propoxy}phenyl) ethanone and 2-propanesulfonyl chloride were processed as described in Example 20 to provide the title compound.

EXAMPLE 7

1-(4-{3-[(3R)-3-
aminopyrrolidinyl]propoxy}phenyl)-1-propanone 1-(4-Hydroxyphenyl)-1-propanone was processed as described in Examples 9A-C to provide the title compound.
MS (ESI+) m/z 276 (M+H)$^+$; $^1$H NMR (300 MHz, D$_2$O) δ 8.0 (d, 2H), 7.0 (d, 2H), 4.25 (m, 3H), 3.8 (br s, 2H), 3.6 (m, 2H), 3.0 (q, 2H), 2.8 (br s, 2H), 2.2 (m, 2H), 1.1 (t, 3H).

EXAMPLE 8

(5R)-3-{(3R)-1-[3-(4-acetylphenoxy)propyl]
pyrrolidinyl}-5-methyl-2,4-imidazolidinedione 1-(4-{3-[(3R)-3-Aminopyrrolidinyl]propoxy}phenyl) ethanone and (2R)-2-[(tert-butoxycarbonyl)amino] propanoic acid were processed as described in Examples 9D-F to provide the title compound.
MS (ESI+) m/z 360 (M+H)$^+$; $^1$H NMR (300 MHz, DMSO-d6) 6 8.2 (br s, 1H), 7.9 (d, 2H), 7.0 (d, 2H), 4.4 (m, 1H), 4.15 (t, 2H), 4.0 (m, 1H), 2.85 (m, 2H), 2.8 (m, 2H), 2.6 (m 2H), 2.0 (m, 2H), 1.9 (s, 3H), 1.4 (m, 2H), 1.2 (d, 3H).

EXAMPLE 9

(5S)-3-{(3R)-1-[3-(4-acetylphenoxy)
propyl]pyrrolidinyl}-5-methyl-2,4-
imidazolidinedione

EXAMPLE 9A

1-[4-(3-chloropropoxy)phenyl]ethanone 1-(4-hydroxyphenyl)ethanone, 1-bromo-3-chloropropane and potassium carbonate were processed as described in Example 67B to provide the title compound which was used in the next step without further purification.

EXAMPLE 9B tert-butyl (3R)-1-[3-(4-acetylphenoxy)propyl]
pyrrolidinylcarbamate 1-[4-(3-Chloropropoxy)phenyl]ethanone (1.00 g, 4.7 mmol) in acetone (35 mL), was treated with potassium carbonate (0.97 g, 7.05 mmol), tert-butyl (3R)-pyrrolidinylcarbamate (0.88 g, 4.7 mmol) and potassium iodide (0.78 g, 4.7 mmol). After heating the reaction mixture at reflux for 24 hours, the acetone was evaporated and 50 mL dichloromethane was added. The organic layer was washed with water (3×15 mL) and then concentrated under reduced pressure to provide the title compound which was used in the next step without further purification.

EXAMPLE 9C 1-(4-{3-[(3R)-3-aminopyrrolidinyl]propoxy}phenyl)ethanone tert-Butyl (3R)-1-[3-(4-acetylphenoxy)propyl]pyrrolidinylcarbamate, from Example 9B, in dichloromethane (25 mL) was treated with trifluoroacetic acid (5 mL). After stirring for 2 hours, the mixture was treated with 2N NaOH. The organic layer was collected, dried over $MgSO_4$, filtered and concentrated under reduced pressure to provide the title compound as a brown oil (1.2 g). MS (ESI+) m/z 263 (M+H)$^+$; $^1$H NMR (300 MHz, $D_2O$) δ 8.00 (d, 2H), 7.00 (d, 2H), 4.2 (t, 2H), 3.3 (m, 2H), 3.0 (m, 2H), 2.5–2.8 (m, 5H), 2.44 (s, 3H), 2.1 (m, 2H); $^1$H NMR (300 MHz, DMSO-$d_6$) δ 8.01 (d, 2H), 7.05 (d, 2H), 4.3 (t, 2H), 3.6 (m, 1H), 2.55 (m, 1H), 2.49 (s, 3H), 2.4–2.3 (m, 4H), 2.2 (m, 1H), 1.8–1.6 (m, 2H), 1.4 (m, 2H).

EXAMPLE 9D

Tert-butyl (1S)-2-({(3R)-1-[3-(4-acetylphenoxy)propyl]pyrrolidinyl}amino)-1-methyl-2-oxoethylcarbamate 1-(4-{3-[(3R)-3-Aminopyrrolidinyl]propoxy}phenyl)ethanone (0.1 g, 0.38 mmol) in anhydrous dichloromethane (10 mL), was treated with (2S)-2-[(tert-butoxycarbonyl)amino]propanoic acid (0.1 lg, 0.40 mmol), 1-[3-(dimethylamino)propyl]-3-ethylcarbodiimide hydrochloride (0.077 g, 0.40 mmol) and 1-hydroxybenzotriazole (0.05 g, 0.40 mmol). After stirring at ambient temperature for 12 hours, the mixture was treated with water (20 mL) and the two phases were separated. The aqueous layer was extracted with dichloromethane (3×15 mL). All the organics were combined, dried over $MgSO_4$ and evaporated under reduced pressure to provide the title compound which was used for the subsequent step without further purification.

EXAMPLE 9E (2S)-N-{(3R)-1-[3-(4-acetylphenoxy)propyl]pyrrolidinyl}-2-aminopropanamide tert-Butyl (1S)-2-({(3R)-1-[3-(4-acetylphenoxy)propyl]pyrrolidinyl}amino)-1-methyl-2-oxoethylcarbamate, from Example 9D, was treated with a 10% solution of TFA in dichloromethane (30 mL). After stirring for 2 hours, the mixture was treated with water and the aqueous portion adjusted to pH=8 using 2N NaOH. The organic layer was separated and the aqueous layer extracted with ethyl acetate (3×20 mL). All the organic layers were combined, dried over $MgSO_4$, filtered and evaporated under reduced pressure to provide the title compound.

EXAMPLE 9F (5S)-3-{(3R)-1-[3-(4-acetylphenoxy)propyl]pyrrolidinyl}-5-methyl-2,4-imidazolidinedione (2S)-N-{(3R)-1-[3-(4-Acetylphenoxy)propyl]pyrrolidinyl}-2-aminopropanamide in acetonitrile (25 mL) was treated with 1,1'-carbonyldiimidazole (0.05 g, 0.34 mmol) and triethylamine (0.07 g, 0.68 mmol). After heating at 40° C. for 16 hours, the mixture was allowed to cool to ambient temperature and the solvent was evaporated under reduced pressure. The residue was purified via reverse-phase silica gel chromatography using a C18 column, to provide 0.07 g (49%) of the title compound. MS (ESI+) m/z 360 (M+H)$^+$; $^1$H NMR (300 MHz, DMSO-$d_6$) δ 8.2 (br s, 1H), 7.9 (d, 2H), 7.0 (d, 2H), 4.4 (m, 1H), 4.15 (t, 2H), 3.95 (m, 1H), 2.8 (m, 3H), 2.51 (m, 4H), 2.1 (m, 2H), 1.8 (m, 2H), 1.4 (m, 2H), 1.1 (d, 3H).

EXAMPLE 10

(5R)-3-{(3R)-1-[3-(4-acetylphenoxy)propyl]pyrrolidinyl}-5-isopropyl-2,4-imidazolidinedione 1-(4-{3-[(3R)-3-Aminopyrrolidinyl]propoxy}phenyl)ethanone and (2S)-2-[(tert-butoxycarbonyl)amino]-3-methylbutanoic acid were processed as described in Examples 9D-F to provide the title compound.

EXAMPLE 11

4-cyano-N-((3R)-l-f 3-[4-(cyclopropylcarbonyl)phenoxy]propyl}pyrrolidinyl)benzenesulfonamide (4-{3-[(3R)-3-Aminopyrrolidinyl]propoxy}phenyl)(cyclopropyl)methanone and 4-cyanobenzenesulfonyl chloride were processed as described in Example 20 to provide the title compound.

EXAMPLE 12

N-((3R)1-{3-[4-(cyclopropylcarbonyl)phenoxy]propyl}pyrrolidinyl)-2-propanesulfonamide (4-{3-[(3R)-3-Aminopyrrolidinyl]propoxy}phenyl)(cyclopropyl)methanone and 2-propanesulfonyl chloride were processed as described in Example 20 to provide the title compound.

EXAMPLE 13

N-((3R)-1-{3-[4-(cyclopropylcarbonyl)phenoxy]propyl}pyrrolidinyl)-2-(3-pyridinyl)-1,3-thiazole-4-carboxamide (4-{3-[(3R)-3-Aminopyrrolidinyl]propoxy}phenyl)(cyclopropyl)methanone and 2-(3-pyridinyl)-1,3-thiazole-4-carboxylic acid were processed as described in Example 1 to provide the title compound.

EXAMPLE 14

N-{(3R)-1-[-3-(4-acetylphenoxy)propyl]pyrrolidinyl}-4-cyanobenzamide 1-(4-{3-[(3R)-3-Aminopyrrolidinyl]propoxy}phenyl)ethanone and 4-cyanobenzoic acid were processed as described in Example 1 to provide the title compound. MS (ESI+) m/z 392 (M+H)$^+$; $^1$H NMR (300 MHz, DMSO-$d_6$) δ 8.00 (d, 2H), 7.8–7.9 (m, 4H), 7.00 (d, 2H), 4.4 (m, 1H), 4.15 (m, 2H), 2.8 (m, 2H), 2.5–2.7 (m, 4H), 2.2 (m, 2H), 1.95 (s, 3H), 1.8 (m, 2H).

EXAMPLE 15

N-((3R)-1-{3-[(4'-cyano[1,1'-biphenyll-4-yl)oxy]propyl}pyrrolidinyl)benzenesulfonamide 4'-{3-[(3R)-3-Aminopyrrolidinyl]propoxy}[1,1'-biphenyl]-4-carbonitrile and benzenesulfonyl chloride were processed as described in Example 20 to provide the title compound.

EXAMPLE 16

4-bromo-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 4-bromobenzenesulfonyl chloride were processed as described in Example 20 to provide the title compound.

EXAMPLE 17

N-((3R)-1-{3-[(4'-cyano[1,1'-biphenyll-4-yl)oxy]propyl}pyrrolidinyl)-4-fluorobenzenesulfonamide 4'-{3-[(3R)-3-Aminopyrrolidinyl]propoxy}[1,1'-biphenyl]-4-carbonitrile and 4-fluorobenzenesulfonyl chloride were processed as described in Example 20 to provide the title compound.

EXAMPLE 18

4-chloro-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 4-chlorobenzenesulfonyl chloride were processed as described in Example 20 to provide the title compound.

EXAMPLE 19

N-(4-{[((3R)-1–3-[(4'-cyano[1,1'-biphenyl]-4-yl)oxy]propyl}pyrrolidinyl)amino]sulfonyl}phenyl)acetamide 4'-{3-[(3R)-3-Aminopyrrolidinyl]propoxy}[1,1'-biphenyl]-4-carbonitrile and 4-(acetylamino)benzenesulfonyl chloride were processed as described in Example 20 to provide the title compound.

EXAMPLE 20

N-((3R)-1-{3-[(4'-cyano[1,1'-biphenyl]-4-yl)oxy]propyl}pyrrolidinyl)-4-methoxybenzenesulfonamide 4'-{3-[(3R)-3-Aminopyrrolidinyl]propoxy}[1,1'-biphenyl]-4-carbonitrile (0.05 g, 0.15 mmol) in dichloromethane (2 mL) was treated with polymer supported N,N-diisopropylethylamine (0.10 g, 0.31 mmol, 3mmol/g loading), catalytic N,N-dimethylaminopyridine, and 4-methoxybenzenesulfonyl chloride (0.034 g, 0.17 mmol). After shaking at ambient temperature for 14 hours, the mixture was treated with tris-(2-aminoethyl)-amine-polystyrene (0.05 g, 0.15 mmol, 3 mmol/g loading) resin and the reaction mixture shaken for an additional 2 hours. The reaction mixture was filtered and the filtrate was concentrated. The residue was purified using reverse phase HPLC to afford 0.053 g (79%) of the title compound.
MS (ESI+) m/z 492 (M+H)+; $^1$H NMR (300 MHz, DMSO-$d_6$) δ 7.85 (m, 4H), 7.7 (m, 4H), 7.0 (m, 4H), 4.0 (t, 2H), 3.8 (s, 3H), 3.6 (m, 1H), 2.4–2.6 (m, 4H), 2.2 (m, 1H) 1.8 (m, 4H), 1.5 (m, 1H).

EXAMPLE 21

4-tert-butyl-N-((3R)-1-{3-[(4'-cyano[1,1'-biphenyll-4-yl)oxy]propyl}pyrrolidinyl)benzenesulfonamide 4'-{3-[(3R)-3-Aminopyrrolidinyl]propoxy}[1,1'-biphenyl]-4-carbonitrile and 4-tert-butylbenzenesulfonyl chloride were processed as described in Example 20 to provide the title compound.

EXAMPLE 22

N-((3R)-1-{3-[(4'-cyano[1,1'-biphenyl]-4-yl)oxy]propyl}pyrrolidinyl)-4-methylbenzenesulfonamide 4'-{3-[(3R)-3-Aminopyrrolidinyl]propoxy}[1,1'-biphenyl]-4-carbonitrile and 4-methylbenzenesulfonyl chloride were processed as described in Example 20 to provide the title compound.

EXAMPLE 23

N-((3R)-1-{3-[(4'-cyano[1,1'-biphenyl]-4-yl)oxy]propyl}pyrrolidinyl)-4-(trifluoromethyl)benzenesulfonamide 4'-{3-[(3R)-3-Aminopyrrolidinyl]propoxy}[1,1'-biphenyl]-4-carbonitrile and 4-(trifluoromethyl)benzenesulfonyl chloride were processed as described in Example 20 to provide the title compound.

EXAMPLE 24

N-((3R)-1-{3-[(4'-cyanol[1,1'-biphenyl]-4-yl)oxy]propyl}pyrrolidinyl)-2,5-dimethoxybenzenesulfonamide 4'-{3-[(3R)-3-Aminopyrrolidinyl]propoxy}[1,1'-biphenyl]-4-carbonitrile and 2,5-dimethoxybenzenesulfonyl chloride were processed as described in Example 20 to provide the title compound.

EXAMPLE 25

N-((3R)-1-{3-[(4'-cyano[1,1'-biphenyl]-4-yl)oxy]propyl}pyrrolidinyl)-2-methylbenzenesulfonamide 4'-{3-[(3R)-3-Aminopyrrolidinyl]propoxy}[1,1'-biphenyl]-4-carbonitrile and 2-methylbenzenesulfonyl chloride were processed as described in Example 20 to provide the title compound.
MS (ESI+) m/z 476 (M+H)+; $^1$H NMR (300 MHz, DMSO-$d_6$) δ 7.8 (m, 4H), 7.7 (d, 2H), 7.4 (m, 4H), 7.0 (d, 2H), 4.4 (s, 3H), 4.0 (t, 2H), 3.7 (m, 1H), 2.8 (m, 1H), 2.5 (m, 4H), 2.2 (m, 1H), 2.0 (m, 1H), 1.9 (m, 2H), 1.6 (m, 1H).

EXAMPLE 26

3-chloro-N-((3R)-1-{3-[(4'-cyano[1,1'-biphenyl]-4-yl)oxy]propyl}pyrrolidinyl)-4-fluorobenzenesulfonamide 4'-{3-[(3R)-3-Aminopyrrolidinyl]propoxy}[1,1'-biphenyl]-4-carbonitrile and 3-chloro-4-fluorobenzenesulfonyl chloride were processed as described in Example 20 to provide the title compound.

EXAMPLE 27

N-((3R)-1-{3-[(4'-cyano[1,1'-biphenyl]-4-yl)oxy]propyl}pyrrolidinyl)-4-ethylbenzenesulfonamide 4'-{3-[(3R)-3-Aminopyrrolidinyl]propoxy}[1,1'-biphenyl]-4-carbonitrile and 4-ethylbenzenesulfonyl chloride were processed as described in Example 20 to provide the title compound.

EXAMPLE 28

N-((3R)-1-{3-[(4'-cyano[1,1'-biphenyl]-4-yl)oxy]propyl}pyrrolidinyl)-4-isopropylbenzenesulfonamide 4'-{3-[(3R)-3-Aminopyrrolidinyl]propoxy}[1,1'-biphenyl]-4-carbonitrile and 4-(2-propyl)benzenesulfonyl chloride were processed as described in Example 20 to provide the title compound.

EXAMPLE 29

N-((3R)-1-{3-[(4'-cyano[1,1'-biphenyl]-4-yl)oxy]propyl}pyrrolidinyl)-2-fluorobenzenesulfonamide 4'-{3-[(3R)-3-Aminopyrrolidinyl]propoxy}[1,1'-biphenyl]-4-carbonitrile and 2-fluorobenzenesulfonyl chloride were processed as described in Example 20 to provide the title compound.

EXAMPLE 30

2-chloro-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 2-chlorobenzenesulfonyl chloride were processed as described in Example 20 to provide the title compound.

EXAMPLE 31

3-chloro-N-((3R)-1-{3-](4'-cyano]1,1'-bipheny-4-yl)oxy]propyl}pyrrolidinyl)benzenesulfonamide 4'-{3-[(3R)-3-Aminopyrrolidinyl]propoxy}[1,1'-biphenyl]-4-carbonitrile and 3-chlorobenzenesulfonyl chloride were processed as described in Example 20 to provide the title compound.

EXAMPLE 32

3,5-dichloro-N-((3R)-1-{3-[(4'cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 3,5-dichlorobenzenesulfonyl chloride were processed as described in Example 20 to provide the title compound.

EXAMPLE 33

4-cyano-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 4-cyanobenzenesulfonyl chloride were processed as described in Example 20 to provide the title compound.

EXAMPLE 34

3-cyano-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 3-cyanobenzenesulfonyl chloride were processed as described in Example 20 to provide the title compound.
MS (ESI+) m/z 487 (M+H)$^+$; $^1$H NMR (300 MHz, DMSO-d$_6$) δ 8.2 (s, 1H), 8.1 (d, 2H), 7.8 (m, 5H), 7.6 (d, 2H), 7.0 (d, 2H), 4.0 (t, 2H), 3.7 (m, 1H), 2.8 (m,1H) 2.4–2.6 (m, 5H), 2.2 (m, 1H), 1.8–2.0 (m, 2H), 1.5 (m, 1H).

EXAMPLE 35

N-((3R)-1-{3-[(4'-cyano[1,1'-bipheny]-4-yl)oxy]propyl}pyrrolidinyl)-1-methyl-1H-imidazole-4-sulfonamide 4'-{3-[(3R)-3-Aminopyrrolidinyl]propoxy}[1,1'-biphenyl]-4-carbonitrile and 1 methyl-1H-imidazole-4-sulfonyl chloride were processed as dscribed in Example 20 to provide the title compound.

EXAMPLE 36

N-((3R)-1-{3-[(4'-cyanol 1,1'-biphenyl]-4-yl)oxy]propyl}pyrrolidinyl)-2-thiophenesulfonamide 4'-{3-[(3R)-3-Aminopyrrolidinyl]propoxy}[1,1'-biphenyl]-4-carbonitrile and 2-thiophenesulfonyl chloride were processed as described in Example 20 to provide the title compound.

EXAMPLE 37

5-chloro-N-((3R)-1-{3-[(4'-cyano[1,1'-biphenyl]-4-yl)oxy]propyl}pyrrolidinyl)-3-methyl-1-benzothiophene-2-sulfonamide 4'-{3-[(3R)-3-Aminopyrrolidinyl]propoxy}[1,1'-biphenyl]-4-carbonitrile and 5-chloro-3-methyl-1-benzothiophene-2-sulfonyl chloride were processed as described in Example 20 to provide the title compound.

EXAMPLE 38

N-((3R)-1-{3-[(4'-cyano[1,1'-biphenyl]-4-yl)oxy]propyl}pyrrolidinyl)-3,5-bis(trifluoromethyl)benzenesulfonamide 4'-{3-[(3R)-3-Aminopyrrolidinyl]propoxy}[1,1'-biphenyl]-4-carbonitrile and 3,5-bis(trifluoromethyl)benzenesulfonyl chloride were processed as described in Example 20 to provide the title compound.

EXAMPLE 39

N-(5-{[((3R)-1-{3-[(4'-cyano[1,1'-biphenyl]-4-yl)oxy]propyl}pyrrolidinyl)amino]sulfonyl}-4-methyl-1,3-thiazol-2-yl)acetamide 4'-{3-[(3R)-3-Aminopyrrolidinyl]propoxy}[1,1'-biphenyl]-4-carbonitrile and 2-(acetylamino)-4-methyl-1,3-thiazole-5-sulfonyl chloride were processed as described in Example 20 to provide the title compound.

EXAMPLE 40

N-((3R)-1-{3-[(4'-cyano[1,1'-biphenyl]-4-yl)oxy]propyl}pyrrolidinyl)-8-quinolinesulfonamide 4'-{3-[(3R)-3-Aminopyrrolidinyl]propoxy}[1,1'-biphenyl]-4-carbonitrile and 8-quinolinesulfonyl chloride were processed as described in Example 20 to provide the title compound.

EXAMPLE 41

4-butoxy-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 4-butoxybenzenesulfonyl chloride were processed as described in Example 20 to provide the title compound.

EXAMPLE 42

N-((3R)-1-{3-[(4'-cyanol[1,1'-biphenyl]-4-yl)oxy]propyl}pyrrolidinyl)-3,4-dimethoxybenzenesulfonamide 4'-{3-[(3R)-3-Aminopyrrolidinyl]propoxy}[1,1'-biphenyl]-4-carbonitrile and 3,4-dimethoxybenzenesulfonyl chloride were processed as described in Example 20 to provide the title compound.

EXAMPLE 43

3-chloro-N-((3R)-1-{3-[(4'-cyano[1,1'-biphenyl]-4-yl)oxy]propyl}pyrrolidinyl)-4-methylbenzenesulfonamide 4'-{3-[(3R)-3-Aminopyrrolidinyl]propoxy}[1,1'-biphenyl]-4-carbonitrile and 3-chloro-4-methylbenzenesulfonyl chloride were processed as described in Example 20 to provide the title compound.

EXAMPLE 44

N-((3R)-1-{3-[(4'-cyano[1,1'-biphenyl]-4-yl)oxy]propyl}pyrrolidinyl)-2-phenylethenesulfonamide 4'-{3-[(3R)-3-Aminopyrrolidinyl]propoxy}[1,1'-biphenyl]-4-carbonitrile and 2-phenylethenesulfonyl chloride were processed as described in Example 20 to provide the title compound.

EXAMPLE 45

N-((3R)-1-{3-[(4'-cyano[1,1'-biphenyl]-4-yl)oxy]propyl}pyrrolidinyl)-2-(trifluoromethoxy)benzenesulfonamide 4'-{3-[(3R)-3-Aminopyrrolidinyl]propoxy}[1,1'-biphenyl]-4-carbonitrile and 2-(trifluoromethoxy)benzenesulfonyl chloride were processed as described in Example 20 to provide the title compound.

EXAMPLE 46

2-cyano-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 2-cyanobenzenesulfonyl chloride were processed as described in Example 20 to provide the title compound.

EXAMPLE 47

N-((3R)-1-{3-[(4'-cyano[1,1'-biphenyl]-4-yl)oxy]propyl}pyrrolidinyl)-3-methylbenzenesulfonamide 4'-{3-[(3R)-3-Aminopyrrolidinyl]propoxy}[1,1'-biphenyl]-4-carbonitrile and 3-methylbenzenesulfonyl chloride were processed as described in Example 20 to provide the title compound.

EXAMPLE 48

N-((3R)-1-{3-[(4'-cyano[1,1'-biphenyl]-4-yl)oxy]propyl}pyrrolidinyl)-4-(trifluoromethyl)benzenesulfonamide 4'-{3-[(3R)-3-Aminopyrrolidinyl]propoxy}[1,1'-biphenyl]-4-carbonitrile and 4-(trifluoromethyl)benzenesulfonyl chloride were processed as described in Example 20 to provide the title compound.

EXAMPLE 49

N-((3R)-1-{3-[(4'-cyano[1,1'-biphenyl]-4-yl)oxy]propyl}pyrrolidinyl)-3-fluorobenzenesulfonamide 4'-{3-[(3R)-3-Aminopyrrolidinyl]propoxy}[1,1'-biphenyl]-4-carbonitrile and 3-fluorobenzenesulfonyl chloride were processed as described in Example 20 to provide the title compound.

EXAMPLE 50

N-((3R)-1-{3-[(4'-cyano[1,1'-biphenyl]-4-yl)oxy]propyl}pyrrolidinyl)-4-(trifluoromethoxy)benzenesulfonamide 4'-{3-[(3R)-3-Aminopyrrolidinyl]propoxy}[1,1'-biphenyl]-4-carbonitrile and 4-(trifluoromethoxy)benzenesulfonyl chloride were processed as described in Example 20 to provide the title compound.

EXAMPLE 51

N-((3R)-1-{3-[(4'-cyano[1,1'-biphenyl]-4-yl)oxy]propyl}pyrrolidinyl)-2,4-difluorobenzenesulfonamide 4'-{3-[(3R)-3-Aminopyrrolidinyl]propoxy}[1,1'-biphenyl]-4-carbonitrile and 2,4-difluorobenzenesulfonyl chloride were processed as described in Example 20 to provide the title compound.

EXAMPLE 52

N-((3R)-1-{3-[(4'-cyano[1,1'-biphenyl]-4-yl)oxy]propyl}pyrrolidinyl)-7-isoguinolinesulfonamide 4'-{3-[(3R)-3-Aminopyrrolidinyl]propoxy}[1,1'-biphenyl]-4-carbonitrile and 7-isoquinolinesulfonyl chloride were processed as described in Example 20 to provide the title compound.

EXAMPLE 53

N-(2-chloro-4-{[((3R)-1-{3-[(4'-cyano[1,1'-biphenyl]-4-yl)oxy]propyl}pyrrolidinyl)aminolsulfonyl}phenyl)acetamide 4'-{3-[(3R)-3-Aminopyrrolidinyl]propoxy}[1,1'-biphenyl]-4-carbonitrile and 4-(acetylamino)-3-chlorobenzenesulfonyl chloride were processed as described in Example 20 to provide the title compound.

EXAMPLE 54

3,4-dichloro-N-((3R)-1-{3-[(4'-cyano[1,1'-biphenyl]-4-yl)oxy]propyl}pyrrolidinyl)benzenesulfonamide 4'-{3-[(3R)-3-Aminopyrrolidinyl]propoxy}[1,1'-biphenyl]-4-carbonitrile and 3-dichlorobenzenesulfonyl chloride were processed as described in Example 20 to provide the title compound.

EXAMPLE 55

N-((3R)-1-{3-[4-(cyclopropylcarbonyl)phenoxy]propyl}pyrrolidinyl)benzenesulfonamide (4-{3-[(3R)-3-Aminopyrrolidinyl]propoxy}phenyl)(cyclopropyl)methanone and benzenesulfonyl chloride were processed as described in Example 20 to provide the title compound.

EXAMPLE 56

4-bromo-N-((3R)-1-{3-[4-(cyclopropylcarbonyl)phenoxy]propyl}pyrrolidinyl)benzenesulfonamide (4-{3-[(3R)-3-Aminopyrrolidinyl]propoxy}phenyl)(cyclopropyl)methanone and 4-bromobenzenesulfonyl chloride were processed as described in Example 20 to provide the title compound.

EXAMPLE 57

N-((3R)-1-{3-[4-(cyclopropylcarbonyl)phenoxy]
propyl}pyrrolidinyl)-4-fluorobenzenesulfonamide (4-{3-[(3R)-3-Aminopyrrolidinyl]propoxy}phenyl)
(cyclopropyl)methanone and 4-fluorobenzenesulfonyl chloride were processed as described in Example 20 to provide the title compound.

EXAMPLE 58

4-chloro-N-((3R)-1-{3-[4-(cyclopropylcarbonyl)
phenoxy]propyl}pyrrolidinyl)benzenesulfonamide (4-{3-[(3R)-3-Aminopyrrolidinyl]propoxy}phenyl)
(cyclopropyl)methanone and 4-chlorobenzenesulfonyl chloride were processed as described in Example 20 to provide the title compound.

EXAMPLE 59

N-((3R)-1-{3-[4-(cyclopropylcarbonyl)phenoxy]
propyl}pyrrolidinyl)-4-methoxybenzenesulfonamide (4-{3-[(3R)-3-Aminopyrrolidinyl]propoxy}phenyl)
(cyclopropyl)methanone and 4-methoxybenzenesulfonyl chloride were processed as described in Example 20 to provide the title compound.

EXAMPLE 60

4-tert-butyl-N-((3R)-1-{3-[4-(cyclopropylcarbonyl)
phenoxy]propyl}pyrrolidinyl)benzenesulfonamide (4-{3-[(3R)-3-Aminopyrrolidinyl]propoxy}phenyl)
(cyclopropyl)methanone and 4-tert-butylbenzenesulfonyl chloride were processed as described in Example 20 to provide the title compound.

EXAMPLE 61

N-((3R)-1-{3-[4-(cyclopropylcarbonyl)phenoxy]
propyl}pyrrolidinyl)-4-methylbenzenesulfonamide (4-{3-[(3R)-3-Aminopyrrolidinyl]propoxy}phenyl)
(cyclopropyl)methanone and 4-methylbenzenesulfonyl chloride were processed as described in Example 20 to provide the title compound.

EXAMPLE 62

N-((3R)-1-{3-[4-(cyclopropylcarbonyl)phenoxy]
propyl}pyrrolidinyl)-3-(trifluoromethyl)
benzenesulfonamide (4-{3-[(3R)-3-Aminopyrrolidinyl]propoxy}phenyl)
(cyclopropyl)methanone and
3-trifluoromethylbenzenesulfonyl chloride were processed as described in Example 20 to provide the title compound.

EXAMPLE 63

N-((3R)-1-{3-[4-(cyclopropylcarbonyl)phenoxy]
propyl}pyrrolidinyl)-2,5-
dimethoxybenzenesulfonamide (4-{3-[(3R)-3-Aminopyrrolidinyl]propoxy}phenyl)
(cyclopropyl)methanone and 2,5-dimethoxybenzenesulfonyl chloride were processed as described in Example 20 to provide the title compound.

EXAMPLE 64

N-((3R)-1-{3-[4-(cyclopropylcarbonyl)phenoxy]
propyl}pyrrolidinyl)-2-methylbenzenesulfonamide (4-{3-[(3R)-3-Aminopyrrolidinyl]propoxy}phenyl)
(cyclopropyl)methanone and 2-methylbenzenesulfonyl chloride were processed as described in Example 20 to provide the title compound.

EXAMPLE 65

3-chloro-N-((3R)-1-{3-[4-(cyclopropylcarbonyl)
phenoxy]propyl}pyrrolidinyl)-4-
fluorobenzenesulfonamide (4-{3-[(3R)-3-Aminopyrrolidinyl]propoxy}phenyl)
(cyclopropyl)methanone and 3-chloro-4-fluorobenzenesulfonyl chloride were processed as described in Example 20 to provide the title compound.

EXAMPLE 66

N-((3R)-1-{3-[4-(cyclopropylcarbonyl)phenoxy]
propyl}pyrrolidinyl)-4-ethylbenzenesulfonamide (4-{3-[(3R)-3-Aminopyrrolidinyl]propoxy}phenyl)
(cyclopropyl)methanone and 4-ethylbenzenesulfonyl chloride were processed as described in Example 20 to provide the title compound.

EXAMPLE 67

N-((3R)-1-{3-[4-(cyclopropylcarbonyl)phenoxy]
propyl}pyrrolidinyl)-4-
isopropylbenzenesulfonamide

EXAMPLE 67A

Cyclopropyl(4-hydroxyphenyl)methanone

Sodium hydroxide in water (50% (w/w), 40.4 mL) was treated over a period of 15 minutes with para-hydroxy-4-chlorobutyrophenone (25.0 g, 137 mmol), followed by additional aqueous sodium hydroxide (25% (w/w), 177 mL). Additional para-hydroxy-4-chlorobutyrophenone (25.0 g, 137 mmol) was added portionwise to the reaction mixture, followed by solid sodium hydroxide (40.4 g) resulting in the formation of a yellow precipitate. After refluxing for 60 minutes, water (50 mL) was added and the resulting mixture was refluxed for another 60 minutes, allowed to cool to ambient temperature, diluted with water (100 mL) and neutralized with acetic acid. The precipitate was collected by filtration, washed with water, air-dried, and triturated at 40° C. with chloroform (1.5 L). The chloroform solution was dried (MgSO$_4$), filtered, and concentrated. The residue was crystallized from chloroform/hexanes to provide 26.65 g (95%) of the title compound. MS (APCI(−)) m/z 161 (M-H)$^-$; $^1$H NMR (300 MHz, CDCl$_3$) δ 7.9 (d, 2H), 6.9 (d, 2H), 2.65 (m, 1H), 1.23 (m, 2H), 1.03 (m, 2H).

EXAMPLE 67B (4-(3-chloropropoxy)phenyl)(cyclopropyl)
methanone

Cyclopropyl(4-hydroxyphenyl)methanone (10 g, 61.7 mmol), K$_2$CO$_3$ (12.7 g, 91.9 mmol), and 1-bromo-3- chloropropane (10.74 g, 68.2 mmol) in 2-butanone (100 mL) were refluxed for 24 hours, allowed to cool to ambient temperature, filtered, and concentrated. The residue was heated at 40° C. under reduced pressure for three hours to provide the title compound of sufficient purity for subsequent use without further purification (13.25 g, 90%).

EXAMPLE 67C (4-{3-[(3R)-3-aminopyrrolidinyl]propoxy}phenyl) (cyclopropyl)methanone (4-(3-Chloropropoxy)phenyl)(cyclopropyl)methanone was processed as described in Examples 9B and 9C to provide the title compound.

EXAMPLE 67D

N-((3R)-1-{3-4-(cyclopropylcarbonyl)phenoxy] propyl}pyrrolidinyl)-4-isopropylbenzenesulfonamide (4-{3-[(3R)-3-Aminopyrrolidinyl]propoxy}phenyl) (cyclopropyl)methanone and 4-(2-propyl)benzenesulfonyl chloride were processed as described in Example 20 to provide the title compound.
MS (ESI+) m/z 472 (M+H)$^+$; $^1$H NMR (300 MHz, DMSO-d$_6$) δ 8.0 (d, 2H), 7.7 (d, 2H), 7.4 (d, 2H), 7.0 (d, 2H), 4.1 (t, 2H), 3.8 (br s, 1H), 3.0 (m, 1H), 2.85 (m, 1H), 2.2 (m, 1H), 1.8–1.95 (m, 2H), 1.5 (m, 1H), 1.1 (d, 6H), 1.0 (d, 4H)

EXAMPLE 68

N-((3R)-1-{3-[4-(cyclopropylcarbonyl)phenoxy] propyl}pyrrolidinyl)-2-fluorobenzenesulfonamide (4-{3-[(3R)-3-Aminopyrrolidinyl]propoxy}phenyl) (cyclopropyl)methanone and 2-fluorobenzenesulfonyl chloride were processed as described in Example 20 to provide the title compound.

EXAMPLE 69

2-chloro-N-((3R)-1-{3-[4-(cyclopropylcarbonyl) phenoxy]propyl}pyrrolidinyl)benzenesulfonamide (4-{3-[(3R)-3-Aminopyrrolidinyl]propoxy}phenyl) (cyclopropyl)methanone and 2-chlorobenzenesulfonyl chloride were processed as described in Example 20 to provide the title compound.

EXAMPLE 70

3-chloro-N-((3R)-1-{3-]4-(cyclopropylcarbonyl) phenoxy]propyl}pyrrolidinyl)benzenesulfonamide (4-{3-[(3R)-3-Aminopyrrolidinyl]propoxy}phenyl) (cyclopropyl)methanone and 3-chlrorobenzenesulfonyl chloride were processed as described in Example 20 to provide the title compound.

EXAMPLE 71

3-cyano-N-((3R)-1-{3-[4-(cyclopropylcarbonyl) phenoxy]propyl}pyrrolidinyl)benzenesulfonamide (4-{3-[(3R)-3-Aminopyrrolidinyl]propoxy}phenyl) (cyclopropyl)methanone and 3-cyanobenzenesulfonyl chloride were processed as described in Example 20 to provide the title compound.

EXAMPLE 72

N-{(3R)-1-[3-(4-acetylphenoxy)propyl] pyrrolidinyl}-3-fluorobenzenesulfonamide 1-(4-{3-[(3R)-3-Aminopyrrolidinyl]propoxy}phenyl) ethanone and 3-fluorobenzenesulfonyl chloride were processed as described in Example 20 to provide the title compound.

EXAMPLE 73

N-{(3R)-1-[3-(4-acetylphenoxy)propyl] pyrrolidinyl}-4-(trifluoromethoxy) benzenesulfonamide 1-(4-{3-[(3R)-3-Aminopyrrolidinyl]propoxy}phenyl) ethanone and 4-(trifluoromethoxy)benzenesulfonyl chloride were processed as described in Example 20 to provide the title compound.
MS (ESI+) m/z 486 (M+H)$^+$; $^1$H NMR (300 MHz, DMSO-d6) δ 8.0 (d, 2H), 7.7 (d, 2H), 7.6 (d, 2H), 7.0 (d, 2H), 4.1 (t, 2H), 3.6 (m, 1H), 2.8 (m, 2H), 2.4–2.5 (m, 1.8–1.9 (m, 4H), 1.45 (m, 1H), 1.25 (s, 9H), 1.00 (d, 4H).

EXAMPLE 74

N-{(3R)-1-[3-(4-acetylphenoxy)propyl] pyrrolidinyl}-2,4-difluorobenzenesulfonamide 1-(4-{3-[(3R)-3-Aminopyrrolidinyl]propoxy}phenyl) ethanone and 2,4-difluorobenzenesulfonyl chloride were processed as described in Example 20 to provide the title compound.

EXAMPLE 75

N-{(3R)-1-[3-(4-acetylphenoxy)propyl] pyrrolidinyl}-5-isoquinolinesulfonamide 1-(4-{3-[(3R)-3-Aminopyrrolidinyl]propoxy}phenyl) ethanone and 5-isoquinolinesulfonyl chloride were processed as described in Example 20 to provide the title compound.

EXAMPLE 76

N-{4-[({(3R)-1-[3-(4-acetylphenoxy)propyl] pyrrolidinyl}amino)sulfonyl]-2-chlorophenyl}acetamide 1-(4-{3-[(3R)-3-Aminopyrrolidinyl]propoxy}phenyl) ethanone and 4-(acetylamino)-3-chlorobenzenesulfonyl chloride were processed as described in Example 20 to provide the title compound.

EXAMPLE 77

N-{(3R)-1-[3-(4-acetylphenoxy)propyl] pyrrolidinyl}-3,4-dichlorobenzenesulfonamide 1-(4-{3-[(3R)-3-Aminopyrrolidinyl]propoxy}phenyl) ethanone and 3,4-dichlorobenzenesulfonyl chloride were processed as described in Example 20 to provide the title compound.

EXAMPLE 78

N-{(3R)-1-[3-(4-acetylphenoxy)propyl] pyrrolidinyl}-1-[3-chloro-5-(trifluoromethyl)-2-pyridinyl]-1H-pyrrole-2-sulfonamide 1-(4-{3-[(3R)-3-Aminopyrrolidinyl]propoxy}phenyl) ethanone and 1-[3-chloro-5-(trifluoromethyl)-2-pyridinyl]-1H-pyrrole-2-sulfonyl chloride were processed as described in Example 20 to provide the title compound.

EXAMPLE 79

N-{(3R)-1-[3-(4-acetylphenoxy)propyl] pyrrolidinyl}-4-{[3-chloro-5-(trifluoromethyl)-2-pyridinyl]oxy}benzenesulfonamide 1-(4-{3-[(3R)-3-Aminopyrrolidinyl]propoxy}phenyl) ethanone and 4-{[3-chloro-5-(trifluoromethyl)-2-pyridinyl]

oxy}benzenesulfonyl chloride were processed as described in Example 20 to provide the title compound.

EXAMPLE 80

N-((3R)-1-{3-[4-(cyclopropylcarbonyl)phenoxy]
propyl}pyrrolidinyl)-1-methyl-1H-imidazole-4-
sulfonamide (4-{3-[(3R)-3-Aminopyrrolidinyl]propoxy}phenyl)
(cyclopropyl)methanone and 1-methyl-1H-imidazole-4-sulfonyl chloride were processed as described in Example 20 to provide the title compound.

EXAMPLE 81

N-((3R)-1-{3-[4-(cyclopropylcarbonyl)phenoxy]
propyl}pyrrolidinyl)-2-thiophenesulfonamide (4-{3-[(3R)-3-Aminopyrrolidinyl]propoxy}phenyl)
(cyclopropyl)methanone and 2-thiophenesulfonyl chloride were processed as described in Example 20 to provide the title compound.

EXAMPLE 82

5-chloro-N-((3R)-1-{3-[4-(cyclopropylcarbonyl)
phenoxy]propyl}pyrrolidinyl)-3-methyl-1-
benzothiophene-2-sulfonamide (4-{3-[(3R)-3-Aminopyrrolidinyl]propoxy}phenyl)
(cyclopropyl)methanone and 5-chloro-3-methyl-1-benzothiophene-2-sulfonyl chloride were processed as described in Example 20 to provide the title compound.

EXAMPLE 83

N-((3R)-1-{3-[4-(cyclopropylcarbonyl)phenoxy]
propyl}pyrrolidinyl)-3,5-bis(trifluoromethyl)
benzenesulfonamide (4-{3-[(3R)-3-Aminopyrrolidinyl]propoxy}phenyl)
(cyclopropyl)methanone and 3,5-bis(trifluoromethyl)
benzenesulfonyl chloride were processed as described in Example 20 to provide the title compound.

EXAMPLE 84

N-((3R)-1-{3-[4-(cyclopropylcarbonyl)phenoxy]
propyl}pyrrolidinyl)-8-quinolinesulfonamide (4-{3-[(3R)-3-Aminopyrrolidinyl]propoxy}phenyl)
(cyclopropyl)methanone and 8-quinolinesulfonyl chloride were processed as described in Example 20 to provide the title compound.

EXAMPLE 85

4-butoxy-N-((3R)-1-{3-[4-(cyclopropylcarbonyl)
phenoxy]propyl}pyrrolidinyl)benzenesulfonamide (4-{3-[(3R)-3-Aminopyrrolidinyl]propoxy}phenyl)
(cyclopropyl)methanone and 4-butoxybenzenesulfonyl chloride were processed as described in Example 20 to provide the title compound.
MS (ESI+) m/z 501 (M+H)$^+$; $^1$H NMR (300 MHz, DMSO-d$_6$) δ 8.0 (d, 2H), 7.65 (d, 2H), 7.6 (d, 1H), 7.15 (d, 2H), 7.0 (d, 2H), 4.1 (m, 4H), 3.6 (m, 1H), 2.8 (m H), 2.2 (m, 1H), 1.65–1.8 (m, 6H), 1.4 (m, 3H), 1.00 (d, 4H), 0.95 (t, 3

EXAMPLE 86

N-((3R)-1-{3-[4-(cyclopropylcarbonyl)phenoxy]
propyl}pyrrolidinyl)-3,4-
dimethoxybenzenesulfonamide ((4-{3-[(3R)-3-Aminopyrrolidinyl]propoxy}phenyl)
(cyclopropyl)methanone and 3,4-dimethoxybenzenesulfonyl chloride were processed as described in Example 20 to provide the title compound.

EXAMPLE 87

3-chloro-N-((3R) 1-{3-[4-(cyclopropylcarbonyl)
phenoxy]propyl}pyrrolidinyl)-4-
methylbenzenesulfonamide (4-{3-[(3R)-3-Aminopyrrolidinyl]propoxy}phenyl)
(cyclopropyl)methanone and 3-chloro-4-methylbenzenesulfonyl chloride were processed as described in Example 20 to provide the title compound.

EXAMPLE 88

N-((3R)-1-{3-[4-(cyclopropylcarbonyl)phenoxy]
propyl}pyrrolidinyl)-2-phenylethenesulfonamide (4-{3-[(3R)-3-Aminopyrrolidinyl]propoxy}phenyl)
(cyclopropyl)methanone and 2-phenylethenesulfonyl chloride were processed as described in Example 20 to provide the title compound.

EXAMPLE 89

N-((3R)-1-{3-[4-(cyclopropylcarbonyl)phenoxy]
propyl}pyrrolidinyl)-2-(trifluoromethoxy)
benzenesulfonamide (4-{3-[(3R)-3-Aminopyrrolidinyl]propoxy}phenyl)
(cyclopropyl)methanone and 2-(trifluoromethoxy)
benzenesulfonyl chloride were processed as described in Example 20 to provide the title compound.

EXAMPLE 90

2-cyano-N-((3R)-1-{3-[4-(cyclopropylcarbonyl)
phenoxy]propyl}pyrrolidinyl)benzenesulfonamide (4-{3-[(3R)-3-Aminopyrrolidinyl]propoxy}phenyl)
(cyclopropyl)methanone and 2-cyanobenzenesulfonyl chloride were processed as described in Example 20 to provide the title compound.

EXAMPLE 91

N-((3R)-1-{3-[4-(cyclopropylcarbonyl)phenoxy]
propyl}pyrrolidinyl)-3-methylbenzenesulfonamide (4-{3-[(3R)-3-Aminopyrrolidinyl]propoxy}phenyl)
(cyclopropyl)methanone and 3-methylbenzenesulfonyl chloride were processed as described in Example 20 to provide the title compound.

EXAMPLE 92

N-((3R)-1-{3-[4-(cyclopropylcarbonyl)phenoxy]
propyl}pyrrolidinyl)-4-(trifluoromethyl)
benzenesulfonamide (4-{3-[(3R)-3-Aminopyrrolidinyl]propoxy}phenyl)
(cyclopropyl)methanone and 4-trifluoromethylbenzenesulfonyl chloride were processed as described in Example 20 to provide the title compound.

EXAMPLE 93

N-((3R)-1-{3-[4-(cyclopropylcarbonyl)phenoxy]
propyl}pyrrolidinyl)-3-fluorobenzenesulfonamide (4-{3-[(3R)-3-Aminopyrrolidinyl]propoxy}phenyl)
(cyclopropyl)methanone and 3-fluorobenzenesulfonyl chloride were processed as described in Example 20 to provide the title compound.

EXAMPLE 94

N-((3R)-1-{3-[4-(cyclopropylcarbonyl)phenoxy]propyl}pyrrolidinyl)-4-(trifluoromethoxy)benzenesulfonamide (4-{3-[(3R)-3-Aminopyrrolidinyl]propoxy}phenyl)(cyclopropyl)methanone and 4-(trifluoromethoxy)benzenesulfonyl chloride were processed as described in Example 20 to provide the title compound.

EXAMPLE 95

N-((3R)-1-{3-[4-(cyclopropylcarbonyl)phenoxy]propyl}pyrrolidinyl)-8-isoguinolinesulfonamide (4-{3-[(3R)-3-Aminopyrrolidinyl]propoxy}phenyl)(cyclopropyl)methanone and 8-isoquinolinesulfonyl chloride were processed as described in Example 20 to provide the title compound.

EXAMPLE 96

N-(2-chloro-4-{[((3R)-1-{3-[4-(cyclopropylcarbonyl)phenoxy]propyl}pyrrolidinyl)aminol]sulfonyl{phenyl)acetamide (4-{3-[(3R)-3-Aminopyrrolidinyl]propoxy}phenyl)(cyclopropyl)methanone and 4-(acetylamino)-3-chlorobenzenesulfonyl chloride were processed as described in Example 20 to provide the title compound.

EXAMPLE 97

3,4-dichloro-N-((3R)-1-{3-[4-(cyclopropylcarbonyl)phenoxy]propyl}pyrrolidinyl)benzenesulfonamide (4-{3-[(3R)-3-Aminopyrrolidinyl]propoxy}phenyl)(cyclopropyl)methanone and 3,4-dichlorobenzenesulfonyl chloride were processed as described in Example 20 to provide the title compound.

EXAMPLE 98

Tert-butyl 1-{3-[(4'-cyano[1,1'-biphenyl]-4-yl)oxy]propyl}-3-pyrrolidinylcarbamate 4'-{3-[(3R)-3-Aminopyrrolidinyl]propoxy}[1,1'-biphenyl]-4-carbonitrile and tert-butyl pyrrolidinylcarbamate were processed as described in Examples 9A-9C to provide the title compound.

EXAMPLE 99

4'-{3-[(3R)-3-aminopyrrolidinyl]propoxy}[1,1'-biphenyl]-4-carbonitrile

4'-Hydroxy[1,1'-biphenyl]-4-carbonitrile was processed as described in Examples 9A-C to provide the title compound.
MS (APCI+) m/z 322 (M+H)+; $^1$H NMR (300 MHz, CDCl$_3$) δ 1.25 (m, 1H), 1.80 (m, 1H), 1.99–2.20 (m, 2H), 2.74–3.09 (m, 4H), 3.20 (m, 1H), 3.78 (m, 1H), 4.08 (t, 2H, J=8.5 Hz), 4.39–5.03 (m, 2H), 6.97 (d, 2H, J=8.8 Hz), 7.52 (d, 2H, J=8.5 Hz), 7.62 (d, 2H, J=8.5 Hz), 7.69 (d, 2H, J=8.5 Hz).

EXAMPLE 100

Tert-butyl (3S)-1-{2-[(4'-cyano[1,1'-biphenyl]-4-yl)oxy]ethyl}pyrrolidinylcarbamate 4'-Hydroxy[1,1'-biphenyl]-4-carbonitrile, 1-bromo-2-chloroethane and tert-butyl (3S)-pyrrolidinylcarbamate were processed as described in Examples 9A and 9B to provide the title compound.

EXAMPLE 101

4-methoxy-N-((3R)-1-{3-[4-(2-pyridinyl)phenoxy]propyl}pyrrolidinyl)benzenesulfonamide (3R)-1-{3-[4-(2-Pyridinyl)phenoxy]propyl}pyrrolidinylamine and 4-methoxybenzenesulfonyl chloride were processed as described in Example 20 to provide the title compound.

EXAMPLE 102

4-isopropyl-N-((3R)-1-{3-[4-(2-pyridinyl)phenoxy]propyl}pyrrolidinyl)benzenesulfonamide

EXAMPLE 102A (3R)-1-{3-[4-(2-Pyridinyl)phenoxy]propyl}pyrrolidinylamine 4-(2-Pyridinyl)phenol was processed as described in Examples 9A-9C to provide the title compound.
MS (ESI+) m/z 298 (M+H)+; $^1$H NMR (300 MHz, DMSO-d$_6$) δ 8.45 (m, 1H), 7.75 (d, 2H), 7.6 (m, 1H), 7.55 (m, 1H), 7.1 (m, 1H), 6.9 (d, 2H), 4.25 (t, 2H), 3.7 (m, 1H), 2.5–2.3 (m, 5H), 2.10 (m, 1H), 1.8–1.6 (m, 2H), 1.4 (m, 2H).

EXAMPLE 102B 4-isopropyl-N-((3R)-1-{3-[4-(2-pyridinyl)phenoxy]propyl}pyrrolidinyl)benzenesulfonamide (3R)-1-{3-[4-(2-Pyridinyl)phenoxy]propyl}pyrrolidinylamine and 4-(2-propyl)benzenesulfonyl chloride were processed as described in Example 20 to provide the title compound.
MS (ESI+) m/z 480 (M+H)+; $^1$H NMR (300 MHz, DMSO-d$_6$) δ 8.66 (d, 1H), 7.95 (m, 2H), 7.85 (d, 1H), 7.70 (m, 3H), 7.37 (d, 1H), 7.20 (m, 1H), 6.94 (m, 3H), 4.1 (t, 2H), 3.8 (br s, 1H), 3.0 (m, 1H), 2.85 (m, 1H), 2.48–2.6 (m, 4H), 2.2 (m, 1H), 1.8–1.95 (m, 2H), 1.5 (m, 1H), 1.1 (d, 6H).

EXAMPLE 103

4-cyano-N-((3R)-1-{3-[4-(2-pyridinyl)phenoxy]propyl}pyrrolidinyl)benzenesulfonamide (3R)-1-{3-[4-(2-Pyridinyl)phenoxy]propyl}pyrrolidinylamine and 4-cyanobenzenesulfonyl chloride were processed as described in Example 20 to provide the title compound.

EXAMPLE 104

3-cyano-N-((3R)-1-{3-[4-(2-pyridinyl)phenoxy]propyl}pyrrolidinyl)benzenesulfonamide (3R)-1-{3-[4-(2-Pyridinyl)phenoxy]propyl}pyrrolidinylamine and 3-cyanobenzenesulfonyl chloride were processed as described in Example 20 to provide the title compound.
MS (ESI+) m/z 463 (M+H)+; $^1$H NMR (300 MHz, DMSO-d$_6$) δ 8.56 (d, 1H), 8.21 (d, 1H), 8.18 (s, 1H), 7.88 (d, 2H), 7.72 (m, 1H), 7.5 (m, 2H), 7.45 (m, 1H), 7.0 (m, 1H), 6.85 (d, 2H), 4.1 (t, 2H), 3.6 (m, 1H), 2.8 (m, 2H), 2.4–2.5 (m, 2H), 2.2 (m, 1H), 1.8–1.9 (m,4H), 1.45 (m, 1H).

EXAMPLE 105

1-methyl-N-((3R)-1-{3-[4-(2-pyridinyl)phenoxy]propyl}pyrrolidinyl)-1H-imidazol-4-sulfonamide (3R)-1-{3-[4-(2-Pyridinyl)phenoxy]propyl}pyrrolidinylamine and 1-methyl-1H-imidazole-4- sulfonyl chloride were processed as described in Example 20 to provide the title compound.

EXAMPLE 106

3,4-dimethoxy-N-((3R)-1-{3-[4-(2-pyridinyl) phenoxy]propyl}pyrrolidinyl)benzenesulfonamide (3R)-1-{3-[4-(2-Pyridinyl)phenoxy] propyl}pyrrolidinylamine and 1-methyl-1H-imidazole-4-sulfonyl chloride were processed as described in Example 20 to provide the title compound.

EXAMPLE 107

N-(2-chloro-4-{[((3R)-1-{3-[4-(2-pyridinyl) phenoxy]propyl}pyrrolidinyl)amino] sulfonyl}phenyl)acetamide (3R)-1-{3-[4-(2-Pyridinyl)phenoxy] propyl}pyrrolidinylamine and 4-(acetylamino)-3-chlorobenzenesulfonyl chloride were processed as described in Example 20 to provide the title compound.

EXAMPLE 108

4'-{3-[(3R)-3-(dimethylamino)pyrrolidinyl]propoxy} [1,1'-biphenyl]-4-carbonitrile 4'-{3-[(3R)-3-Aminopyrrolidinyl]propoxy}[1,1'-biphenyl]-4-carbonitrile (200 mg, 0.74 mmol), N,N-dimethyl-N-[(3R)-pyrrolidinyl]amine (85 mg, 0.74 mmol), 250 mg of potassium carbonate and 300 mg of potassium iodide in 20 mL of 2-butanone were heated at 110° C. for 72 hours. The mixture was evaporated under reduced pressure and the residue was purified by chromatography (CHCl$_3$:MeOH:NH$_4$OH, 9:1:0.1) to provide the title compound.
MS (ESI+) m/z 350 (M+H)$^+$; $^{13}$C NMR(500 MHz, CD$_3$OD) 29.3, 29.6, 43.9, 54.2, 54.3, 59.6, 66.5, 67.3, 111.0, 116.2, 119.9, 128.2, 129.4, 132.7, 133.7, 146.7, 161.2; $^1$H NMR (500 MHz, CD$_3$OD) 1.74 (m, 1H), 2.0 (m, 2H), 2.02 (m, 1H) 2.23 (s, 6H), 2.32 (m, 1H), 2.51 (m, 1H), 2.62 (m, 1H), 2.71 (m, 1H), 2.84 (m, 2H), 2.97 (m, 1H), 4.08 (t, J=7 Hz, 2H), 7.02 (d, J=11 Hz, 2H), 7.61 (d, J=11 Hz, 2H), 7.74 (s, 4H).

EXAMPLE 109

Tert-butyl (3R)-1-f3-[(4'-cyano[1,1'-biphenyl]-4-yl) oxy]propyl}pyrrolidinyl(methyl)carbamate 4'-{3-[(3R)-3-Aminopyrrolidinyl]propoxy}[1,1'-biphenyl]-4-carbonitrile (2.31 g, 8.54 mmol), tert-butyl methyl[(3R)-pyrrolidinyl]carbamate (1.71 g, 8.54 mmol), potassium carbonate (2.95 g, 21.34 mmol) and potassium iodide (3.54 g, 21.34 mmol) in 75 mL of 2-butanone were heated at 115° C. for 72 hours. The mixture was evaporated under reduced pressure and the residue was purified by chromatography (CHCl$_3$:MeOH:NH$_4$OH, 9:1:0.1) to provide the title compound (89% yield).
MS (APCI+) m/z 436 (M+H)$^+$; $^1$H NMR (300 MHz, CDCl$_3$) δ 1.45 (s, 9H), 1.8 (m, 2H), 2.1 (m, 2H), 2.4 (m, 2H), 2.7 (m, 2H), 2.85 (s, 3H), 4.1 (t, J=7Hz, 2H), 4.25 (m, 1H), 4.75 (m, 1H), 6.98 (d, J=9Hz, 2H), 7.5 (d, J=9Hz, 2H), 7.65 (m, 4H).

EXAMPLE 110

4'-{3-[(3R)-3-(methylamino)pyrrolidinyl]propoxy} [1,1'-biphenyl]-4-carbonitrile

The product from Example 109 (3.3 g, 7.58 mmol) in dichloromethane (100 mL) was treated with trifluoroacetic acid (6.0 ml) at 0° C. After stirring at ambient temperature for 18 hours, the mixture was evaporated under reduced pressure. The residue was partitioned between saturated aqueous sodium bicarbonate (2×30 mL) and dichloromethane (150 mL). The organic layer was washed with brine (50 mL), dried over sodium sulfate and filtered. The filtrate was evaporated under reduced pressure and the residue purified by chromatography (CHCl$_3$:MeOH:NH$_4$OH, 9:1:0.1) to provide the title compound (95% yield).
MS (APCI+) m/z 336 (M+H)$^+$; $^1$H NMR (300 MHz, CDCl$_3$) δ 1.62 (m, 1H), 2.00 (m, 2H), 2.13 (m, 1H), 2.26 (m, 1H), 2.41 (s, 3H), 2.43–2.83 (m, 5H), 3.25 (m, 1H), 4.08 (t, 2H, J=6.3 Hz), 6.99 (d, 2H, J=8.9 Hz), 7.52 (d, 2H, J=8.8 Hz), 7.66 (dd, 4H, J=16.8, 8.6Hz).

EXAMPLE 111

N-((3R)-1-{3-[(4'-cyano[1,1'-biphenyl]-4-yl)oxy] propyl}pyrrolidinyl)-N-methylacetamide The product from Example 110 (50 mg, 0.15 mmol), acetic anhydride (0.021 ml, 0.22 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (60% yield).
MS (APCI+) m/z 378 (M+H)$^+$; $^1$H NMR (300 MHz, CDCl$_3$) δ 2.12 (m, 5H), 2.32 (m, 7H), 2.65 (s, 3H), 2.83–3.18 (m, 7H), 3.23–3.79 (m, 9H), 3.87–4.20 (m, 7H), 5.38 (m, 1H), 5.64–5.94 (m, 1H), 6.97 (m, 2H), 7.53 (d, 2H, J=8.8 Hz), 7.66 (dd, 4H, J=20.2, 8.6 Hz).

EXAMPLE 112

N-((3R)-1-{3-[(4'-cyano 1,1'-biphenyl]-4-yl)oxy] propyl}pyrrolidinyl)-N,3,3-trimethylbutanamide The product from Example 110 (50 mg, 0.15 mmol), tert-butylacetyl chloride (0.031 ml, 0.22 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 434 (M+H)$^+$; $^1$H NMR (300 MHz, CDCl$_3$) δ 1.05 (s, 9H), 2.11–2.41 (m, 5H), 2.90 (m, 1H), 3.08 (m, 3H), 3.24–3.47 (m, 3H), 3.57–3.80 (m, 2H), 3.94 (m, 1H), 4.12 (m, 3H), 6.97 (m, 2H), 7.53 (d, 2H, J=8.8 Hz), 7.66 (dd, 4H, J=20.3, 8.8 Hz).

EXAMPLE 113 methyl (3R)-1-{3-[(4'-cyano[1,1'-biphenyl]-4-yl) oxy]propyl}pyrrolidinyl(methyl)carbamate The product from Example 110 (50 mg, 0.15 mmol), dimethyl dicarbonate (0.024 ml, 0.22 mmol), and N,N-diisopropylethylamine (50 μL, 0.3 mmol) in 2 mL of dichloromethane were stirred at 20° C. for 18 hours. The mixture was evaporated under reduced pressure and the residue was purified by chromatography (CHCl$_3$/MeOHiNH$_4$OH, 9:1:0.1) to provide the title compound (60% yield).
MS (APCI+) m/z 394 (M+H)$^+$; $^1$H NMR (300 MHz, CDCl$_3$) δ 0.89 (m, 2H), 1.30–1.52 (m, 2H), 1.44 (s, 3H), 1.77 (m, 1H), 2.15–2.38 (m, 3H), 2.65 (s, 3H), 2.91 (m, 3H), 3.18–3.52 (m, 3H), 3.73 (m, 1H), 3.84–4.04 (m, 1H), 4.05–4.26 (m, 2H), 6.97 (d, 2H, J=8,5 Hx), 7.53 (d, 2H, J=8.5 Hz), 7.66 (dd, 4H, J=20.4, 8.1 Hz).

EXAMPLE 114

Tert-pentyl (3R)-1-{3-[(4'-cyano[1,1'-biphenyl]-4-yl)oxy]propyl}pyrrolidinyl(methyl)carbamate The product from Example 110 (50 mg, 0.15 mmol), di(tert-pentyl) dicarbonate (0.055 ml, 0.22 mmol), and N,N-diisopropylethylamine (50 µL, 0.3 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (60% yield).
MS (APCI+) m/z 450 (M+H)$^+$; $^1$H NMR (300 MHz, CDCl$_3$) δ 0.90 (s, 2H), 1.45 (m, 4H), 1.80 (m, 2H), 2.3 (m, 2H), 2.5 (m, 1H), 2.7 (s, 2H), 2.85 (s, 2H), 2.95 (s, 3H), 3.4 (m, 4H), 3.75 (m, 1H), 3.95 (m, 1H), 4.15 (t, J=7Hz, 2H), 5.05 (m, 1H), 6.98 (d, J=9 Hz, 2H), 7.55 (d, J=9Hz, 2H), 7.65 (m, 4H).

EXAMPLE 115

N-((3R)-1-{3-[(4'-cyano[1,1'-biphenyl]-4-yl)oxy]propyl}pyrrolidinyl)-N,N',N'-trimethylurea The product from Example 110 (50 mg, 0.15 mmol), dimethylcarbamyl chloride (0.021 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH4OH, 9:1:0.1) to provide the title compound (62% yield).
$^1$H NMR (300 MHz, CDCl$_3$) δ 2.14–2.40 (m, 3H), 2.64 (s, 3H), 2.84 (s, 3H), 2.85 (s, 3H), 3.25–3.46 (m, 3H), 3.52 (m, 1H), 3.61–3.81 (m, 1H), 3.98 (m, 1H), 4.13 (m, 2H), 7.53–6.09 (m, 1H), 6.98 (m, 2H), 6.98 (m, 2H), 7.53 (d, 2H, J=8.8 Hz), 7.66 (dd, 4H, J=20.1, 8.6 Hz). MS (APCI+) m/z 407 (M+H)$^+$.

EXAMPLE 116

N-((3R)-1-{3-[(4'-cyano[1,1'-biphenyl]-4-yl)oxy]propyl}pyrrolidinyl)-N-methyl-1-pyrrolidinecarboxamide The product from Example 110 (50 mg, 0.15 mmol), 1-pyrrolidinecarbonyl chloride (0.030 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 433 (M+H)$^+$; $^1$H NMR (300 MHz, CDCl$_3$) δ 1.85 (m, 3H), 2.17–2.37 (m, 3H), 2.64 (m, 1H), 2.89 (m, 3H), 3.23–3.46 (m, 6H), 3.62–3.83 (m, 1H), 4.12 (m, 2H), 6.98 (dd, 2H, J=11.4, 8.6 Hz), 7.53 (d, 2H, J=8.8 Hz), 7.66 (dd, 1H, J=20.2, 8.6 Hz).

EXAMPLE 117

N'-tert-butyl-N-((3R)-1-{3-[(4'-cyano[1,1'-biphenyl]-4-yl)oxy]propyl}pyrrolidinyl)-N-methylurea The product from Example 110 (50 mg, 0.15 mmol), tert-butylcarbamyl chloride (0.026 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 435 (M+H)$^+$; $^1$H NMR (300 MHz, CDCl$_3$) δ 1.35 (s, 9H), 2.15–2.44 (m, 4H), 2.85 (s, 3H), 3.10–3.43 (m, 3H), 3.57–3.78 (m, 1H), 3.81–4.01 (m, 1H), 4.13 (m, 2H), 4.23–4.50 (m, 1H), 5.08–5.37 (m, OH), 6.98 (m, 2H), 7.53 (d, 2H, J=8.8 Hz), 7.66 (dd. 4H, J=20.3, 8.5 Hz).

EXAMPLE 118

N-((3R)-1-{3-[(4'-cyano[1,1'-biphenyl]-4-yl)oxy]propyl}pyrrolidinyl)-N-methyl-4-flouro-N-morpholinecarboxamide The product from Example 110 (50 mg, 0.15 mmol), 4-morpholinecarbonyl chloride (0.026 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 449 (M+H)$^+$; $^1$H NMR (300 MHz, CDCl$_3$) δ 2.14–2.39 (m, 3H), 2.89 (d, 3H, J=16.9 Hz), 3.12–3.56 (m, 7H), 3.61–3.82 (m, 5H), 3.87–4.22 (m, 3H), 4.42–4.65 (m, 1H), 4.70–5.24 (m, 2H), 6.97 (m, 2H), 7.53 (d, 2H, J=8.5 Hz), 7.66 (dd, 4H, J=20.3, 8.4 Hz).

EXAMPLE 119

N-((3R)-1-{3-[(4'-cyano[1,1'-biphenyl]-4-yl)oxy]propyl}pyrrolidinyl)-4-fluoro-N-methylbenzamide The product from Example 110 (50 mg, 0.15 mmol), 4-fluorobenzoyl chloride (0.026 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 458 (M+H)$^+$; $^1$H NMR (300 MHz, CDCl$_3$) δ 2.22–2.58 (m, 3H), 2.64 (s, 3H), 2.93–3.19 (m, 3H), 3.27–3.94 (m, 5H), 3.96–4.22 (m, 3H), 4.23–4.58 (m, 1H), 6.89 (d, 2H, J=8.4 Hz), 7.13 (t, 2H, J=8.5 Hz), 7.44 (dd, 2H, J=8.8, 5.5 Hz), 7.53 (d, 2H, J=8.9 Hz), 7.66 (dd, 4H, J=20.7, 8.8 Hz).

EXAMPLE 120

4-cyano-N-((3R)-1-{3-[(4'-cyano[1,1'-biphenyl]-4-yl)oxy]propyl}pyrrolidinyl)-N-methylbenzamide The product from Example 110 (50 mg, 0.15 mmol), 4-cyanobenzoyl chloride (37 mg, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH4OH, 9:1:0.1) to provide the title compound (62% yield).
MS (APCI+) m/z 465 (M+H)$^+$; $^1$H NMR (300 MHz, CDCl$_3$) δ 2.18–2.56 (m, 4H), 2.63 (s, 3H), 2.89–3.17 (m, 4H), 3.29–3.60 (m, 4H), 3.72–3.96 (m, 1H), 4.03–4.24 (m, 3H), 6.97 (d, 2H, J=8.8 Hz), 7.53 (d, 4H, J=7.1 Hz), 7.66 (dd, 4H, J=20.9, 8.2 Hz), 7.75 (d, 2H, J=8.2 Hz).

EXAMPLE 121

N-((3R)-1-{3-[(4'-cyano[1,1'-biphenyl]-4-yl)oxy]propyl}pyrrolidinyl)-N-methylnicotinamide The product from Example 110 (50 mg, 0.15 mmol), nicotinoyl chloride (40 mg, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 441 (M+H)$^+$; $^1$H NMR (300 MHz, CDCl$_3$) δ 2.20–2.61 (m, 3H), 2.66 (s, 2H), 2.91–3.24 (m, 3H), 3.24–3.76 (m, 4H), 3.77–3.97 (m, 1H), 3.99–4.27 (m, 3H), 6.98 (d, 2H, J=8.5 Hz), 7.53 (d, 2H, J=8.8 Hz), 7.66 (dd, 4H, J=20.1, 8.2 Hz), 7.86–8.07 (m, 1H), 8.08–8.50 (m, 1H), 8.78 (d, 2H, J=14.6 Hz).

EXAMPLE 122

N-((3R)-1-{3-[(4'-cyano[1,1'-biphenyl]-4-yl)oxy]propyl}pyrrolidinyl)-N-methyl-2-furamide The product from Example 110 (50 mg, 0.15 mmol), 2-furoyl chloride (0.022 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 430 (M+H)$^+$; $^1$H NMR (300 MHz, CDCl$_3$) δ 2.19–2.60 (m, 4H), 2.64 (s, 3H), 3.19–3.61 (m, 6H), 3.62–3.88 (m, 2H), 3.90–4.21 (m, 4H), 6.53 (dd, 1H, J=3.4, 1.7 Hz), 6.98 (d, 2H, J=8.1 Hz), 7.06 (m, 1H), 7.53 (d, 2H, J=8.8 Hz), 7.67 (dd, 4H, J=20.0, 8.8 Hz).

EXAMPLE 123

N-((3R)-1-{3-[(4'-cyano[1,1'-biphenyl]-4-yl)oxy]propyl}pyrrolidinyl)-N-methyl-2-(3-pyridinyl)-1,3-thiazole-4-carboxamide The product from Example 110 (50 mg, 0.15 mmol), 2-(3-pyridinyl)-1,3-thiazole-4-carbonyl chloride (46 mg, 0.22 mmol), and N,N-diisopropylethylamine (50 µL, 0.3 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 524 (M+H)$^+$; $^1$H NMR (300 MHz, CDCl$_3$) δ 2.20 (m, 2H), 2.35 (m, 4H), 2.65 (s, 3H), 3.10 (m, 2H), 3.40 (m, 4H), 4.15 (m, 2H), 6.98 (d, J=9Hz, 2H), 7.50 (d, J=9 Hz, 2H), 7.65 (m, 4H), 8.05 (s, 1H), 8.40 (m, 1H), 8.70 (m, 1H), 9.20 (m, 1H).

EXAMPLE 124

N-[(3R)-1-[3-[(4'-cyano[1,1'-biphenyl]-4-yl)oxy]propyl]pyrrolidinyl]-N,N',N'-trimethyl-sulfamide The product from Example 110 (50 mg, 0.15 mmol), dimethylsulfamoyl chloride (0.024 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 443 (M+H)$^+$; $^1$H NMR (300 MHz, CDCl$_3$) δ 2.15–2.56 (m, 4H), 2.65 (s, 3H), 2.71–2.92 (m, 2H), 2.83 (s, 6H), 2.97 (m, 1H), 3.18 (m, 1H), 3.36 (m, 2H), 3.85 (m, 1H), 4.12 (m, 2H), 6.97 (d, 2H, J=8.9 Hz), 7.53 (d, 2H, J=8.8 Hz), 7.66 (dd, 4H, J=20.3, 8.4 Hz).

EXAMPLE 125

N-((3R)-1-{3-[(4'-cyano[1,1'-biphenyl]-4-yl)oxy]propyl}pyrrolidinyl)-3-fluoro-N-methylbenzenesulfonamide The product from Example 110 (50 mg, 0.15 mmol), 3-fluorobenzenesulfonyl chloride (0.039 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 494 (M+H)$^+$; $^1$H NMR (300 MHz, CDCl$_3$) δ 1.96–2.43 (m, 3H), 2.64 (s, 2H), 2.73–2.94 (m, 3H), 3.07 (m, 1H), 3.21–3.43 (m, 2H), 4.10 (m, 2H), 6.95 (d, 2H, J=8.8 Hz), 7.34 (m, 1H), 7.53 (d, 2H, J=8.8 Hz), 7.58 (m, 1H), 7.66 (dd, 4H, J=21.2, 8.3 Hz).

EXAMPLE 126

4-cyano-N-((3R)-1-{3-[(4'-cyano[1,1'-biphenyl]-4-yl)oxy]propyl}pyrrolidinyl)-N-methylbenzenesulfonamide The product from Example 110 (50 mg, 0.15 mmol), 4-cyanobenzenesulfonyl chloride (45 mg, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 501 (M+H)$^+$; $^1$H NMR (300 MHz, CDCl$_3$) δ 2.30 (m, 2H), 2.65 (s, 3H), 2.77–3.01 (m, 2H), 3.09 (m, OH), 3.23–3.43 (m, 2H), 4.11 (m, 1H), 6.95 (d, 2H, J=8.8 Hz), 7.54 (d, 2H, J=8.9 Hz), 7.67 (dd, 4H, J=21.2, 8.3 Hz), 7.89 (dd, 4H, J=23.9, 8.3 Hz).

EXAMPLE 127

N-((3R)-1-{3-[(4'-cyano[1,1'-biphenyl]-4-yl)oxy]propyl}pyrrolidinyl)-4-isopropyl-N-methylbenzenesulfonamide The product from Example 110 (50 mg, 0.15 mmol), 4-(2-propyl)benzenesulfonyl chloride (0.044 ml, 0.22 mmol), and N,N-diisopropylethylamine (50 µL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 518 (M+H)$^+$; $^1$H NMR (300 MHz, CDCl$_3$) δ 1.27 (d, 6H, J=6.7 Hz), 2.11–2.40 (m, 3H), 2.64 (s, 3H), 2.79 (m, 3H), 2.84–3.14 (m, 2H), 3.20–3.43 (m, 2 H), 4.10 (m, 2H), 6.95 (d, 2H, J=8.8 Hz), 7.38 (d, 2H, J=8.2 Hz), 7.52 (d, 2H, J=8.5 Hz), 7.66 (dd, 4H, J=21.4, 8.5 Hz), 7.70 (d, 2H, J=8.2 Hz).

EXAMPLE 128

N-((3R)-1-{3-[(4'-cyano[1,1'-biphenyl]-4-yl)oxy]propyl}pyrrolidinyl)-N-methyl-4-(methylsulfonyl)benzenesulfonamide The product from Example 110 (50 mg, 0.15 mmol), 4-(methylsulfonyl)benzenesulfonyl chloride (57 mg, 0.22 mmol), and N,N-diisopropylethylamine (50 μL, 0.3 mmol) in 2 nIL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (68% yield).
MS (APCI+) m/z 554 (M+H)$^+$; $^1$H NMR (300 MHz, CDCl$_3$) δ 2.30 (m, 4H), 2.60 (s, 3H), 2.90 (s, 2H), 3.10 (s, 3H), 3.30 (m, 2H), 4.10 (t, J=7Hz, 2H), 4.95 (m, 1H), 6.95 (d, J=9 Hz, 2H), 7.50 (d, J=9Hz, 2H), 7.65 (m, 4H), 8.00 (d, J=9Hz, 2H), 8.15 (d, J=9 Hz, 2H).

EXAMPLE 129

N-((3R)-1-{3-[(4'-cyano[1,1'-biphenyl]-4-yl)oxy]propyl}pyrrolidinyl)-4-fluoro-N-(4-fluorobenzoyl)benzamide 4'-{3-[(3R)-3-Aminopyrrolidinyl]propoxy}[1,1'-biphenyl]-4-carbonitrile (50 mg, 0.15 mmol), 4-fluorobenzoyl chloride (0.028 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (20% yield).
MS (APCI+) m/z 436 (M+H)$^+$; $^1$H NMR (300 MHz, CDCl$_3$) δ 2.24–2.56 (m, 4H), 2.56–2.84 (m, 1H), 3.11–3.45 (m, 1H), 3.45–3.78 (m, 4H), 3.93 (m, 1H), 4.12 (m, 2H), 4.27 (m, 1H), 5.35–5.62 (m, 1H), 6.82–7.04 (m, 6H), 7.44 (m, 4H), 7.52 (d, 2H, J=8.8 Hz), 7.65 (dd, 4H, J=20.0, 8.2 Hz).

EXAMPLE 130

N-((3R)-1-{3-[(4'-cyano[1,1'-biphenyl]-4-yl)oxy]propyl}pyrrolidinyl)acetamide

4'-{3-[(3R)-3-Aminopyrrolidinyl]propoxy}[1,1'-biphenyl]-4-carbonitrile (50 mg, 0.15 mmol), acetyl chloride (22.0 μl, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (70% yield).
MS (APCI+) m/z 364 (M+H)$^+$; $^1$H NMR (300 MHz, CDCl$_3$) δ 2.0 (m, 3H), 2.2–2.6 (m, 4H), 2.9–3.2 (m, 2H), 3.35 (m, 2H), 3.75 (m, 1H), 4.0 (m, 1H), 4.15 (m, 2H), 4.9 (m, 1H), 6.95 (d, J=9 Hz, 2H), 7.50 (d, J=9 Hz, 2H), 7.65 (m, 4H), 8.3 (m, 2H).

EXAMPLE 131

N-((3R)-1-{3-[(4'-cyano[1,1'-biphenyl]-4-yl)oxy]propyl}pyrrolidinyl)-3,3-dimethylbutanamide 4'-{3-[(3R)-3-Aminopyrrolidinyl]propoxy}[1,1'-biphenyl]-4-carbonitrile (50 mg, 0.15 mmol), tert-butylacetyl chloride (0.033 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH4OH, 9:1:0.1) to provide the title compound (52% yield).
MS (APCI+) m/z 420 (M+H)$^+$; $^1$H NMR (300 MHz, CDCl$_3$) δ 1.02 (s, 9H), 2.10 (s, 2H), 2.21 (m, 1H), 2.35 (m, 2H), 2.42–2.81 (m, 6H), 2.83–3.17 (m, 2H), 3.35 (m, 2H), 3.97 (m, 1H), 4.13 (m, 2H), 4.92 (m, 1H), 6.97 (d, 2H, J=8.8 Hz), 7.54 (d, 2H, J=8.5 Hz), 7.67 (dd, 4H, J=21.8, 8.3 Hz).

EXAMPLE 132

Allyl (3R)-1-{3-[(4'-cyano[1,1'-biphenyl]-4-yl)oxy]propyl}pyrrolidinylcarbamate

4'-{3-[(3R)-3-Aminopyrrolidinyl]propoxy}[1,1'-biphenyl]-4-carbonitrile (50 mg, 0.15 mmol), allyl chloroformate (0.039 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (51% yield).
MS (APCI+) m/z 406 (M+H)$^+$; $^1$H NMR (300 MHz, CDCl$_3$) δ 2.17–2.41 (m, 4H), 2.41–2.64 (m, 6H), 2.91 (m, 1H), 3.10 (m, 1H), 3.23–3.46 (m, 2H), 3.81 (m, 2H), 4.00 (m, 1H), 4.14 (m, 2H), 4.56 (m, 2H), 4.68 (m, 1H), 5.20 (dd, 1H, J=10.3, 0.8 Hz), 5.30 (dd, 1H, J=17.3, 1.4 Hz), 5.90 (ddd, 1H, J=22.8, 10.7, 5.7 Hz), 6.80 (m, IH), 6.97 (d, 2H, J=8.8 Hz), 7.53 (d, 2H, J=8.4 Hz), 7.67 (dd, 4H, J=21.6, 8.7 Hz).

EXAMPLE 133

Methyl (3R)-1-{3-[(4'-cyano[1,1'-biphenyl]-4-yl)oxy]propyl}pyrrolidinylcarbamate 4'-{3-[(3R)-3-Aminopyrrolidinyl]propoxy}[1,1'-biphenyl]-4-carbonitrile (50 mg, 0.15 mmol), methyl chloroformate (0.025 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (51% yield).
MS (APCI+) m/z 380 (M+H)$^+$; $^1$H NMR (300 MHz, CDCl$_3$) δ 2.05 (m, 6H), 2.29 (m, 3H), 2.53 (m, 1H), 3.08 (m, 1H), 3.33 (m, 2H), 3.67 (s, 3H), 3.77 (m, 1H), 3.98 (m, 1H), 4.14 (t, 2H, J=5.6 Hz), 4.67 (m, 1H), 6.96 (d, 2H, J=8.8 Hz), 7.53 (d, 2H, J=9.2 Hz), 7.67 (dd, 4H, J=21.6, 8.6 Hz).

EXAMPLE 134

Tert-pentyl (3R)-1-{3-[(4'-cyano[1,1'-biphenyl]-4-yl)oxy]propyl}pyrrolidinylcarbamate 4'-{3-[(3R)-3-Aminopyrrolidinyl]propoxy}[1,1'-biphenyl]-4-carbonitrile (50 mg, 0.15 mmol), 1,1-dimethylpropyl chloroformate (57.1 μL, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (72% yield).
MS (APCI+) m/z 436 (M+H)$^+$; $^1$H NMR (300 MHz, CDCl$_3$) δ 0.90 (t, J=7 Hz, 3H), 1.4 (s, 6H), 1.75 (m, 2H), 2.2 (m, 1H), 2.35 (m, 2H), 2.5 (m, 1H), 2.9 (m, 4H), 3.35 (m, 2H), 3.7 (m, 1H), 4.0 (m, 1H), 4.15 (m, 2H), 6.95 (d, J=9 Hz, 2H), 7.50 (d, J=9 Hz, 2H), 7.65 (m, 4H).

EXAMPLE 135

N'-((3R)-1-{3-[(4'-cyano[1,1'-biphenyl]-4-yl)oxy]propyl}pyrrolidinyl)-N,N-dimethylurea 4'-{3-[(3R)-3-Aminopyrrolidinyl]propoxy}[1,1'-biphenyl]-4-carbonitrile (50 mg, 0.15 mmol), dimethylcarbamyl chloride (0.021 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (65% yield).
MS (APCI+) m/z 393 (M+H)$^+$; $^1$H NMR (300 MHz, CDCl$_3$) δ 2.20–2.42 (m, 4H), 2.48–2.77 (m, 6H), 2.90 (m, 1H), 2.93 (s, 6H), 3.07 (m, 1H), 3.34 (m, 2H), 3.76 (m, 1H), 3.96 (m, 1H), 4.14 (t, 2H, J=5.4 Hz), 4.86 (m, 1H), 6.71 (m, 1H), 6.97 (d, 2H, J=8.8 Hz), 7.53 (d, 2H, J=8.8 Hz), 7.67 (dd, 4H, J=21.8, 8.7 Hz).

EXAMPLE 136

N-((3R)-1-{3-[(4'-cyano[1,1'-biphenyl]-4-yl)oxy]propyl}pyrrolidinyl)-1-pyrrolidinecarboxamide 4'-{3-[(3R)-3-Aminopyrrolidinyl]propoxy}[1,1'-biphenyl]-4-carbonitrile (50 mg, 0.15 mmol), 1-pyrrolidinecarbonyl chloride (0.031 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (68% yield).
MS (APCI+) m/z 419 (M+H)$^+$; $^1$H NMR (300 MHz, CDCl$_3$) δ 1.90 (m, 4H), 2.21–2.43 (m, 3H), 2.59 (m, 1H), 2.83–3.50 (m, 12H), 3.77 (m, 1H), 3.97 (m, 1H), 4.15 (t, 2H, J=4.8 Hz), 4.89 (m, 1H), 6.59 (m, 1H), 6.97 (d, 2H, J=8.4 Hz), 7.53 (d, 2H, J=8.5 Hz), 7.67 (dd, 4H, J=21.7, 8.5 Hz).

EXAMPLE 137

N-(tert-butyl)-N'-((3R)-1-{3-[(4'-cyano[1,1'-biphenyl]-4-yl)oxy]propyl}pyrrolidinyl)

4'-{3-[(3R)-3-Aminopyrrolidinyl]propoxy}[1,1'-biphenyl]-4-carbonitrile (50 mg, 0.15 mmol), tert-butylcarbamyl chloride (0.027 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (65% yield).
MS (APCI+) m/z 421 (M+H)$^+$; $^1$H NMR (300 MHz, CDCl$_3$) δ 1.31 (s, 9H), 2.16 (m, 1H), 2.35 (m, 2H), 2.50 (m, 1H), 2.61–3.08 (m, 4H), 3.33 (m, 2H), 3.68 (m, 1H), 3.94 (m, 1H), 4.15 (t, 2H, J=5.6 Hz), 4.74 (m, 1H), 6.97 (d, 2H, J=8.8 Hz), 7.54 (d, 2H, J=9.2 Hz), 7.67 (dd, 4H, J=21.7, 8.8 Hz).

EXAMPLE 138

N-((3R)-1-{3-[(4'-cyano[1,1'-biphenyl]-4-yl)oxy]propyl}pyrrolidinyl)-4-morpholinecarboxamide 4'-{3-[(3R)-3-Aminopyrrolidinyl]propoxy}[1,1'-biphenyl]-4-carbonitrile (50 mg, 0.15 mmol), 4-morpholinecarbonyl chloride (0.027 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (52% yield).
MS (APCI+) m/z 435 (M+H)$^+$; $^1$H NMR (300 MHz, CDCl$_3$) δ 2.24 (m, 1H), 2.36 (m, 2H), 2.60 (m, 2H), 2.70–3.01 (m, 4H), 3.10 (m, 1H), 3.33 (m, 2H), 3.43 (t, 4H, J=4.6 Hz), 3.67 (t, 4H, J=4.4 Hz), 3.77 (m, 1H), 3.97 (m, 1H), 4.15 (t, 2H, J=5.1 Hz), 4.88 (m, 1H), 6.97 (d, 2H, J=8.9 Hz), 7.54 (d, 2H, J=8.5 Hz), 7.67 (dd, 4H, J=22.1, 8.5 Hz).

EXAMPLE 139

N-((3R)-1-{3-[(4'-cyano[1,1'-biphenyl]-4-yl)oxy]propyl}pyrrolidinyl)-4-fluorobenzamide 4'-{3-[(3R)-3-Aminopyrrolidinyl]propoxy}[1,1'-biphenyl]-4-carbonitrile (50 mg, 0.15 mmol), 4-fluorobenzoyl chloride (0.027 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (58% yield). MS (APCI+) m/z 444 (M+H)$^+$; $^1$H NMR (300 MHz, CDCl$_3$) δ 2.36 (m, 3H), 2.58–2.88 (m, 3H), 2.99 (m, 1H), 3.18 (m, 1H), 3.29–3.50 (m, 2H), 3.90 (m, 1H), 4.03 (m, 1H), 4.16 (t, 2H, J=4.8 Hz), 5.16 (m, 1H), 6.96 (d, 2H, J=8.8 Hz), 7.11 (t, 2H, J=8.7 Hz), 7.51 (d, 2H, J=8.8 Hz), 7.66 (dd, 4H, J=24.3, 8.7 Hz), 7.66 (dd, 2H), 8.69 (d, 1H, J=7.5 Hz).

EXAMPLE 140

4-cyano-N-((3R)-1-{3-[(4'-cyano[1,1'-biphenyl]-4-yl)oxy]propyl}pyrrolidinyl)benzamide 4'-{3-[(3R)-3-Aminopyrrolidinyl]propoxy}[1,1'-biphenyl]-4-carbonitrile (50 mg, 0.15 mmol), 4-cyanobenzoyl chloride (38.6 mg, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (62% yield).
MS (APCI+) m/z 451 (M+H)$^+$; $^1$H NMR (300 MHz, CDCl$_3$) δ 2.22–2.47 (m, 6H), 2.69 (m, 1H), 3.01 (m, 1H), 3.19 (m, 1H), 3.41 (m, 2H), 3.91 (m, 1H), 4.05 (m, 1H), 4.17 (t, 2H, J=5.1 Hz), 5.18 (m, 1H), 6.96 (d, 2H, J=8.5 Hz), 7.52 (d, 2H, J=8.5 Hz), 7.66 (dd, 4H, J=24.7, 8.5 Hz), 7.73 (d, 2H, J=8.8 Hz), 8.10 (d, 2H, J=8.1 Hz), 9.05 (m, 1H).

EXAMPLE 141

N-((3R)-1-{3-[(4'-cyano[1,1'-biphenyl]-4-yl)oxy]propyl}pyrrolidinyl)nicotinamide 4'-{3-[(3R)-3-Aminopyrrolidinyl]propoxy}[1,1'-biphenyl]-4-carbonitrile (50 mg, 0.15 mmol), nicotinoyl chloride (41.5 mg, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (65% yield).
MS (APCI+) m/z 427 (M+H)$^+$; $^1$H NMR (300 MHz, CDCl$_3$) δ 2.39 (m, 3H), 2.71 (m, 3H), 3.07 (m, 1H), 3.24 (m, 1H), 3.43 (m, 2H), 3.93 (m, 1H), 4.05 (m, 1H), 4.17 (t, 2H, J=5.1 Hz), 6.96 (d, 2H, J=9.2 Hz), 7.53 (d, 2H, J=8.8 Hz), 7.66 (dd, 4H, J=24.1, 8.5 Hz), 7.77 dd,1H, J=8.2, 5.4 Hz), 8.81 (dt, 1H, J=8.1, 1.7 Hz), 8.88 (dd, 1H, J=5.5, 1.4 Hz), 9.36 (d, 1H, J=1.7 Hz), 9.60 (d, 1H, J=8.2 Hz).

EXAMPLE 142

N-((3R)-1-{3-[(4'-cyano[1,1'-biphenyl]-4-yl)oxy]propyl}pyrrolidinyl)-2-furamide

4'-{3-[(3R)-3-Aminopyrrolidinyl]propoxy}[1,1'-biphenyl]-4-carbonitrile (50 mg, 0.15 mmol), 2-furoyl chloride (0.023 ml, 0.22 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (68% yield).
MS (APCI+) m/z 416 (M+H)$^+$; $^1$H NMR (300 MHz, CDCl$_3$) δ 2.29–2.49 (m, 4H), 2.57–2.79 (m, 2H), 2.79–3.05 (m, 5H), 3.07–3.28 (m, 1H), 3.37 (m, 1H), 3.46–3.73 (m, 4H), 3.89 (m, 1H), 4.17 (m, 4H), 5.35 (m, 1H), 6.45 (m, 2H), 6.98 (m, 2H), 7.11 (d, 2H, J=3.4 Hz), 7.42 (m, 2H), 7.53 (d, 2H, J=8.8 Hz), 7.67 (dd, 4H, J=20.2, 8.3 Hz).

EXAMPLE 143

N-((3R)-1-{3-[(4'-cyano[1,1'-biphenyl]-4-yl)oxy] propyl}pyrrolidinyl)-2-(3-pyridinyl)-1,3-thiazole-4-carboxamide 4'-{3-[(3R)-3-Aminopyrrolidinyl]propoxy}[1,1'-biphenyl]-4-carbonitrile (50 mg, 0.15 mmol), 2-(3-pyridinyl)-1,3-thiazole-4-carbonyl chloride (48.1 mg, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (72% yield).
MS (APCI+) m/z 510 (M+H)$^+$; $^1$H NMR (300 MHz, CDCl$_3$) δ 2.4 (m, 2H), 2.65 (m, 1H), 3.0 (m, 1H), 3.2–3.6 (m, 2H), 4.0 (m, 1H), 4.20 (m, 2H), 4.95 (m, 4H), 5.2 (m, 1H), 6.95 (d, J=9 Hz, 2H), 7.50 (d, J=9 Hz, 2H),), 7.55 (m, 1H), 7.65 (m, 4H), 7.85 (m, 1H), 8.25 (s, 1H), 8.8 (m, 1H), 9.3 (m, 1H).

EXAMPLE 144

N-((3R)-1-{3-[(4'-cyano[1,1'-biphenyl]-4-yl)oxy] propyl}pyrrolidinyl)-2-propanesulfonamide 4'-{3-[(3R)-3-Aminopyrrolidinyl]propoxy}[1,1'-biphenyl]-4-carbonitrile (50 mg, 0.15 mmol), 2-propanesulfonyl chloride (26.2 μL, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (70% yield). MS (APCI+) m/z 428 (M+H)$^+$; $^1$H NMR (300 MHz, CDCl$_3$) δ 1.4 (d, J=7 Hz, 6H), 2.4 (m, 2H), 2.6 (m, 2H), 2.9 (m, 2H), 3.1 (m, 2H), 3.4 (m, 2H), 3.95 (m, 2H), 4.15 (m, 2H), 4.4 (m, 1H), 6.95 (d, J=9 Hz, 2H), 7.50 (d, J=9 Hz, 2H), ), 7.65 (m, 4H).

EXAMPLE 145

N'-((3R)-1-{3-[(4'-cyano[1,1'-biphenyl]-4-yl)oxy] propyl}pyrrolidinyl)-N,N-dimethylsulfamide 4'-{3-[(3R)-3-Aminopyrrolidinyl]propoxy}[1,1'-biphenyl]-4-carbonitrile (50 mg, 0.15 mmol), dimethylsulfamoyl chloride (0.025 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (65% yield).
MS (APCI+) m/z 429 (M+H)$^+$; $^1$H NMR (300 MHz, CDCl$_3$) δ 2.14–2.42 (m, 8H), 2.57 (m, 1H), 2.82 (s, 6H), 3.07 (m, 1H), 3.34 (m, 2H), 3.97 (m, 2H), 4.14 (t, 2H, J=5.6 Hz), 4.36 (m, 1H), 6.97 (d, 2H, J=8.8 Hz), 7.54 (d, 2H, J=8.8 Hz), 7.67 (dd, 4H, J=21.6, 8.6 Hz).

EXAMPLE 146

N-((3R)-1-{3-[(4'-cyano[1,1'-biphenyl]-4-yl)oxy] propyl}pyrrolidinyl)-4-(methylsulfonyl) benzenesulfonamide 4'-{3-[(3R)-3-Aminopyrrolidinyl]propoxy}[1,1'-biphenyl]-4-carbonitrile (50 mg, 0.15 mmol), 4-(methylsulfonyl)benzenesulfonyl chloride (59.4 mg, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (75% yield).
MS (APCI+) m/z 540 (M+H)$^+$; $^1$H NMR (300 MHz, CDCl$_3$) δ 2.13 (m, 2H), 2.23–2.51 (m, 8H), 2.85 (m, 1H), 3.00 (m, 1H), 3.10 (s, 3H), 3.30 (m, 2H), 3.72 (m, 1H), 3.88 (m, 1H), 4.12 (t, 2H, J=5.4 Hz), 4.37 (m, 1H), 6.95 (d, 2H, J=8.8 Hz), 7.53 (d, 2H, J=8.9 Hz), 7.66 (dd, 4H, J=22.1, 8.5 Hz), 8.11 (d, 4H, J=3.1 Hz).

EXAMPLE 147

N-((3R)-1-{3-[(4'-cyano[1,1'-biphenyl]-4-yl)oxy] propyl}pyrrolidinyl)-N-(3,3-dimethylbutanoyl)-3,3-dimethylbutanamide 4'-{3-[(3R)-3-Aminopyrrolidinyl]propoxy}[1,1'-biphenyl]-4-carbonitrile (50 mg, 0.15 mmol), tert-butylacetyl chloride (0.032 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (25% yield).
MS (APCI+) m/z 518 (M+H)$^+$; $^1$H NMR (300 MHz, CDCl$_3$) δ 1.06 (s, 18H), 2.19–2.42 (m, 3H), 2.55 (s, 2H), 2.58 (s, 2H), 3.04–3.53 (m, 8H), 3.60 (m, 1H), 3.67–4.06 (m, 2H), 4.13 (t, 2H, J=5.4 Hz), 4.92 (m, 1H), 6.97 (d, 2H, J=8.9 Hz), 7.53 (d, 2H, J=8.8 Hz), 7.67 (dd, 4H, J=20.9, 8.6 Hz).

EXAMPLE 148

N'-((3R)-1-{3-[(4'-cyano[1,1'-biphenyl]-4-yl)oxy] propyl}pyrrolidinyl)-N'-(dimethylaminocarbonyl)-N, N-dimethylurea 4'-{3-[(3R)-3-Aminopyrrolidinyl]propoxy}[1,1-biphenyl]-4-carbonitrile (50 mg, 0.15 mmol), dimethylcarbamyl chloride (0.021 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (30% yield).
MS (APCI+) m/z 464 (M+H)$^+$; $^1$H NMR (300 MHz, CDCl$_3$) δ 1.86–2.18 (m, 3H), 2.36 (m, 1H), 2.82 (s, 6H), 2.87–3.07 (m, 10H), 3.10 (s, 3H), 3.25 (s, 3H), 3.30–3.52 (m, 4H), 2.36 (m, 2H, J=5.6 Hz), 4.15 (m, 1H), 4.34 (m, 1H), 4.50 (m, 1H), 4.87 (m, 1H), 6.97 (d, 2H, J=8.8 Hz), 7.53 (d, 2H, J=9.1 Hz), 7.67 (dd, 4H, J=17.8, 8.7 Hz).

EXAMPLE 149

N-((3R)-1-{3-[(4'-cyano[1,1'-biphenyl]-4-yl)oxy] propyl}pyrrolidinyl)-N-(1-pyrrolidinylcarbonyl)-1-pyrrolidinecarboxamide 4'-{3-[(3R)-3-Aminopyrrolidinyl]propoxy}[1,1'-biphenyl]-4-carbonitrile (50 mg, 0.15 mmol), 1-pyrrolidinecarbonyl chloride (0.031 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (25% yield).
MS (APCI+) m/z 516 (M+H)$^+$; $^1$H NMR (300 MHz, CDCl$_3$) δ 1.78 (m, 2H), 1.87–2.20 (m, 5H), 2.21–2.47 (m, 1H), 3.17–3.59 (m, 7H), 3.68 (m, 2H), 3.77–4.25 (m, 6H), 4.35 (m, 1H), 4.52 (m, 1H), 4.77–5.00 (m, 1H), 6.97 (d, 2H, J=8.8 Hz), 7.53 (d, 2H, J=8.4 Hz), 7.67 (dd, 4H, J=18.3, 8.5 Hz).

EXAMPLE 150

N-((3R)-1-{3-[(4'-cyano[1,1'-biphenyl]-4-yl)oxy]propyl}pyrrolidinyl)-N-(4-morpholinylcarbonyl)-4-morpholinecarboxamide 4'-{3-[(3R)-3-Aminopyrrolidinyl]propoxy}[1,1'-biphenyl]-4-carbonitrile (50 mg, 0.15 mmol), 4-morpholinecarbonyl chloride (0.027 ml, 0.23 mmol), and N,N-diisopropylethylamine (50 μL, 0.30 mmol) in 2 mL of dichloromethane were stirred at 20° C. for 18 hours. The mixture was evaporated under reduced pressure and the residue was purified by chromatography (CHCl$_3$:MeOH:NH$_4$OH, 9:1:0.1) to provide the title compound (75% yield). $^1$H NMR (300 MHz, CDCl$_3$) δ 2.09 (m, 2H), 2.34 (m, 1H), 3.22 (m, 3H), 3.44 (m, 6H), 3.57 (m, 4H), 3.68 (m, 7H), 3.80 (m, 5H), 4.02 (t, 2H, J=5.4 Hz), 4.13 (m, 1H), 4.36 (m, 1H), 4.53 (m, 1H), 4.90 (m, 1H), 6.96 (d, 2H, J=8.5 Hz), 7.53 (d, 2H, J=8.8 Hz), 7.67 (dd, 4H, J=19.3, 8.8 Hz). MS (APCI+) m/z 548 (M+H)$^+$.

EXAMPLE 151

Cyclopropyl{4-[3-(3-hydroxy-1-pyrrolidinyl)propoxy]phenyl}methanone

EXAMPLE 151A

Cyclopropyl(4-hydroxyphenyl)methanone

Sodium hydroxide in water (50% (w/w), 40.4 mL) was treated over a period of 15 minutes with para-hydroxy-4-chlorobutyrophenone (25.0 g, 137 mmol), followed by additional aqueous sodium hydroxide (25% (w/w), 177 mL). Additional para-hydroxy-4-chlorobutyrophenone (25.0 g, 137 mmol) was added portionwise to the reaction mixture, followed by solid sodium hydroxide (40.4 g). A yellow precipitate formed. After refluxing for 60 minutes, water (50 mL) was added and the resulting mixture was refluxed for another 60 minutes, cooled to room temperature, diluted with water (100 mL) and neutralized with acetic acid. The precipitate was collected by filtration, washed with water, air-dried, and triturated at 40° C. with chloroform (1.5 L). The chloroform solution was dried (MgSO$_4$), filtered, and concentrated. The concentrate was recrystallized from chloroform/hexanes to afford 26.65 g (95%) of the desired product.
MS (APCI-) m/z 161 (M-H)$^-$; $^1$H NMR (300 MHz, CDCl$_3$) δ 7.9 (d, 2H), 6.9 (d, 2H), 2.65 (m, 1H), 1.23 (m, 2H), 1.03 (m, 2H).

EXAMPLE 151B (4-(3-chloropropoxy)phenyl)(cyclopropyl)methanone

The product from Example 151A (10 g, 61.7 mmol), K$_2$CO$_3$ (12.7 g, 91.9 mmol), and 1-bromo-3-chloropropane (10.74 g, 68.2 mmol) in 2-butanone (100 mL) was refluxed for 24 hours, cooled to ambient temperature, filtered, and concentrated. The filtrate was heated at 40° C. under reduced pressure for 3 hours to provide the title compound (13.256 g, 90% yield) of sufficient purity for subsequent use without further purification.

EXAMPLE 151C

Cyclopropyl{4-[3-(3-hydroxy-1-pyrrolidinyl)propoxy]phenyl}methanone

The product from Example 151B (200 mg, 0.83 mmol), 3-hydroxypyrrolidine (72 mg, 0.83 mmol), potassium carbonate (121 mg) and potassium iodide (146 mg) in 10 mL of 2-butanone were heated at 110° C. for 72 hours. The mixture was evaporated under reduced pressure and the residue was purified by chromatography (CHCl$_3$:MeOH:NH$_4$OH, 9:1:0.1) to provide the title compound (68 % yield).
MS (ESI+) m/z 290 (M+H)$^+$; $^1$H NMR (300 MHz, CDCl$_3$) δ 0.93 (m, 2H), 1.20 (m, 2H), 4.18 (t, J=5 Hz, 2H), 4.42 (s, 1H), 6.90 (d, J=7 Hz, 2H), 8.00 (d, J=7 Hz, 2H).

EXAMPLE 152

Cyclopropyl(4-{3-[(3R)-3-hydroxypyrrolidinyl]propoxy}phenyl)methanone (4-(3-Chloropropoxy)phenyl)(cyclopropyl)methanone (150 mg, 0.63 mmol), 3-(3R)-hydroxypyrrolidine (55 mg, 0.63 mmol), potassium carbonate (152 mg) and potassium iodide (183 mg) in 25 mL of 2-butanone were heated at 110° C. for 72 hours. The mixture was evaporated under reduced pressure and the residue was purified by chromatography (CHCl$_3$:MeOH:NH$_4$OH, 9:1:0.1) to provide the title compound (62 % yield).
MS (ESI+) m/z 290 (M+H)$^+$; $^1$H NMR (300 MHz, CDCl$_3$) δ 0.95 (m, 2H), 1.21 (m, 2H), 4.13 (t, J=5 Hz, 2H), 4.40 (s, 1H), 6.95 (d, J=7 Hz, 2H), 8.00 (d, J=7 Hz, 2H).

EXAMPLE 153

4'-{3-[(3R)-3-hydroxypyrrolidinyl]propoxy}[1,1'-biphenyl]-4-carbonitrile

4'-{3-[(3R)-3-Aminopyrrolidinyl]propoxy}[1,1'-biphenyl]-4-carbonitrile (200 mg, 0.74 mmol), (3R)-3-pyrrolidinol (70 mg, 0.81 mmol), potassium carbonate (152 mg) and potassium iodide (183 mg) in 25 mL of 2-butanone were heated at 110° C. for 72 hours. The mixture was evaporated under reduced pressure and the residue was purified by chromatography (CHCl$_3$:MeOH:NH4OH, 9:1:0.1) to provide the title compound (69 % yield).
MS (ESI+) m/z 323 (M+H)$^+$; $^1$H NMR (300 MHz, CDCl$_3$) δ 3.0 (m, 1H), 4.13 (t, J=5 Hz, 2H), 4.40 (s, 1H), 7.0 (d, J=7 Hz, 2H), 7.55 (d, J=7 Hz, 2H), 7.65 (m, 4H).

EXAMPLE 154

4'-[3-(3-oxo-1-pyrrolidinyl)propoxy][1,1'-biphenyl]-4-carbonitrile

Oxalyl chloride (0.195 mmol) in dry CH$_2$Cl$_2$ (5 mL) under an atmosphere of nitrogen at −78° C. was treated with DMSO (0.39 mmol). After 15 minutes of stirring, the product from Example 153 was added and the mixture was stirred for another 15 minutes. Triethylamine (0.45 mmol) was added and the mixture was gradually allowed to warm to 0° C. The solution was partitioned between water (50 mL)

and dichloromethane (50 mL). The organic layer was washed with brine (50 mL), dried over sodium sulfate and filtered. The filtrate was evaporated under reduced pressure and the residue purified by chromatography (CHCl$_3$:MeOH:NH$_4$OH, 9:1:0.1) to provide the title compound (60% yield).
MS (ESI+) m/z 321 (M+H)$^+$; $^1$H NMR (300 MHz, CDCl$_3$) δ 4.15 (t, J=5 Hz, 2H), 7.00 (d, J=7 Hz, 2H), 7.57 (d, J=7 Hz, 2H), =7.63 (m, 4H).

EXAMPLE 155

4'-{3-[(3S)-3-hydroxypyrrolidinyl]propoxy}[1,1'-biphenyl]-4-carbonitrile

4'-{3-[(3R)-3-Aminopyrrolidinyl]propoxy}[1,1'-biphenyl]-4-carbonitrile (180 mg, 0.65 mmol), (3S)-3-pyrrolidinol (57 mg, 0.65 mmol), potassium carbonate (140 mg) and potassium iodide (180 mg) in 20 mL of 2-butanone were heated at 110° C. for 72 hours. The mixture was evaporated under reduced pressure and the residue was purified by chromatography (CHCl$_3$:MeOH:NH$_4$OH, 9:1:0.1) to provide the title compound (61 % yield).
MS (ESI+) m/z 323 (M+H)$^+$; $^1$H NMR (300 MHz, CDCl$_3$) δ 2.02 (m, 2H), 2.25 (m, 3H), 4.15 (t, J=5 Hz, 2H), 6.99 (d, J=7 Hz, 2H), 7.55 (d, J=7 Hz, 2H), 7.65 (m, 4H).

EXAMPLE 156

4'-[3-(3-hydroxy-3-methyl-1-pyrrolidinyl)propoxy][1,1'-biphenyl]-4-carbonitrile

The product from Example 154 (130 mg, 0.41 mmol) in dry THF (6 mL) under an atmosphere of nitrogen at 0° C. was treated with a 3.0M solution of methylmagnesium bromide (0.82 mmol). After warming to ambient temperature and stirring for 2 hours, the mixture was quenched with 3 mL of cold saturated ammonium chloride solution and then the solution was partitioned between water (50 mL) and dichloromethane (50 mL). The organic layer was washed with brine (50 mL), dried over sodium sulfate and filtered. The filtrate was evaporated under reduced pressure and the residue purified by chromatography (CHCl$_3$:MeOH:NH$_4$OH, 9:1:0.1) to provide the title compound (55% yield).
MS (ESI+) m/z 337 (M+H)$^+$; $^1$H NMR (300 MHz, CDCl$_3$) δ 1.22 (s, 3H), 1.93 (m, 2H), 2.1 (m, 2H), 2.82 (m, 2H), 2.92 (d, J=8 Hz, 1H), 3.23 (m, 1H), 4.05 (t, J=5 Hz, 2H), 7.00 (d, J=7 Hz, 2H), 7.57 (d, J=7 Hz, 2H), 7.63 (m, 4H).

EXAMPLE 157

4'-[3-(3-hydroxy-3-isopropyl-1-pyrrolidinyl)propoxy][1,1'-biphenyl]-4-carbonitrile The product from Example 154 (147 mg, 0.46 mmol) in dry THF (10 mL) under an atmosphere of nitrogen at 0° C. was treated with a 2.0M solution of isopropylmagnesium chloride (0.92 mmol). After warming to ambient temperature and stirring for 1 hour, the mixture was quenched with 5 mL of cold saturated ammonium chloride solution and then the solution was partitioned between water (50 mL) and dichloromethane (50 mL). The organic layer was washed with brine (50 mL), dried over sodium sulfate and filtered. The filtrate was evaporated under reduced pressure and the residue purified by chromatography (CHCl$_3$:MeOH:NH$_4$OH, 9:1:0.1) to provide the title compound (75% yield).
MS (ESI+) m/z 365 (M+H)$^+$; $^1$H NMR (300 MHz, CDCl$_3$) δ 4.25 (t, J=5 Hz, 2H), 6.98 (d, J=7 Hz, 2H), 7.55 (d, J=7 Hz, 2H), 7.62 (m, 4H).

EXAMPLE 158

4'-{3-[(3R)-3-hydroxy-3-methylpyrrolidinyl]propoxy}[1,1'-biphenyl]-4-carbonitrile 4'-{3-[(3R)-3-Aminopyrrolidinyl]propoxy}[1,1'-biphenyl]-4-carbonitrile (177 mg, 0.65 mmol), (3R)-3-methyl-3-pyrrolidinol (75 mg, 0.74 mmol), potassium carbonate (153 mg) and potassium iodide (184 mg) in 10 mL of DMF were heated at 110° C. for 10 hours. The mixture was evaporated under reduced pressure and the residue was purified by chromatography (CHCl$_3$:MeOH:NH4OH, 9:1:0.1) to provide the title compound (40 % yield).
MS (ESI+) m/z 337 (M+H)$^+$; $^1$H NMR (300 MHz, CDCl$_3$) δ 1.2 (s, 3H), 4.15 (t, J=5 Hz, 2H), 6.98 (d, J=7 Hz, 2H), 7.55 (d, J=7 Hz, 2H), 7.69 (m, 4H).

EXAMPLE 159

N,N-dimethyl-N-[(3R)-1-(3-{[4'-(1-pyrrolidinylcarbonyl)[1,1'-biphenyl]-4-yl]oxy}propyl)pyrrolidinyl]amine 1-{[4'-(3-Chloropropoxy)[1,1'-biphenyl]-4-yl]carbonyl}pyrrolidine (200 mg, 0.74 mmol), N,N-dimethyl-N-[(3R)-pyrrolidinyl]amine (70 mg, 0.81 mmol), potassium carbonate (152 mg) and potassium iodide (183 mg) in 25 mL of 2-butanone were heated at 110° C. for 72 hours. The mixture was evaporated under reduced pressure and the residue was purified by HPLC chromatography (0 to 95% CH$_3$CN in H$_2$O with 0.1% TFA, 10 minute linear gradient) to provide the title compound in 79% yield.
$^1$HNMR (500 MHz, CDCl$_3$) δ 1.89 (m, 2H), 1.97 (m, 2H), 2.26 (m, 2H), 2.57 (m, 3H), 2.86 (s, 6H), 3.40 (m, 3H), 3.49 (t, 2H, J=6.7 Hz), 3.67 (t, 2H, J=6.8 Hz), 3.74 (m 1H), 3.84 (dd, 1H, J=10.6, 9.0 Hz), 4.02 (m, 1H), 4.10 (t, 2H, J=5.6 Hz), 4.17 (m, 1H), 6.95 (d, 2H, J=8.8 Hz), 7.53 (d, 2H, J=8.8 Hz), 7.57 (s, 4H); MS (APCI) m/z 422 (M+H)$^+$.

EXAMPLE 160

N,N-dimethyl-N-[(3S)-1-(3-{[4'-(1-pyrrolidinylcarbonyl)[1,1'-biphenyl]-4-yl]oxy}propyl)pyrrolidinyl]amine 1-{[4'-(3-Chloropropoxy)[1,1'-biphenyl]-4-yl]carbonyl}pyrrolidine and N,N-dimethyl-N-[(3S)-pyrrolidinyl]amine were processed as described in Example 159 to provide the title compound.
$^1$HNMR (500 MHz, CDCl$_3$) δ 1.88 (m, 3H), 1.98 (m, 2H), 2.26 (m, 3H), 2.56 (m, 3H), 2.86 (s, 6H), 3.45 (m, 5H), 3.70 (m, 3H), 3.84 (m, 1H), 4.03 (m, 1H), 4.10 (t, 2H, J=5.6 Hz), 4.19 (m, 1H), 6.95 (d, 2H, J=8.8 Hz), 7.53 (d, 2H, J=9.1 Hz), 7.57 (s, 4H); MS (APCI) m/z 422 (M+H)$^+$.

EXAMPLE 161

(3R)-1-(3-{[4'-(1-pyrrolidinylcarbonyl)[1,1'-biphenyl]-4-yl]oxy}propyl)-3-pyrrolidinol 1-{[4'-(3-Chloropropoxy)[1,1'-biphenyl]-4-yl]carbonyl}pyrrolidine and (3R)-3-pyrrolidinol were processed as described in Example 159 to provide the title compound.
$^1$HNMR (500 MHz, CDCl$_3$) δ 1.82–2.02 (m, 5H), 2.03–2.50 (m, 16H), 2.96 (m, 2H), 3.14–3.44 (m, 5H), 3.49 (t, 2H, J=6.5 Hz), 3.59 (m, 1H), 3.67 (t, 2H, J=6.9 Hz), 3.87 (m, 1H), 3.98 (m, 1H), 4.06 (m, 1H), 4.12 (m, 1H), 4.64 (m, 1H), 6.94 (d, 2H, J=8.7 Hz), 7.53 (d, 2H, J=8.7 Hz), 7.57 (s, 4H); MS (APCI) m/z 395 (M+H)$^+$.

EXAMPLE 162

N,N-dimethyl-N-[(3R)-1-(3-{4-[4-(1-pyrrolidinylcarbonyl)-1-piperazinyl]phenoxy}propyl)pyrrolidinyl]amine 1-[4-(3-chloropropoxy)phenyl]-4-(1-pyrrolidinylcarbonyl)piperazine and N,N-dimethyl-N-[(3R)-pyrrolidinyl]amine were processed as described in Example 159 to provide the title compound.
$^1$HNMR (500 MHz, CDCl$_3$) δ 1.86 (m, 4H), 2.23 (m, 4H), 2.58 (m, 4H), 2.86 (s, 6H), 3.25 (m, 4H), 3.43 (m, 6H), 3.61 (m, 4H), 3.72 (m, 1H), 3.85 (m, 1H), 4.05 (m, 3H), 4.18 (m, 1H), 6.88 (d, 2H, J=9.0 Hz), 7.17 (d, 2H, J=9.0 Hz); MS (APCI) m/z 430 (M+H)$^+$.

EXAMPLE 163

N,N-dimethyl-N-[(3S)-1-(3-{4-[4-(1-pyrrolidinylcarbonyl)-1-piperazinyl]phenoxy}propyl)pyrrolidinyl]amine 1-[4-(3-chloropropoxy)phenyl]-4-(1-pyrrolidinylcarbonyl)piperazine and N,N-dimethyl-N-[(3S)-pyrrolidinyl]amine were processed as described in Example 159 to provide the title compound.
$^1$HNMR (500 MHz, CDCl$_3$) δ 1.86 (m, 4H), 2.22 (m, 4H), 2.57 (m, 4H), 2.86 (s, 6H), 3.25 (m, 4H), 3.42 (m, 6H), 3.61 (m, 4H), 3.73 (m, 1H), 3.85 (m, 1H), 4.04 (m, 3H), 4.18 (m, 1H), 6.88 (d, 2H, J=9.0 Hz), 7.17 (d, 2H, J=9.0 Hz); MS (APCI) m/z 430 (M+H)$^+$.

Determination of Biological Activity

Histamine-3Receptor Binding

To determine the effectiveness of representative compounds of this invention as histamine-3 receptor ligands (H$_3$ receptor ligands), the following tests were conducted according to methods previously described (European Journal of Pharmacology, 188:219–227 (1990); Journal of Pharmacology and Experimental Therapeutics, 275: 598–604 (1995); Journal of Pharmacology and Experimental Therapeutics, 276:1009–1015 (1996); and Biochemical Pharmacology, 22: 3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid N$_2$ and stored at −70° C. until used in assays. Rat cortical membranes (12 mg wet weight/tube) were incubated with ($^3$H)-N-α-methylhistamine (~0.6 nM) with or without H$_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiationg the incubation assay by addition of the membranes. Thioperamide (3 μM) was used to determine nonspecific binding. Binding incubations were conducted for 30 minutes at 25° C. and terminated by addition of 2 mL of ice cold 50 mM Tris-HCl (ph 7.7) and filtration through 0.3% polyethylenimine-soaked Unifilter plates (Packard). These filters were washed 4 additional times with 2 mL of ice-cold 50 mM Tris-HCl and dreid for 1hour. Radioactivity was determined using liquid scintillation counting techniques. Results were analyzed by Hill transformation and Ki values were determined using the Cheng-Prusoff equiton.

TABLE 1

| Example Number | Ki (nM) |
|---|---|
| 1 | 105 |
| 2 | 68 |
| 3 | 37 |
| 4 | 55 |
| 5 | 6.3 |
| 6 | 95 |
| 7 | 31 |
| 8 | 1721 |
| 9 | 675 |
| 10 | 626 |
| 11 | 4.0 |
| 12 | 71 |
| 13 | 50 |
| 14 | 40 |
| 15 | 7.3 |
| 16 | 67 |
| 17 | 13 |
| 18 | 29 |
| 19 | 3.8 |
| 20 | 12 |
| 21 | 22 |
| 22 | 12 |
| 23 | 33 |
| 24 | 43 |
| 25 | 30 |
| 26 | 57 |
| 27 | 18 |
| 28 | 16 |
| 29 | 5.9 |
| 30 | 10 |
| 31 | 30 |
| 32 | 99 |
| 33 | 16 |
| 34 | 11 |
| 35 | 13 |
| 36 | 12 |
| 37 | 349 |
| 38 | 132 |
| 39 | 7.6 |
| 40 | 51 |
| 41 | 48 |
| 42 | 8.8 |
| 43 | 37 |
| 44 | 52 |
| 45 | 127 |
| 46 | 103 |
| 47 | 12 |
| 48 | 60 |
| 49 | 13 |
| 50 | 60 |
| 51 | 9.3 |
| 52 | 15 |
| 53 | 3.9 |
| 54 | 98 |
| 55 | 2.9 |
| 56 | 4.7 |
| 57 | 3.6 |
| 58 | 3.9 |
| 59 | 3.0 |
| 60 | 5.2 |
| 61 | 4.2 |
| 62 | 6.4 |
| 63 | 12 |
| 64 | 11 |
| 65 | 5.0 |
| 66 | 4.6 |
| 67 | 2.9 |
| 68 | 2.8 |
| 69 | 3.7 |

TABLE 1-continued

| Example Number | Ki (nM) |
| --- | --- |
| 70 | 3.0 |
| 71 | 2.8 |
| 72 | 7.9 |
| 73 | 6.4 |
| 74 | 5.6 |
| 75 | 19 |
| 76 | 4.9 |
| 77 | 5.3 |
| 78 | 8.7 |
| 79 | 7.9 |
| 80 | 10 |
| 81 | 5.0 |
| 82 | 21 |
| 83 | 23 |
| 84 | 9.5 |
| 85 | 5.3 |
| 86 | 1.8 |
| 87 | 4.9 |
| 88 | 6.8 |
| 89 | 11 |
| 90 | 11 |
| 91 | 2.8 |
| 92 | 4.9 |
| 93 | 3.2 |
| 94 | 4.9 |
| 95 | 4.6 |
| 96 | 1.2 |
| 97 | 6.7 |
| 98 | 90 |
| 99 | 63 |
| 100 | 1634 |
| 101 | 179 |
| 102 | 112 |
| 103 | 195 |
| 104 | 173 |
| 105 | 725 |
| 106 | 168 |
| 107 | 200 |
| 108 | 12 |
| 109 | 26 |
| 110 | 30 |
| 111 | 11 |
| 112 | 13 |
| 113 | 13 |
| 114 | 65 |
| 115 | 21 |
| 116 | 14 |
| 117 | 45 |
| 118 | 5.7 |
| 119 | 7.7 |
| 120 | 10 |
| 121 | 16 |
| 122 | 20 |
| 123 | 5.6 |
| 124 | 2.9 |
| 125 | 7.4 |
| 126 | 4.6 |
| 127 | 16 |
| 128 | 2.3 |
| 129 | 192 |
| 130 | 31 |
| 131 | 51 |
| 132 | 74 |
| 133 | 57 |
| 134 | 168 |
| 135 | 132 |
| 136 | 215 |
| 137 | 196 |
| 138 | 118 |
| 139 | 288 |
| 140 | 220 |
| 141 | 342 |
| 142 | 321 |
| 143 | 85 |
| 144 | 21 |
| 145 | 9.6 |
| 146 | 3.0 |

TABLE 1-continued

| Example Number | Ki (nM) |
| --- | --- |
| 147 | 209 |
| 148 | 291 |
| 149 | 329 |
| 150 | 267 |
| 151 | 22 |
| 152 | 8.7 |
| 153 | 42 |
| 154 | 63 |
| 155 | 105 |
| 156 | 45 |
| 157 | 593 |
| 158 | 15 |

As shown by the data in Table 1, the compounds of the present invention bind to the histamine-3 receptor and therefore may have utility in the treatment of diseases or conditions ameliorated with histamine-3 ligands.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configuration as defined in IUPAC 1974Recommendations for Section E, Fundamental Stereochemistry, Pure Appl. Chem., 1976, 45: 13–30.In particular, the stereochemistry at the point of attachment of $R_6$ and $R_9$, as shown in formula I-VII, may independently be either (R) or (S) unless specifically noted otherwise. Additionally, the 3-position of the pyrrolidine ring of formula I-VII may independently be either (R) or (S), unless specifically noted otherwise preferred stereochemistry at the 3-position of the pyrrolidine ring is the (R) configuration for compounds of the present invention. However, the present invention does contemplate various stereoisomers and mixtures thereof and are specifically included within the scope of this invention. Stereoisomers include enantiomers and diastereomers, and mixtures of enantiomers or diastereomers. Individual stereoisomers of compound of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I-VII prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformarnide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The terms "pharmaceutically acceptable salts, esters and amides," as used herein, refer to carboxylate salts, amino acid addition salts, zwitterions, esters and amides of compounds of formula I-VII which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, tris and acetate.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I-VII may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I-VII may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to a parent compound of formula I-VII, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference. Representative examples of prodrugs of the present invention include, but are not limited to, (3R)-1-{3-[(4'-cyano[1,1'-biphenyl]-4-yl)oxy]propyl}pyrrolidinyl methyl sulfate, (3R)-1-{3-[(4'-cyano[1,1'-biphenyl]-4-yl)oxy]propyl}pyrrolidinyl diethyl phosphate, (3R)-1-{3-[(4'-cyano[1,1'-biphenyl]-4-yl)oxy]propyl}pyrrolidinyl acetate, (3R)-1-{3-[(4'-cyano[1,1'-biphenyl]-4-yl)oxy]propyl}pyrrolidinyl dimethylcarbamate, and (3R)-1-{3-[(4'-cyano[1,1'-biphenyl]-4-yl)oxy]propyl}pyrrolidinyl methyl carbonate.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active compounds either chemically synthesized or formed by in vivo biotransformation to compounds of formula I-VII.

The compounds of the present invention, including but not limited to those specified in the examples, possess an affinity for the histamine-3 receptor. As histamine-3 receptor ligands, the compounds of the present invention may be useful for the treatment and prevention of diseases or conditions such as acute myocardial infarction, Alzheimer's disease, attention-deficit hyperactivity disorder, Parkinson's disease, epilepsy, schizophrenia, depression, cutaneous carcinoma, medullary thyroid carcinoma, melanoma, asthma, narcolepsy, Meniere's disease, gastrointestinal disorders, inflammation, migraine, motion sickness, obesity, pain, seizures, and septic shock.

The ability of the compounds of the present invention, including but not limited to those specified in the examples, to treat septic shock and cardiovascular disorders, in particular, acute myocardial infarction may be demonstrated by (Imamura et al., Circ.Res., (1996) 78, 475–481; Imamura et. al., Circ.Res., (1996) 78, 863–869; R. Levi and N. C. E. Smith, "Histamine $H_3$-receptors: A new frontier in myocardial ischemia", J. Pharm. Exp. Ther., 292: 825–830, (2000); and Hatta, E., K Yasuda and R. Levi, "Activation of histamine $H_3$ receptors inhibits carrier-mediated norepinephrine release in a human model of protracted myocradial ischemia", J. Pharm. Exp. Ther., 283: 494–500, (1997)).

The ability of the compounds of the invention, including but not limited to those specified in the examples, to treat sleep disorders, in particular, narcolepsy may be demonstrated by (Lin et al., Brain Res. (1990) 523, 325–330; Monti et al., Neuropsychopharmacology (1996) 15, 31–35;Sakai, et al., Life Sci. (1991) 48, 2397–2404; Mazurkiewicz-Kwilecki and Nsonwah, Can. J. Physiol. Pharmacol. (1989) 67, 75–78; Panula, P. et al., Neuroscience (1998) 44, 465–481); Wada et al., Trends in Neuroscience (1991) 14, 415); and Monti et al., Eur. J. Pharmacol. (1991) 205, 283).

The ability of the compounds of the invention, including but not limited to those specified in the examples, to treat cognition and memory process disorders may be demonstrated by (Mazurkiewicz-Kwilecki and Nsonwah, Can. J. Physiol. Pharmacol. (1989) 67, 75–78; Panula, P. et al., Neuroscience (1998) 44, 465–481;Haas et al., Behav. Brain Res. (1995) 66, 41–44; De Almeida and Izquierdo, Arch. Int. Pharmacodyn. (1986) 283, 193–198; Kamei et al., Psychopharmacology (1990) 102, 312–318; and Kamei and Sakata, Jpn. J. Pharmacol. (1991) 57, 437–482); Schwartz et al., Psychopharmacology; The fourth Generation of Progress. Bloom and Kupfer (eds). Raven Press, New York, (1995) 397; and Wada et al., Trends in Neurosci., (1991) 14, 415).

The ability of the compounds of the invention, including but not limited to those specified in the examples, to treat attention-deficit hyperactivity disorder (ADHD) may be demonstrated by (Shaywitz et al., Psychopharmacology (1984) 82, 73–77; Dumery and Blozovski, Exp. Brain Res. (1987) 67, 61–69; Tedford et al., J. Pharmacol. Exp. Ther. (1995) 275, 598–604; and Tedford et al., Soc. Neurosci. Abstr. (1996) 22, 22).

The ability of the compounds of the invention, including but not limited to those specified in the examples, to treat seizures, in particular, epilepsy may be demonstrated by (Yokoyama et al., Eur. J. Pharmacol. (1993) 234, 129; Yokoyama and Iinuma, CNS Drugs (1996) 5, 321; Onodera et al., Prog. Neurobiol. (1994) 42, 685;R. Leurs, R. C. Vollinga and H. Timmerman, "The medicinal chemistry and therapeutic potentials of ligand of the histamine $H_3$ receptor", Progress in Drug Research 45: 170–165, (1995); Leurs and Timmerman, Prog. Drug Res. (1992) 39, 127; The Histamine $H_3$Receptor, Leurs and Timmerman (eds), Elsevier Science, Amsterdam, The Netherlands (1998); H. Yokoyama and K. Iinuma, "Histamine and Seizures: Implications for the treatment of epilepsy", CNS Drugs, 5(5); 321–330, (1995); and K. Hurukami, H. Yokoyama, K. Onodera, K. Iinuma and T. Watanabe, AQ-0145, "A newly developed histamine $H_3$ antagonist, decreased seizure susceptibility of eletrically induced convulsions in mice", Meth. Find. Exp. Clin. Pharmacol., 17(C): 70–73, (1995)).

The ability of the compounds of the invention, including but not limited to those specified in the examples, to treat motion sickness, Alzheimer's disease, and Parkinson's disease may be demonstrated by (Onodera et al., Prog. Neurobiol. (1994) 42, 685; Leurs and Timmerman, Prog. Drug Res. (1992) 39, 127; and The Histamine $H_3$Receptor, Leurs and Timmerman (eds), Elsevier Science, Amsterdam, The Netherlands (1998)).

The ability of the compounds of the invention, including but not limited to those specified in the examples, to treat narcolepsy, schizophrenia, depression, and dementia may be demonstrated by (R. Leurs, R. C. Vollinga and H. Timmerman, "The medicinal chemistry and therapeutic potentials of ligand of the histamine $H_3$ receptor", Progress in Drug Research 45: 170–165, (1995); and The Histamine $H_3$Receptor, Leurs and Timmerman (eds), Elsevier Science, Amsterdam, The Netherlands (1998)).

The ability of the compounds of the invention, including but not limited to those specified in the examples, to treat obesity may be demonstrated by (Leurs et al., Trends in Pharm. Sci. (1998) 19, 177–183).

The ability of the compounds of the invention, including but not limited to those specified in the examples, to treat inflammation and pain may be demonstrated by (Phillips et al., Annual Reports in Medicinal Chemistry (1998) 33, 31–40).

The ability of the compounds of the invention, including but not limited to those specified in the examples, to treat migraine may be demonstrated by (R. Leurs, R. C. Vollinga and H. Timmerman, "The medicinal chemistry and therapeutic potentials of ligand of the histamine $H_3$ receptor", Progress in Drug Research 45: 170–165, (1995); and Matsubara et al., Eur. J. Pharmacol. (1992) 224, 145; and Rouleau et al., J. Pharmacol. Exp. Ther. (1997) 281, 1085).

The ability of the compounds of the invention, including but not limited to those specified in the examples, to treat cancer, in particular, melanoma, cutaneous carcinoma and medullary thyroid carcinoma may be demonstrated by (Polish Med. Sci. Mon., (1998) vol. 4, issue 5, 747; Adam Szelag, "Role of histamine $H_3$-receptors in the proliferation of neoplastic cells in vitro", Med. Sci. Monit., 4(5): 747–755, (1998); and Fitzsimons, C., H. Duran, F. Labombarda, B. Molinari and E. Rivera, "Histamine receptors signalling in epidermal tumor cell lines with H-ras gene alterations", Inflammation Res., 47 (Suppl 1): S50-S51, (1998)).

The ability of the compounds of the invention, including but not limited to those specified in the examples, to treat vestibular dysfunctions, in particular, Meniere's disease may be demonstrated by (R. Leurs, R. C. Vollinga and H. Timmerman, "The medicinal chemistry and therapeutic potentials of ligand of the histamine $H_3$ receptor", Progress in Drug Research 45: 170–165, (1995).

The ability of the compounds of the present invention, including but not limited to those specified in the examples, to treat asthma may be demonstrated by (Delaunois A., Gustin P., Garbarg M., and Ansay M., "Modulation of acetylcholine, capsaicin and substance P effects by histamine $H_3$ receptors in isolated perfused rabbit lungs", European Journal of Pharmacology 277(2–3):243–250, (1995); and (Dimitriadou, et al., "Functional relationship between mast cells and C-sensitive nerve fibres evidenced by histamine $H_3$-receptor modulation in rat lung and spleen", Clinical Science. 87(2):151–163, (1994).

Aqueous liquid compositions of the present invention are particularly useful for the treatment and prevention of asthma, epilepsy, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 10 mg/kg/day. For purposes of oral

What is claimed is:

1. A compound of formula I

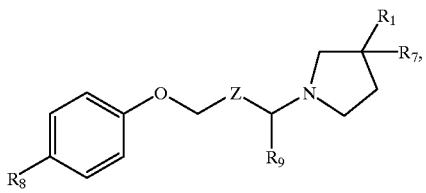

or a pharmaceutically acceptable salt thereof, wherein
Z is selected from the group consisting of a covalent bond and CH$_2$;
R$_1$ is NR$_3$R$_4$;
R$_3$ and R$_4$ are independently selected from the group consisting of hydrogen, alkenyl, alkyl, and alkynyl;
R$_7$ is selected from the group consisting of hydrogen and alkyl;
R$_8$ is selected from the group consisting of alkylcarbonyl, aryl, arylcarbonyl, and arylcarbonylaryl;
R$_9$ is selected from the group consisting of hydrogen and lower alkyl;
wherein at each occurrence of said aryl, arylalkenylcarbonyl, arylalkenylsulfonyl, arylalkylcarbonyl, arylalkylsulfonyl, arylarylcarbonyl, arylarylsulfonyl, arylcarbonyl, arylcarbonylaryl, arylcarbonylheterocycle, arylheterocylecarbonyl, arylheterocylesulfonyl, aryloxyarylcarbonyl, aryloxyarylsulfonyl, arylsulfonyl, cycloalkylcarbonylaryl, heterocyclearylcarbonyl, heterocyclearylsulfonyl, heterocyclecarbonylaryl, heterocycleoxyarylcarbonyl, and heterocycleoxyarylsulfonyl, the aryl portion can be optionally substituted with 1, 2, or 3 substituents selected from the group consisting of alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, carboxy, carboxyalkyl, cyano, cyanoalkyl, formyl, halogen, haloalkoxy, haloalkyl, hydroxy, hydroxyalkyl, mercapto, and nitro; and
wherein at each occurrence of said arylcarbonylheterocycle, arylheterocylecarbonyl, arylheterocylesulfonyl, cycloalkylcarbonylheterocycle, heterocycle, heterocyclealkyl, heterocyclealkylcarbonyl, heterocyclealkylsulfonyl, heterocyclearylcarbonyl, heterocyclearylsulfonyl, heterocyclecarbonyl, heterocyclecarbonylaryl, heterocyclecarbonylheterocycle, heterocycleheterocyclecarbonyl, heterocycleheterocyclesulfonyl, heterocycleoxyalkylcarbonyl, heterocycleoxyarylcarbonyl, heterocycleoxyarylsulfonyl, heterocyclesulfonyl, and heterocyclethioalkylcarbonyl, the heterocycle portion can be optionally substituted with 1, 2, or 3 substituents selected from the group consisting of alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

2. A compound according to claim 1 wherein
R$_1$ is NR$_3$R$_4$;
R$_3$ and R$_4$ are independently selected from the group consisting of hydrogen, alkenyl, alkyl, and alkynyl;
R$_7$ is hydrogen; and
R$_8$ is selected from the group consisting of alkylcarbonyl, aryl, arylcarbonyl, and arylcarbonylaryl.

3. A compound according to claim 1 wherein
R$_1$ is NR$_3$R$_4$;
R$_3$ and R$_4$ are independently selected from the group consisting of hydrogen and alkyl;
R$_7$ is hydrogen; and
R$_8$ is selected from the group consisting of alkylcarbonyl, aryl, arylcarbonyl, and arylcarbonylaryl.

4. A compound according to claim 1 wherein
Z is CH$_2$;
R$_1$ is NR$_3$R$_4$;
R$_3$ and R$_4$ are independently selected from the group consisting of hydrogen and alkyl;
R$_7$ is hydrogen;
R$_8$ is selected from the group consisting of acetyl, propionyl, and 4-cyanophenyl; and
R$_9$ is hydrogen.

5. A compound according to claim 1 selected from the group consisting of
tert-butyl 1-{3-[(4'-cyano[1,1'-biphenyl]-4-yl)oxy]propyl}-3-pyrrolidinylcarbamate;
N,N-dimethyl-N-[(3S)-1-(3-{[4'-(1-pyrrolidinylcarbonyl)[1,1'-biphenyl]-4-yl]oxy}propyl)pyrrolidinyl]amine;
N,N-dimethyl-N-[(3S)-1-(3-{4-[4-(1-pyrrolidinylcarbonyl)-1-piperazinyl]phenoxy}propyl)pyrrolidinyl]amine;
1-(4-{3-[(3R)-3-aminopyrrolidinyl]propoxy}phenyl)-1-propanone;
4'-{3-[(3R)-3-aminopyrrolidinyl]propoxy}[1,1'-biphenyl]-4-carbonitrile;
4'-{3-[(3R)-3-(dimethylamino)pyrrolidinyl]propoxy}[1,1'-biphenyl]-4-carbonitrile;
4'-{3-[(3R)-3-(methylamino)pyrrolidinyl]propoxy}[1,1'-biphenyl]-4-carbonitrile; and
tert-butyl (3S)-1-{2-[(4'-cyano[1,1'-biphenyl]-4-yl)oxy]ethyl}pyrrolidinylcarbamate.

6. A compound according to claim 1 wherein
Z is a covalent bond;
R$_1$ is NR$_3$R$_4$;
R$_3$ and R$_4$ are independently selected from the group consisting of hydrogen-and alkyl;
R$_7$ is hydrogen;
R$_8$ is selected from the group consisting of acetyl, propionyl, and 4-cyanophenyl; and
R$_9$ is hydrogen.

7. A compound according to claim 6 that is tert-butyl (3S)-1-{2-[(4'-cyano[1,1'-biphenyl]-4-yl)oxy]ethyl}pyrrolidinylcarbamate.

8. A pharmaceutical composition comprising a therapeutically effective amount of a compound of claim 1 in combination with a pharmaceutically acceptable carrier.

9. A method for modulating the effects of the histamine-3 receptor in a mammal comprising administering a therapeutically effective amount of a compound of claim 1.

10. A method of treating a disorder wherein the disorder is ameliorated by modulating the the histamine-3 receptor in a mammal in need of such treatment comprising administering a therapeutically effective amount of a compound of claim 1.

11. The method of claim 10 wherein the disorder is selected from the group consisting of acute myocardial infarction, asthma, cutaneous carcinoma, depression, inflammation, medullary thyroid carcinoma, melanoma, Meniere's disease, migraine, motion sickness, obesity, pain, Parkinson's disease, schizophrenia, seizures, and septic shock.

12. The method of claim 10 wherein the disorder is Alzheimer's disease.

13. The method of claim 10 wherein the disorder is attention-deficit hyperactivity disorder.

14. The method of claim 10 wherein the disorder is epilepsy.

15. The method of claim 10 wherein the disorder is narcolepsy.

* * * * *